United States Patent
Kang et al.

(10) Patent No.: US 11,912,777 B2
(45) Date of Patent: Feb. 27, 2024

(54) ANTIBODIES BINDING TNFR2 AND USES THEREOF

(71) Applicant: Nanjing Leads Biolabs Co., Ltd., Jiangsu (CN)

(72) Inventors: Xiaoqiang Kang, Plainsboro, NJ (US); Shoupeng Lai, Germantown, MD (US); Xiao Huang, Jiangsu (CN); Huan Lin, Jiangsu (CN); Yujia Dang, Jiangsu (CN)

(73) Assignee: Nanjing Leads Biolabs Co., Ltd., Nanjing (CN)

( * ) Notice: Subject to any disclaimer, the term of this patent is extended or adjusted under 35 U.S.C. 154(b) by 0 days.

(21) Appl. No.: 18/064,061

(22) Filed: Dec. 9, 2022

(65) Prior Publication Data

US 2023/0212302 A1 Jul. 6, 2023

Related U.S. Application Data

(63) Continuation of application No. PCT/CN2021/099732, filed on Jun. 11, 2021.

(30) Foreign Application Priority Data

Jun. 12, 2020 (WO) ................ PCT/CN2020/095933

(51) Int. Cl.
| | |
|---|---|
| *C07K 16/28* | (2006.01) |
| *A61P 1/00* | (2006.01) |
| *A61P 35/00* | (2006.01) |
| *G01N 33/68* | (2006.01) |
| *A61K 39/00* | (2006.01) |

(52) U.S. Cl.
CPC ............ *C07K 16/2878* (2013.01); *A61P 1/00* (2018.01); *A61P 35/00* (2018.01); *C07K 16/2818* (2013.01); *G01N 33/6863* (2013.01); *A61K 2039/505* (2013.01); *A61K 2039/507* (2013.01); *C07K 2317/24* (2013.01); *C07K 2317/31* (2013.01); *C07K 2317/34* (2013.01); *C07K 2317/732* (2013.01); *C07K 2317/74* (2013.01); *C07K 2317/76* (2013.01); *C07K 2317/92* (2013.01); *G01N 2333/70578* (2013.01)

(58) Field of Classification Search
CPC . C07K 16/2878; C07K 2317/76; A61P 35/00; A61K 2039/505; G01N 33/6863
See application file for complete search history.

(56) References Cited

U.S. PATENT DOCUMENTS

| | | |
|---|---|---|
| 2014/0051647 A1 | 2/2014 | Kobayashi et al. |
| 2019/0202925 A1 | 7/2019 | Thompson |
| 2019/0330359 A1 | 10/2019 | Maury et al. |

FOREIGN PATENT DOCUMENTS

| | | |
|---|---|---|
| WO | 2014124134 A1 | 8/2014 |
| WO | 2016187068 A1 | 11/2016 |
| WO | 2017040312 A1 | 3/2017 |
| WO | 2018213064 A1 | 11/2018 |
| WO | 2019094559 A2 | 5/2019 |
| WO | 2020041361 A1 | 2/2020 |
| WO | 2020061210 A1 | 3/2020 |
| WO | 2020089473 A2 | 5/2020 |
| WO | 2020089474 A1 | 5/2020 |
| WO | 2020102739 A1 | 5/2020 |

OTHER PUBLICATIONS

Almagro JC, Fransson J. Humanization of antibodies. Front Biosci. Jan. 1, 2008;13:1619-33. (Year: 2008).*
Edwards et al. The remarkable flexibility of the human antibody repertoire;isolation of over one thousand different antibodies to a single protein, BLyS. J Mol Biol Nov. 14, 2003;334(1):103-18. (Year: 2003).*
Kussie et al. A single engineered amino acid substitution changes antibody fine specificity.J Immunol. Jan. 1, 1994;152(1):146-52. (Year: 1994).*
Nie Y, He J, Shirota H, Trivett Al, Yang D, Klinman DM, Oppenheim JJ, Chen X. Blockade of TNFR2 signaling enhances the immunotherapeutic effect of CpG ODN in a mouse model of colon cancer. Sci Signal. Jan. 2, 2018;11(511):eaan0790. (Year: 2018).*
Nie et al., "Blockade of TNFR2 signaling enhances the immunotherapeutic effect of CpG ODN in a mouse model of colon cancer", Sci Signal, vol. 11, No. 511, Jan. 2, 2018, 20 pages.
Okubo et al., "Homogeneous Expansion of Human T-Regulatory Cells Via Tumor Necrosis Factor Receptor 2", Scientific Reports, vol. 3, No. 3153, Nov. 6, 2013, 11 pages.
Salomon et al., "Tumor Necrosis Factor α and Regulatory T Cells in Oncoimmunology", Frontiers in Immunology, vol. 9, Article 444, Mar. 12, 2018, 12 pages.
Torrey et al., "Targeted killing of TNFR2-expressing tumor cells and Tregs by TNFR2 antagonistic antibodies in advanced Sézary syndrome", Leukemia, Oct. 24, 2018, 13 pages.

(Continued)

*Primary Examiner* — Aurora M Fontainhas
*Assistant Examiner* — Jennifer A Benavides
(74) *Attorney, Agent, or Firm* — McNeill Baur PLLC

(57) ABSTRACT

The present invention relates to a novel antibody and antibody fragment that specifically binds to TNFR2 and to a composition comprising said antibody or antibody fragment. In addition, the present invention relates to a nucleic acid encoding the antibody or an antibody fragment thereof and a host cell comprising the same, and to a related use thereof. Besides, the present invention relates to the use of the antibody and antibody fragment for treatment and diagnosis.

30 Claims, 9 Drawing Sheets

Specification includes a Sequence Listing.

(56) References Cited

OTHER PUBLICATIONS

Vanamee et al., "TNFR2: A Novel Target for Cancer Immunotherapy", Trends in Molecular Medicine, vol. 23, No. 11, Nov. 2017, pp. 1037-1046.
Wei et al., "Discovery and characterization of novel TNFR2 antibodies to modulate T cell activities in immunosuppressive environment", In Cancer Research, vol. 80, No. 16, 2020, 1 page.
Williams et al., "Phenotypic screening reveals TNFR2 as a promising target for cancer immunotherapy", Oncotarget, vol. 7, No. 42, Sep. 10, 2016, pp. 68278-68291.
Sampson et al., "A novel human TNFR2 antibody (MM-401) modulates T cell responses in anti-cancer immunity", Cancer Res, vol. 79, No. 13 Supplement, 2019, p. 555. (4 pages) https://www.merrimack.com/wp-content/uploads/AACR_human_mAbs_poster.pdf.

\* cited by examiner

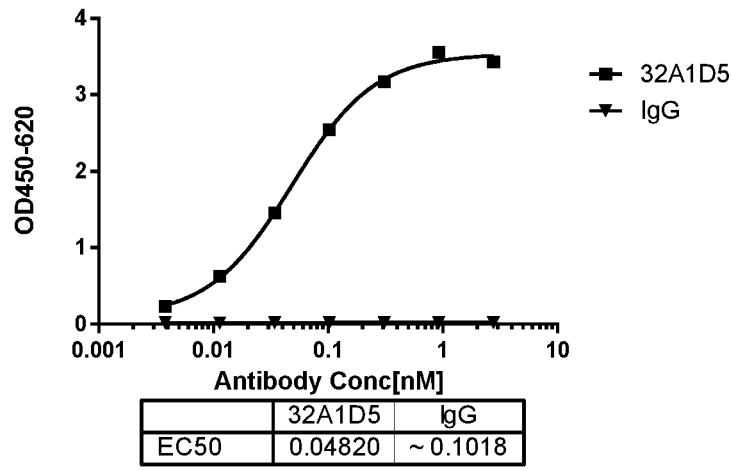
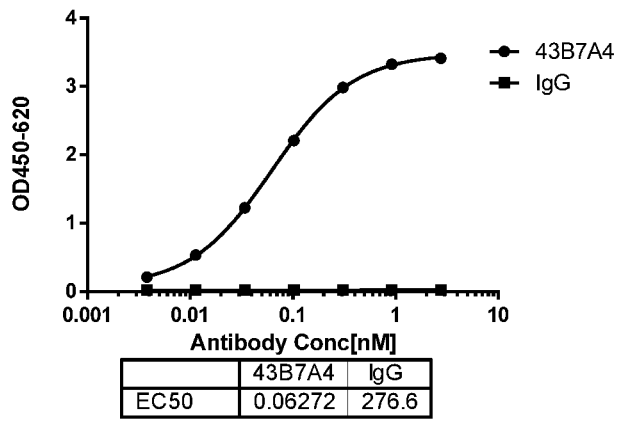
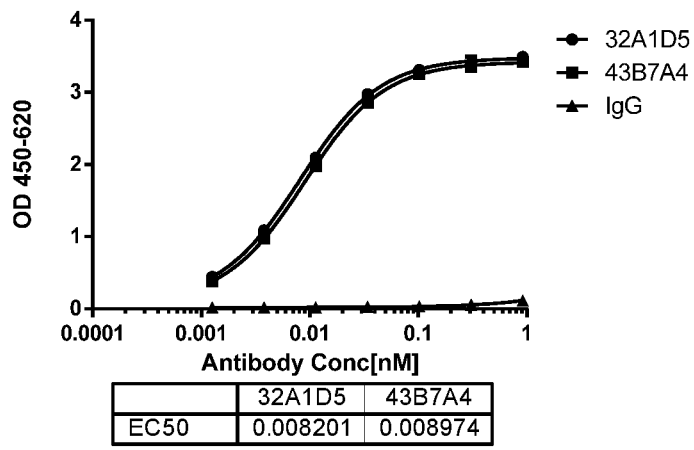
Fig. 1 Chimeric antibodies bound to human/Cynomolgus TNFR2 protein

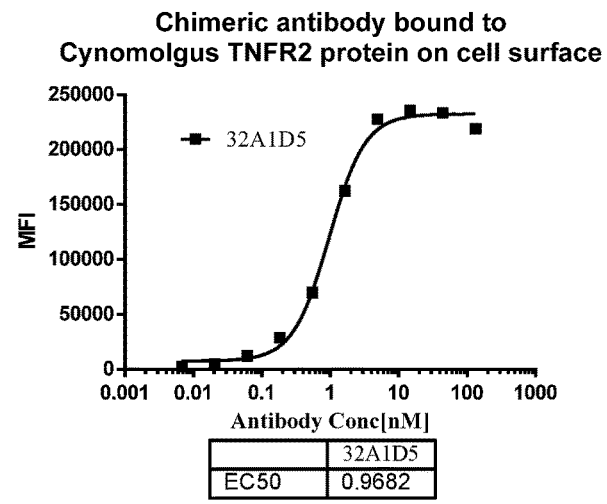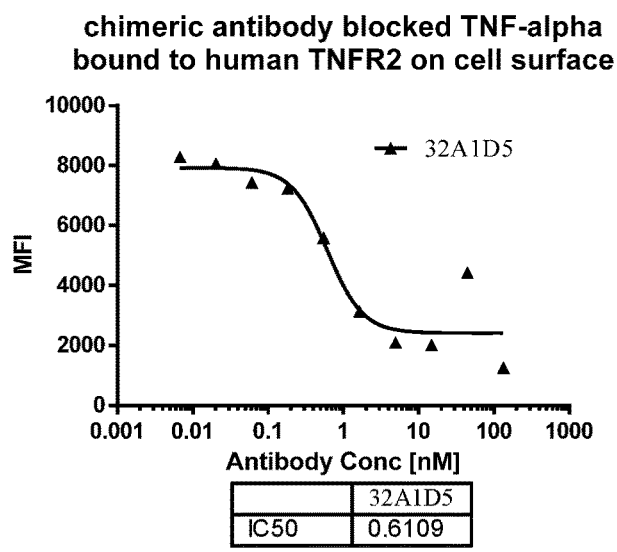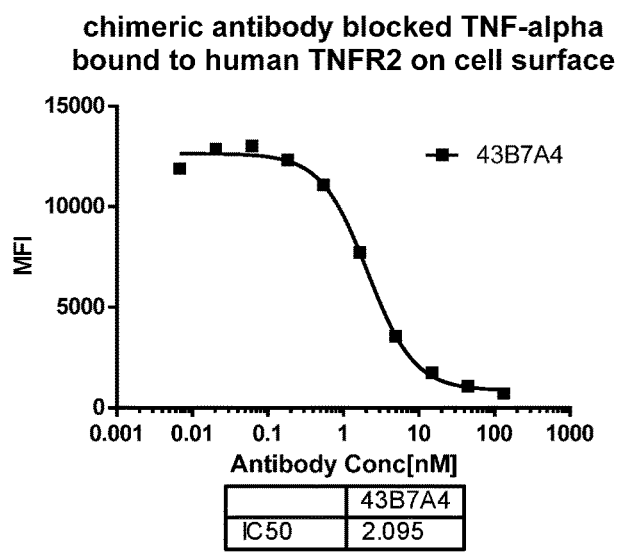
Fig. 2 Cell binding and blocking of chimeric antibodies

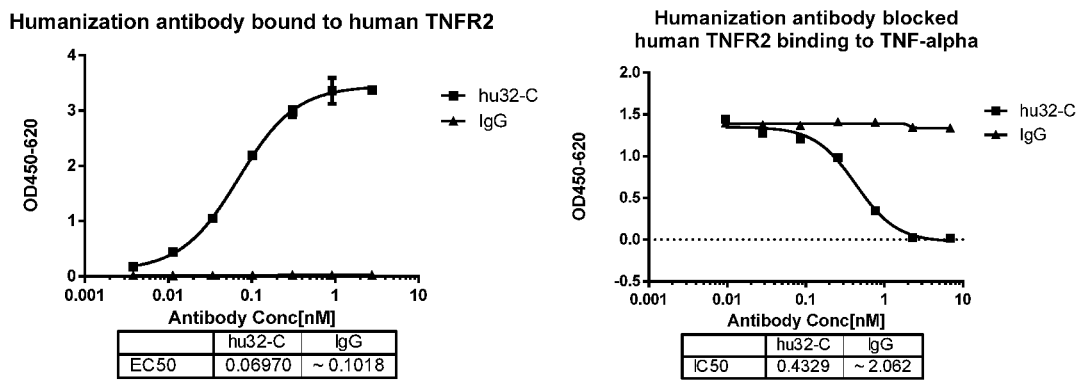
(a) Humanized antibody hu32-C binding & blocking ELISA
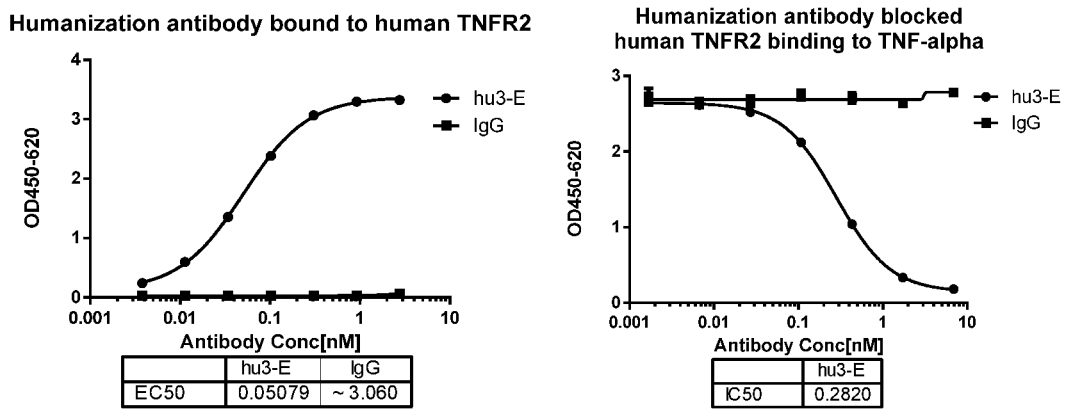
(b) Humanized antibody hu3-E binding & blocking ELISA
Fig. 3 Anti-TNFR2 humanized antibodies in ELISA-based assay

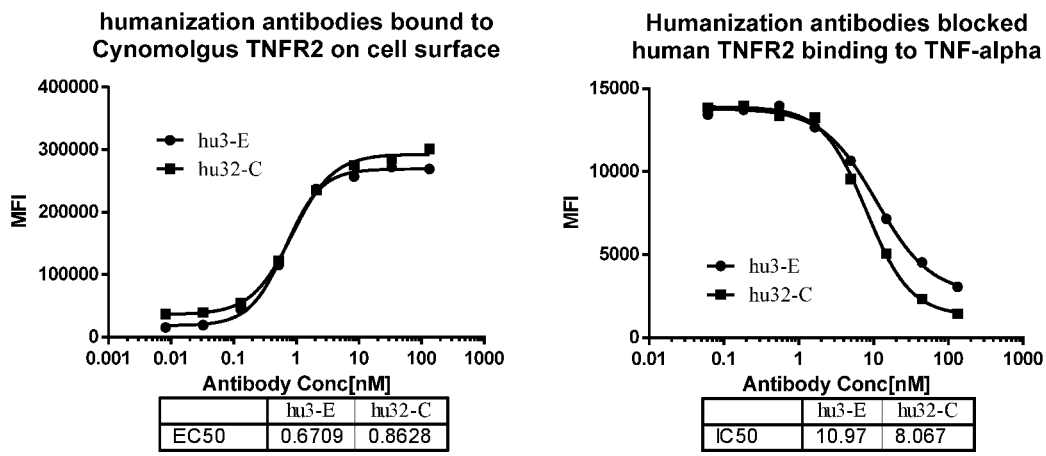
Fig. 4 Cell binding and blocking of humanized antibodies
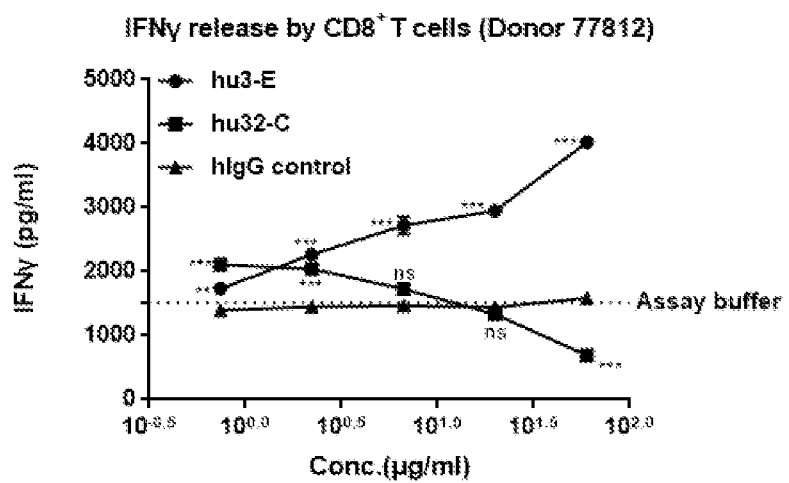
Fig. 5 Costimulate human CD8+ T cell to release IFNγ

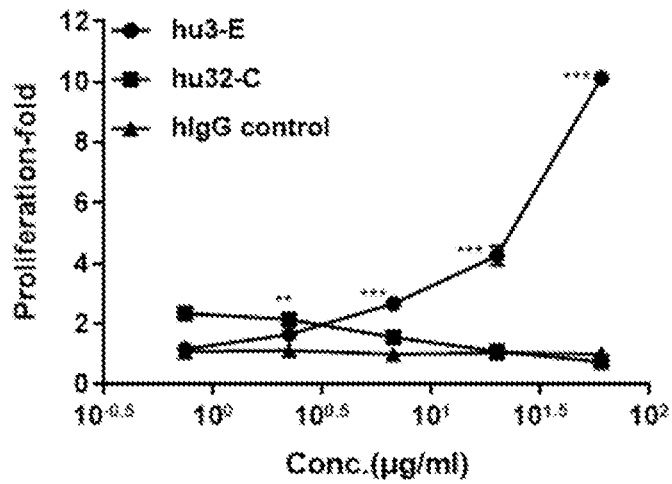
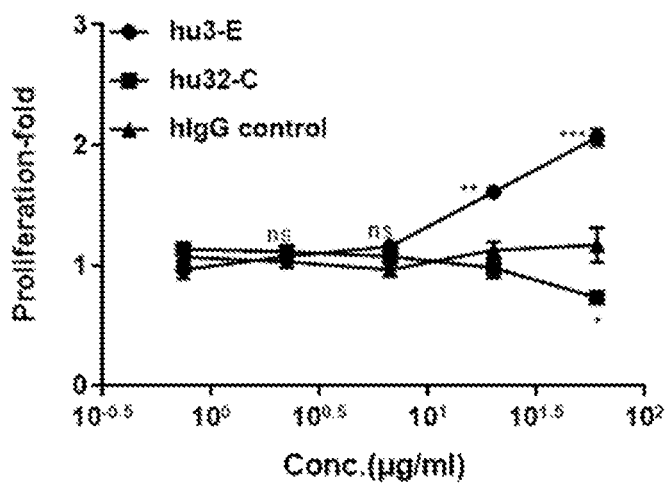
Fig. 6 Proliferation of T cells mediated by anti-TNFR2 antibody costimulation *in vitro* Cell Viability Assay

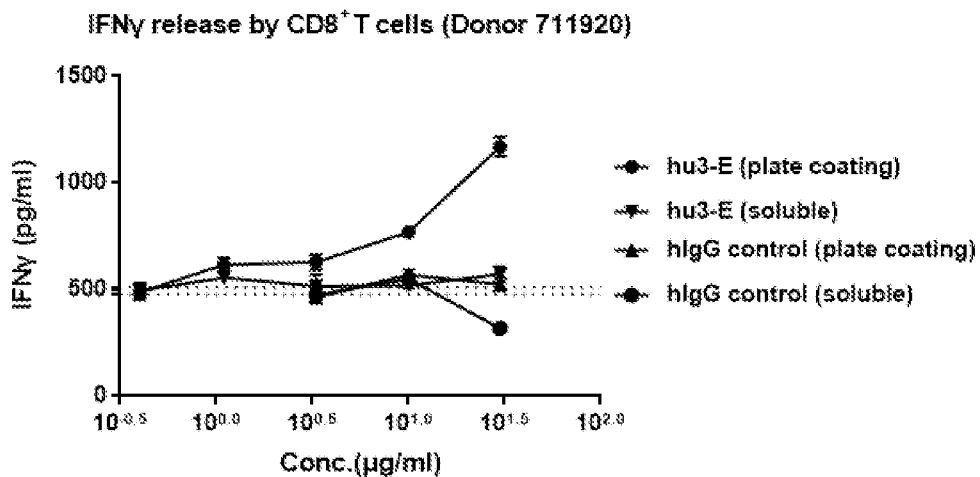
Fig. 7 Activation of T cells mediated by anti-TNFR2 antibody costimulation *in vitro* depended on Fc cross-linking
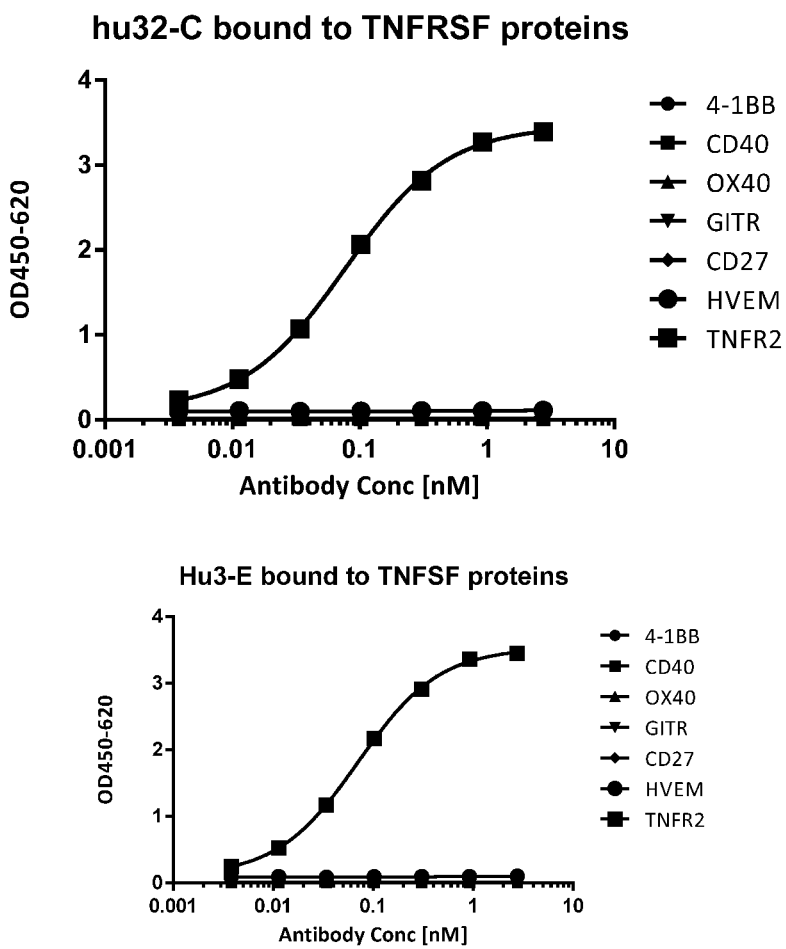
Fig. 8 Family cross-binding of TNFR superfamily protein

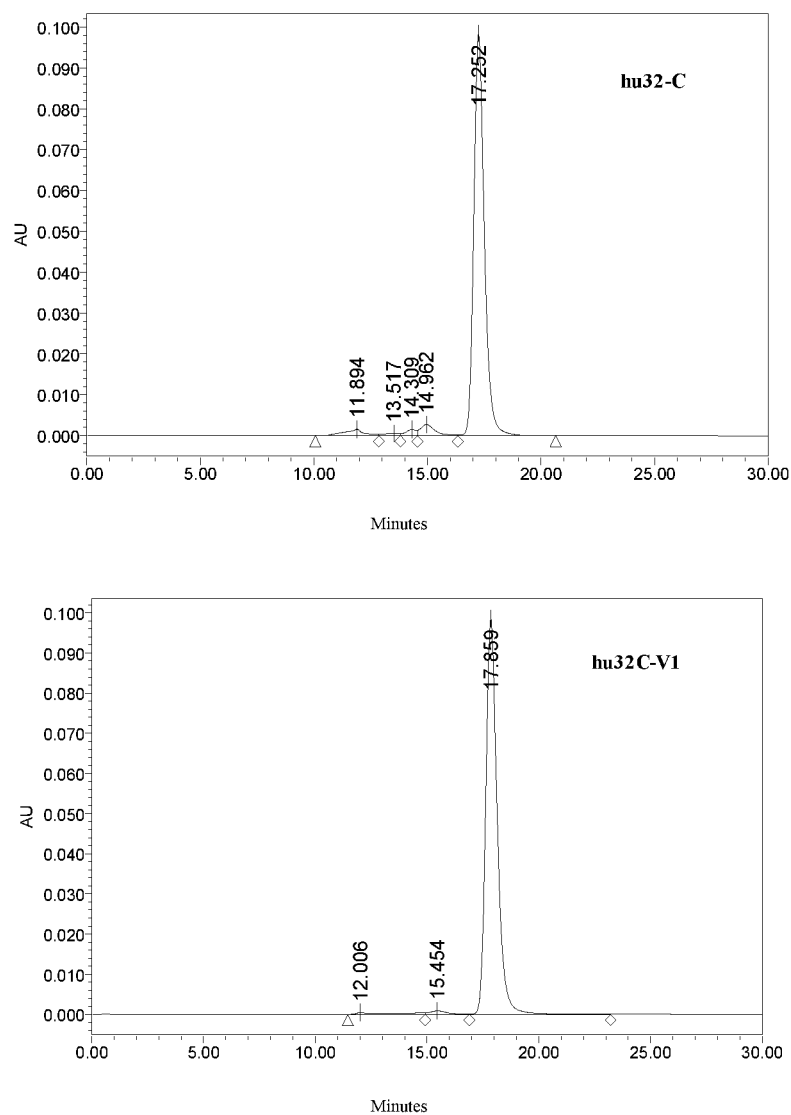
Fig. 9 The purity of humanized antibodies hu32-C and hu32C-V1 in SEC-HPLC

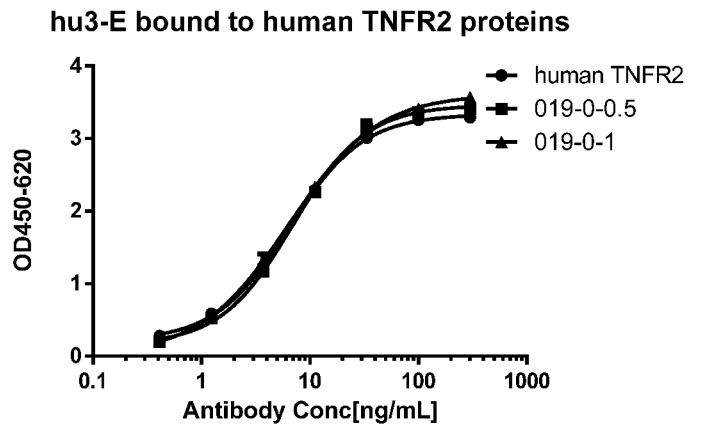
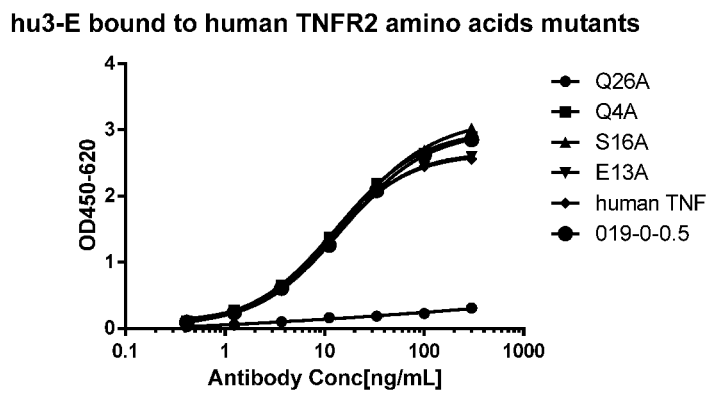
Fig. 10 Anti-TNFR2 antibody hu3-E epitope mapping
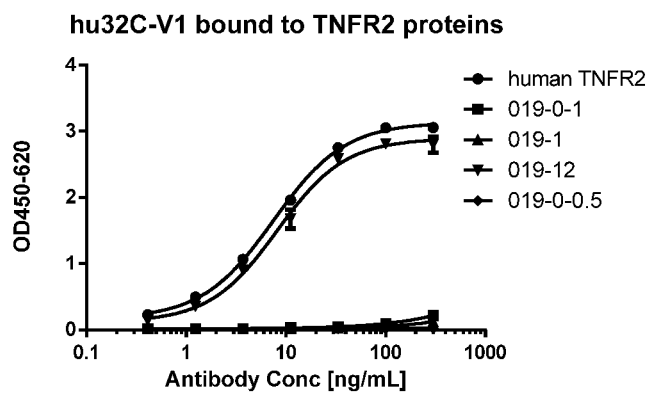
Fig. 11 Anti-TNFR2 antibody hu32C-V1 epitope mapping

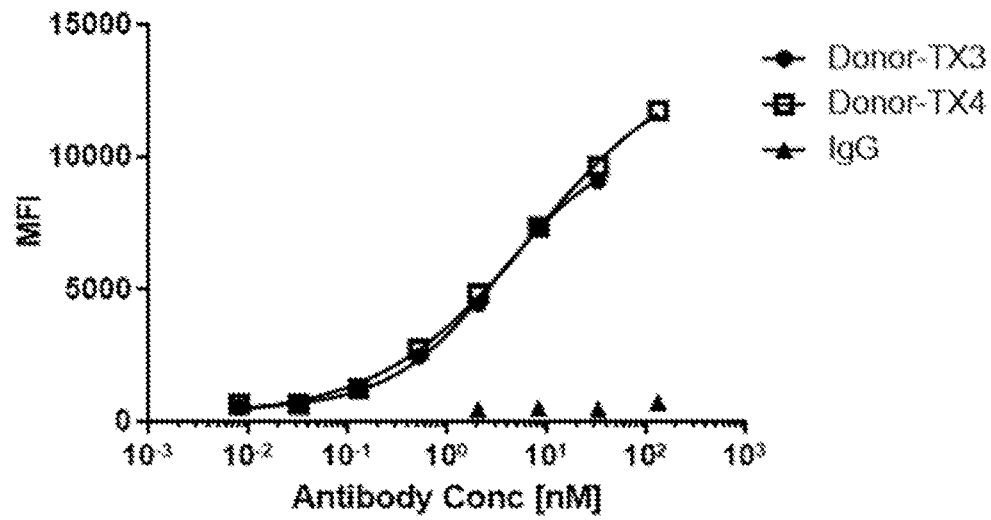
Fig.12 Anti-TNFR2 antibody hu3-E bound to TNFR2 on activated PBMC cells
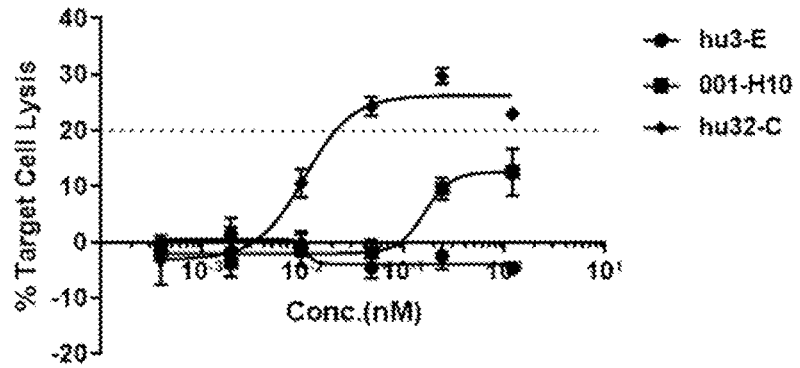
Fig.13 ADCC effect of anti-human TNFR2 antibodies on Treg cells
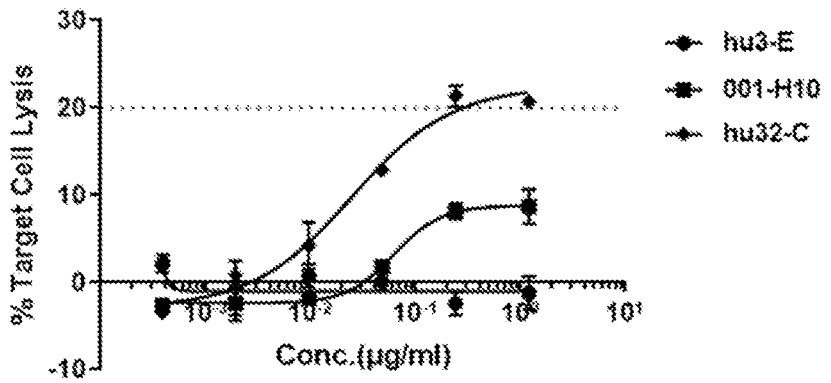
Fig.14 ADCC effect of anti-human TNFR2 antibodies on CD8+ T cells

```
SEQUENCE LISTING

Sequence total quantity: 75
SEQ ID NO: 1             moltype = AA  length = 7
FEATURE                  Location/Qualifiers
REGION                   1..7
                         note = synthetic
source                   1..7
                         mol_type = protein
                         organism = synthetic construct
SEQUENCE: 1
TLGMGVG                                                                    7

SEQ ID NO: 2             moltype = AA  length = 16
FEATURE                  Location/Qualifiers
REGION                   1..16
                         note = synthetic
source                   1..16
                         mol_type = protein
                         organism = synthetic construct
SEQUENCE: 2
HIWWDADKYY NPALKS                                                         16

SEQ ID NO: 3             moltype = AA  length = 9
FEATURE                  Location/Qualifiers
REGION                   1..9
```

-continued

```
                          note = synthetic
source                    1..9
                          mol_type = protein
                          organism = synthetic construct
SEQUENCE: 3
MTGTRYFDV                                                                    9

SEQ ID NO: 4              moltype = AA  length = 11
FEATURE                   Location/Qualifiers
REGION                    1..11
                          note = synthetic
source                    1..11
                          mol_type = protein
                          organism = synthetic construct
SEQUENCE: 4
KASQNINKFI A                                                                11

SEQ ID NO: 5              moltype = AA  length = 7
FEATURE                   Location/Qualifiers
REGION                    1..7
                          note = synthetic
source                    1..7
                          mol_type = protein
                          organism = synthetic construct
SEQUENCE: 5
YTSTLQP                                                                      7

SEQ ID NO: 6              moltype = AA  length = 8
FEATURE                   Location/Qualifiers
REGION                    1..8
                          note = synthetic
source                    1..8
                          mol_type = protein
                          organism = synthetic construct
SEQUENCE: 6
LQYGVLWT                                                                     8

SEQ ID NO: 7              moltype = AA  length = 119
FEATURE                   Location/Qualifiers
REGION                    1..119
                          note = synthetic
source                    1..119
                          mol_type = protein
                          organism = synthetic construct
SEQUENCE: 7
QVTLKESGPG ILQPSQTLSL TCSFSGFSLN TLGMGVGWIR QPSGKGLEWL AHIWWDADKY    60
YNPALKSRLT ISKDTSKNHV FLKIANADTA DTATYYCARM TGTRYFDVWG TGTTVTVSS    119

SEQ ID NO: 8              moltype = AA  length = 106
FEATURE                   Location/Qualifiers
REGION                    1..106
                          note = synthetic
source                    1..106
                          mol_type = protein
                          organism = synthetic construct
SEQUENCE: 8
DIQMTQSPSS LSASLGDKVT ITCKASQNIN KFIAWYQHKP GEGPRLLIHY TSTLQPGIPS    60
RFSGSGSGSD YSFSINNLEP EDIASYYCLQ YGVLWTFGGG TKLEIK                  106

SEQ ID NO: 9              moltype = AA  length = 5
FEATURE                   Location/Qualifiers
REGION                    1..5
                          note = synthetic
source                    1..5
                          mol_type = protein
                          organism = synthetic construct
SEQUENCE: 9
TYGMS                                                                        5

SEQ ID NO: 10             moltype = AA  length = 17
FEATURE                   Location/Qualifiers
REGION                    1..17
                          note = synthetic
source                    1..17
                          mol_type = protein
                          organism = synthetic construct
SEQUENCE: 10
WIHTYSGVPT YADDFKG                                                          17
```

```
SEQ ID NO: 11              moltype = AA   length = 7
FEATURE                    Location/Qualifiers
REGION                     1..7
                           note = synthetic
source                     1..7
                           mol_type = protein
                           organism = synthetic construct
SEQUENCE: 11
GLYGVDY                                                                   7

SEQ ID NO: 12              moltype = AA   length = 11
FEATURE                    Location/Qualifiers
REGION                     1..11
                           note = synthetic
source                     1..11
                           mol_type = protein
                           organism = synthetic construct
SEQUENCE: 12
KASENVVTYV S                                                             11

SEQ ID NO: 13              moltype = AA   length = 7
FEATURE                    Location/Qualifiers
REGION                     1..7
                           note = synthetic
source                     1..7
                           mol_type = protein
                           organism = synthetic construct
SEQUENCE: 13
GASNRYT                                                                   7

SEQ ID NO: 14              moltype = AA   length = 9
FEATURE                    Location/Qualifiers
REGION                     1..9
                           note = synthetic
source                     1..9
                           mol_type = protein
                           organism = synthetic construct
SEQUENCE: 14
GQSYTYPYT                                                                 9

SEQ ID NO: 15              moltype = AA   length = 118
FEATURE                    Location/Qualifiers
REGION                     1..118
                           note = synthetic
source                     1..118
                           mol_type = protein
                           organism = synthetic construct
SEQUENCE: 15
QAQIQLVQSG PELKKPGETV KISCKASGYT FTTYGMSWVK QAPGKGLKWM GWIHTYSGVP         60
TYADDFKGRF AFSLETSAST AFLQINNLKN EDTATYFCAR GLYGVDYWGQ GTTLTVSS          118

SEQ ID NO: 16              moltype = AA   length = 107
FEATURE                    Location/Qualifiers
REGION                     1..107
                           note = synthetic
source                     1..107
                           mol_type = protein
                           organism = synthetic construct
SEQUENCE: 16
NIVMTQSPKS MSMSVGERVT LSCKASENVV TYVSWYQQKP EQSPKLLIYG ASNRYTGVPD         60
RFTGSGSATD FTLTISSVQA EDLADYHCGQ SYTYPYTFGG GTTLEIK                     107

SEQ ID NO: 17              moltype = DNA   length = 21
FEATURE                    Location/Qualifiers
misc_feature               1..21
                           note = synthetic
source                     1..21
                           mol_type = other DNA
                           organism = synthetic construct
SEQUENCE: 17
accctgggaa tgggagtggg a                                                  21

SEQ ID NO: 18              moltype = DNA   length = 48
FEATURE                    Location/Qualifiers
misc_feature               1..48
                           note = synthetic
source                     1..48
                           mol_type = other DNA
                           organism = synthetic construct
```

```
SEQUENCE: 18
cacatctggt gggacgccga taagtactat aatcctgctc tgaagtcc            48

SEQ ID NO: 19          moltype = DNA   length = 27
FEATURE                Location/Qualifiers
misc_feature           1..27
                       note = synthetic
source                 1..27
                       mol_type = other DNA
                       organism = synthetic construct
SEQUENCE: 19
atgacaggca cccggtattt cgacgtg                                   27

SEQ ID NO: 20          moltype = DNA   length = 33
FEATURE                Location/Qualifiers
misc_feature           1..33
                       note = synthetic
source                 1..33
                       mol_type = other DNA
                       organism = synthetic construct
SEQUENCE: 20
aaggcctccc agaacatcaa taagtttatc gct                            33

SEQ ID NO: 21          moltype = DNA   length = 21
FEATURE                Location/Qualifiers
misc_feature           1..21
                       note = synthetic
source                 1..21
                       mol_type = other DNA
                       organism = synthetic construct
SEQUENCE: 21
tataccagca cactgcagcc c                                         21

SEQ ID NO: 22          moltype = DNA   length = 24
FEATURE                Location/Qualifiers
misc_feature           1..24
                       note = synthetic
source                 1..24
                       mol_type = other DNA
                       organism = synthetic construct
SEQUENCE: 22
ctgcagtatg gcgtgctgtg gacc                                      24

SEQ ID NO: 23          moltype = DNA   length = 357
FEATURE                Location/Qualifiers
misc_feature           1..357
                       note = synthetic
source                 1..357
                       mol_type = other DNA
                       organism = synthetic construct
SEQUENCE: 23
caggtgacac tgaaggagtc tggcccaacc ctggtgaagc ccacccagac actgaccctg    60
acatgtacct tctctggctt ttctctgtcc accctgggaa tgggagtggg atggatcaga   120
cagccacctg gcaaggccct ggagtggctg gctcacatct ggtgggacgc cgataagtac   180
tataatcctg ctctgaagtc ccgcctgaca atcaccaagc acacaagcaa gaaccaggtg   240
gtgctgacaa tgaccaatat ggacccagtg gatacagcac cctactattg cgctaggatg   300
acaggcaccc ggtatttcga cgtgtggggc cagggcacca cagtgaccgt gtccagc      357

SEQ ID NO: 24          moltype = DNA   length = 318
FEATURE                Location/Qualifiers
misc_feature           1..318
                       note = synthetic
source                 1..318
                       mol_type = other DNA
                       organism = synthetic construct
SEQUENCE: 24
gacatccaga tgacacagag cccatccagc ctgtccgcct ccgtgggcga cagggtgacc    60
atcacatgca aggcctccca gaacatcaat aagtttatcg cttggtacca gcagaagcca   120
ggcaaggtgc ccaagctgct gatccactat accagcacac tgcagcccgg cgtgccttct   180
aggttctccg gcagcggctc tggctccgac tacaccctga caatctcttc cctgcagcct   240
gaggatgtgg ccacctacta ttgtctgcag tatggcgtgc tgtggacctt tggcggcggc   300
acaaaggtgg agatcaag                                                 318

SEQ ID NO: 25          moltype = AA    length = 119
FEATURE                Location/Qualifiers
REGION                 1..119
                       note = synthetic
source                 1..119
                       mol_type = protein
```

```
                        organism = synthetic construct
SEQUENCE: 25
QVTLKESGPT LVKPTQTLTL TCTFSGFSLS TLGMGVGWIR QPPGKALEWL AHIWWDADKY      60
YNPALKSRLT ITKDTSKNQV VLTMTNMDPV DTATYYCARM TGTRYFDVWG QGTTVTVSS      119

SEQ ID NO: 26           moltype = AA   length = 106
FEATURE                 Location/Qualifiers
REGION                  1..106
                        note = synthetic
source                  1..106
                        mol_type = protein
                        organism = synthetic construct
SEQUENCE: 26
DIQMTQSPSS LSASVGDRVT ITCKASQNIN KFIAWYQQKP GKVPKLLIHY TSTLQPGVPS      60
RFSGSGSGSD YTLTISSLQP EDVATYYCLQ YGVLWTFGGG TKVEIK                    106

SEQ ID NO: 27           moltype = DNA   length = 318
FEATURE                 Location/Qualifiers
misc_feature            1..318
                        note = synthetic
source                  1..318
                        mol_type = other DNA
                        organism = synthetic construct
SEQUENCE: 27
gacatccaga tgacacagag cccatccagc ctgtccgcct ccgtgggcga tcgggtgacc      60
atcacatgca aggcctccca gaacatcaat aagtttatcg cttggtacca gcacaagcca    120
ggcaaggtgc ccaagctgct gatccattat accagcacac tgcagcccgg cgtgccttct    180
aggttctccg gcagcggctc tggctccgac tacaccctga caatctcttc cctgcagcct    240
gaggatgtgg ccacctacta ttgtctgcag tatggcgtgc tgtggacctt tggcggcggc    300
acaaaggtgg agatcaag                                                  318

SEQ ID NO: 28           moltype = AA   length = 106
FEATURE                 Location/Qualifiers
REGION                  1..106
                        note = synthetic
source                  1..106
                        mol_type = protein
                        organism = synthetic construct
SEQUENCE: 28
DIQMTQSPSS LSASVGDRVT ITCKASQNIN KFIAWYQHKP GKVPKLLIHY TSTLQPGVPS      60
RFSGSGSGSD YTLTISSLQP EDVATYYCLQ YGVLWTFGGG TKVEIK                    106

SEQ ID NO: 29           moltype = DNA   length = 15
FEATURE                 Location/Qualifiers
misc_feature            1..15
                        note = synthetic
source                  1..15
                        mol_type = other DNA
                        organism = synthetic construct
SEQUENCE: 29
acatatggca tgtct                                                       15

SEQ ID NO: 30           moltype = DNA   length = 51
FEATURE                 Location/Qualifiers
misc_feature            1..51
                        note = synthetic
source                  1..51
                        mol_type = other DNA
                        organism = synthetic construct
SEQUENCE: 30
tggattcaca catactccgg cgtgcctacc tatgccgacg acttcaaggg c                51

SEQ ID NO: 31           moltype = DNA   length = 21
FEATURE                 Location/Qualifiers
misc_feature            1..21
                        note = synthetic
source                  1..21
                        mol_type = other DNA
                        organism = synthetic construct
SEQUENCE: 31
ggcctgtacg gcgtggatta t                                                21

SEQ ID NO: 32           moltype = DNA   length = 33
FEATURE                 Location/Qualifiers
misc_feature            1..33
                        note = synthetic
source                  1..33
                        mol_type = other DNA
                        organism = synthetic construct
```

```
SEQUENCE: 32
aaggcttctg agaacgtggt gacatacgtg tcc                                 33

SEQ ID NO: 33           moltype = DNA   length = 21
FEATURE                 Location/Qualifiers
misc_feature            1..21
                        note = synthetic
source                  1..21
                        mol_type = other DNA
                        organism = synthetic construct
SEQUENCE: 33
ggcgcttcca ataggtacac c                                              21

SEQ ID NO: 34           moltype = DNA   length = 27
FEATURE                 Location/Qualifiers
misc_feature            1..27
                        note = synthetic
source                  1..27
                        mol_type = other DNA
                        organism = synthetic construct
SEQUENCE: 34
ggccagtctt acacctatcc ttacaca                                        27

SEQ ID NO: 35           moltype = DNA   length = 348
FEATURE                 Location/Qualifiers
misc_feature            1..348
                        note = synthetic
source                  1..348
                        mol_type = other DNA
                        organism = synthetic construct
SEQUENCE: 35
cagatccagc tggtgcagag cggagctgag gtgaagaagc caggagcttc cgtgaaggtg    60
agctgtaagg cctctggcta cacattcacc acatatggca tgtcttgggt gagacaggct   120
ccaggacagg gactggagtg gatgggctgg attcacacat actccggcgt gcctacctat   180
gccgacgact tcaagggccg cttcgctttt acactgacaa cctctacatc caccgcctat   240
atggagctga ggagcctgcg gtctgacgat accgccgtgt actattgcgc tagggccctg   300
tacggcgtgg attattgggg ccagggcaca ctggtgaccg tgtccagc                348

SEQ ID NO: 36           moltype = DNA   length = 321
FEATURE                 Location/Qualifiers
misc_feature            1..321
                        note = synthetic
source                  1..321
                        mol_type = other DNA
                        organism = synthetic construct
SEQUENCE: 36
gagatcgtga tgacccagag cccagctaca ctgtctctgt ccccaggaga gagggccacc    60
ctgagctgca aggcttctga gaacgtggtg acatacgtgt cctggtacca gcagaagcca   120
ggacaggctc ctaggctgct gatctatggc gcttccaata ggtacaccgg catcccagct   180
cggtttagcg gctctggctc cgctacagac ttcaccctga caatctccag cctgcagccc   240
gaggattttg ccgtgtacta ttgtggccag tcttacacct atcctacac attcggccag   300
ggcacaaagc tggagatcaa g                                             321

SEQ ID NO: 37           moltype = AA   length = 116
FEATURE                 Location/Qualifiers
REGION                  1..116
                        note = synthetic
source                  1..116
                        mol_type = protein
                        organism = synthetic construct
SEQUENCE: 37
QIQLVQSGAE VKKPGASVKV SCKASGYTFT TYGMSWVRQA PGQGLEWMGW IHTYSGVPTY    60
ADDFKGRFAF TLDTSTSTAY MELRSLRSDD TAVYYCARGL YGVDYWGQGT LVTVSS       116

SEQ ID NO: 38           moltype = AA   length = 107
FEATURE                 Location/Qualifiers
REGION                  1..107
                        note = synthetic
source                  1..107
                        mol_type = protein
                        organism = synthetic construct
SEQUENCE: 38
EIVMTQSPAT LSLSPGERAT LSCKASENVV TYVSWYQQKP GQAPRLLIYG ASNRYTGIPA    60
RFSGSGSATD FTLTISSLQP EDFAVYYCGQ SYTYPYTFGQ GTKLEIK                 107

SEQ ID NO: 39           moltype = DNA   length = 993
FEATURE                 Location/Qualifiers
misc_feature            1..993
                        note = synthetic
```

```
source                        1..993
                              mol_type = other DNA
                              organism = synthetic construct
SEQUENCE: 39
gccagcacca aagggaccatc cgtgttccca ctggcccct ccagcaagtc caccagcgga    60
ggaacagccg ctctgggatg cctggtgaag gactacttcc cagagcccgt gacagtgagc   120
tggaactctg gcgccctgac cagcggagtg cacacatttc cgccgtgct ccagtcttcc    180
ggcctgtact ctctgagctc tgtggtgacc gtgcccca gctctctggg cacccagaca     240
tatatctgca acgtgaatca caagccaagc aatacaagg tggacaagaa ggtggagcc     300
aagtcttgtg ataagaccca tacatgcccc ccttgtcctg ctccagagct gctgggagga   360
ccaagcgtgt tcctgtttcc acccaagcct aaggacaccc tgatgatctc caggaccccc   420
gaggtgacat gcgtggtggt ggacgtgagc cacgaggacc ccgaggtgaa gtttaactgg   480
tacgtggatg gcgtggaggt gcataatgct aagaccaagc ctagggagga gcagtacaac   540
tctacctatc gggtggtgtc cgtgctgaca gtgctgcacc aggactggct gaacggcaag   600
gagtataagt gcaaggtgtc taataaggcc ctgcccgctc ctatcgagaa gaccatctcc   660
aaggccaagg gccagcctag agagccacag gtgtacacac tgcctccatc tcgcgacgag   720
ctgaccaaga accaggtgtc cctgacatgt ctggtgaagg cttctatcc ttccgacatc    780
gctgtggagt gggagagcaa cggccagcca gagaacaatt acaagaccac acccctgtg    840
ctggactccg atggcagctt ctttctgtat agcaagctga ccgtggataa gtccaggtgg   900
cagcagggca acgtgttttc ttgctccgtg atgcatgagg ctctgcacaa tcattataca   960
cagaagagcc tgtctctgtc ccctggcaag taa                                993

SEQ ID NO: 40             moltype = AA  length = 330
FEATURE                   Location/Qualifiers
REGION                    1..330
                          note = synthetic
source                    1..330
                          mol_type = protein
                          organism = synthetic construct
SEQUENCE: 40
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 41             moltype = DNA  length = 324
FEATURE                   Location/Qualifiers
misc_feature              1..324
                          note = synthetic
source                    1..324
                          mol_type = other DNA
                          organism = synthetic construct
SEQUENCE: 41
cggacggtgg ctgcaccatc tgtcttcatc ttcccgccat ctgatgagca gttgaaatct    60
ggaactgcct ctgttgtgtg cctgctgaat aacttctacc ccagagagc caaagtgcag   120
tggaaggtgg acaacgccct gcagagcgga aacagccagg aaagcgtgac agagcaggat   180
tccaaggatt ccacatacag cctgagcagc acactgacac tgtccaaggc cgactacgag   240
aagcacaagg tgtacgcctg cgaagtgaca caccagggac tgtcctcccc tgtgacaaag   300
agcttcaaca gagaggaatg ctaa                                          324

SEQ ID NO: 42             moltype = AA  length = 107
FEATURE                   Location/Qualifiers
REGION                    1..107
                          note = synthetic
source                    1..107
                          mol_type = protein
                          organism = synthetic construct
SEQUENCE: 42
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 43             moltype = AA  length = 448
FEATURE                   Location/Qualifiers
REGION                    1..448
                          note = synthetic
source                    1..448
                          mol_type = protein
                          organism = synthetic construct
SEQUENCE: 43
QVQLVESGGG AVQPGRSLRL SCAASGFTFS SYGMHWVRQA PGKGLEWVAV ILYDGSDKFY    60
ADSVKGRFTI SRDNSKNTLY LQMNSLRAED TAVYYCAKVA VAGTHFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                      448
```

```
SEQ ID NO: 44            moltype = AA  length = 214
FEATURE                  Location/Qualifiers
REGION                   1..214
                         note = synthetic
source                   1..214
                         mol_type = protein
                         organism = synthetic construct
SEQUENCE: 44
DIQMTQSPSS LSASVGDRVT ITCRASQGIR NDLGWYQQKP GKAPKLLIYA ASSLQSGVPS      60
RFSGSGSGTD FTLTISSLQP EDFATYYCQQ LNSYPPTFGG GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 45            moltype = AA  length = 479
FEATURE                  Location/Qualifiers
REGION                   1..479
                         note = synthetic
source                   1..479
                         mol_type = protein
                         organism = synthetic construct
SEQUENCE: 45
MAPVAVWAAL AVGLELWAAA HALPAQVAFT PYAPEPGSTC RLREYYDQTA QMCCSKCSPG      60
QHAKVFCTKT SDTVCDSCED STYTQLWNWV PECLSCGSRC SSDQVETQAC TREQNRICTC     120
RPGWYCALSK QEGCRLCAPL RKCRPGFGVA RPGTETSDVV CKPCAPGTFS NTTSSTDICR     180
PHQICNVVAI PGNASMDAVC TSTSPTRSMA PGAVHLPQPV STRSQHTQPT PEPSTAPSTS     240
FLLPMGPSPP AEGSTGDGCK PCICTVPEVS SVFIFPPKPK DVLTITLTPK VTCVVVAISK     300
DDPEVQFSWF VDDVEVHTAQ TQPREEQFNS TFRSVSELPI MHQDWLNGKE FKCRVNSAAF     360
PAPIEKTISK TKGRPKAPQV YTIPPPKEQM AKDKVSLTCM ITDFFPEDIT VEWQWNGQPA     420
ENYKNTQPIM NTNGSYFVYS KLNVQKSNWE AGNTFTCSVL HEGLHNHHTE KSLSHSPGK      479

SEQ ID NO: 46            moltype = AA  length = 484
FEATURE                  Location/Qualifiers
REGION                   1..484
                         note = synthetic
source                   1..484
                         mol_type = protein
                         organism = synthetic construct
SEQUENCE: 46
MAPVAVWAAL AVGLELWAAA HALPAQVAFT PYAPEPGSTC RLREYYDQTA QMCCSKCSPG      60
QHAKVFCTKT SDTVCDSCED STYTQLWNWV PECLSCGSRC SSDQVETQAC TREQNRICTC     120
RPGWYCALSK QEGCRLCAPL RKCRPGFGVA RPGTETSDVV CKPCAPGTFS NTTSSTDICR     180
PHQICNVVAI PGNASMDAVC TSTSPTRSMA PGAVHLPQPV STRSQHTQPT PEPSTAPSTS     240
FLLPMGPSPP AEGSTGDDKT HTCPPCPAPE LLGGPSVFLF PPKPKDTLMI SRTPEVTCVV     300
VDVSHEDPEV KFNWYVDGVE VHNAKTKPRE EQYNSTYRVV SVLTVLHQDW LNGKEYKCKV     360
SNKALPAPIE KTISKAKGQP REPQVYTLPP SREEMTKNQV SLTCLVKGFY PSDIAVEWES     420
NGQPENNYKT TPPVLDSDGS FFLYSKLTVD KSRWQQGNVF SCSVMHEALH NHYTQKSLSL     480
SPGK                                                                  484

SEQ ID NO: 47            moltype = AA  length = 484
FEATURE                  Location/Qualifiers
REGION                   1..484
                         note = synthetic
source                   1..484
                         mol_type = protein
                         organism = synthetic construct
SEQUENCE: 47
MAPAAVWAAL AVGLELWAAG HALPAQVAFT PYAPEPGGTC RLREYYDQTA QMCCSKCPPG      60
QHAKVFCTKT SDTVCDSCED STYTQLWNWV PECLSCGSRC SSDQVETQAC TREQNRICTC     120
RPGWYCALSK QEGCRLCAQL RKCRPGFGVA RPGTETSDVV CKPCAPGTFS NTTSSTDICR     180
PHQICHVVAI PGNASMDAVC TSTSPTRSMA PGAVHLPQPV STRSQHTQPT PAPSTAPGTS     240
FLLPVGPSPP AEGSTGDDKT HTCPPCPAPE LLGGPSVFLF PPKPKDTLMI SRTPEVTCVV     300
VDVSHEDPEV KFNWYVDGVE VHNAKTKPRE EQYNSTYRVV SVLTVLHQDW LNGKEYKCKV     360
SNKALPAPIE KTISKAKGQP REPQVYTLPP SREEMTKNQV SLTCLVKGFY PSDIAVEWES     420
NGQPENNYKT TPPVLDSDGS FFLYSKLTVD KSRWQQGNVF SCSVMHEALH NHYTQKSLSL     480
SPGK                                                                  484

SEQ ID NO: 48            moltype = AA  length = 461
FEATURE                  Location/Qualifiers
REGION                   1..461
                         note = synthetic
source                   1..461
                         mol_type = protein
                         organism = synthetic construct
SEQUENCE: 48
MAPVAVWAAL AVGLELWAAA HALPAQVAFT PYAPEPGSTC RLREYYDQTA QMCCSKCSPG      60
QHAKVFCTKT SDTVCDSCED STYTQLWNWV PECLSCGSRC SSDQVETQAC TREQNRICTC     120
RPGWYCALSK QEGCRLCAPL RKCRPGFGVA RPGTETSDVV CKPCAPGTFS NTTSSTDICR     180
PHQICNVVAI PGNASMDAVC TSTSPTRSMA PGAVHLPQPV STRSQHTQPT PEPSTAPSTS     240
```

```
FLLPMGPSPP AEGSTGDFAL PVGLIVGVTA LGLLIIGVVN CVIMTQVKKK PLCLQREAKV    300
PHLPADKARG TQGPEQQHLL ITAPSSSSSS LESSASALDR RAPTRNQPQA PGVEASGAGE    360
ARASTGSSDS SPGGHGTQVN VTCIVNVCSS SDHSSQCSSQ ASSTMGDTDS SPSESPKDEQ    420
VPFSKEECAF RSQLETPETL LGSTEEKPLP LGVPDAGMKP S                        461

SEQ ID NO: 49           moltype = AA  length = 283
FEATURE                 Location/Qualifiers
REGION                  1..283
                        note = synthetic
source                  1..283
                        mol_type = protein
                        organism = synthetic construct
SEQUENCE: 49
MAPAAVWAAL AVGLELWAAG HALPAQVAFT PYAPEPGGTC RLREYYDQTA QMCCSKCPPG     60
QHAKVFCTKT SDTVCDSCED STYTQLWNWV PECLSCGSRC SSDQVETQAC TREQNRICTC    120
RPGWYCALSK QEGCRLCAQL RKCRPGFGVA RPGTETSDVV CKPCAPGTFS NTTSSTDICR    180
PHQICHVVAI PGNASMDAVC TSTSPTRSMA PGAVHLPQPV STRSQHTQPT PAPSTAPGTS    240
FLLPVGPSPP AEGSTGDIVL PVGLIVGVTA LGLLIIGVVN CVI                      283

SEQ ID NO: 50           moltype = AA  length = 257
FEATURE                 Location/Qualifiers
REGION                  1..257
                        note = synthetic
source                  1..257
                        mol_type = protein
                        organism = synthetic construct
SEQUENCE: 50
MAPVAVWAAL AVGLELWAAA HALPAQVAFT PYAPEPGSTC RLREYYDQTA QMCCSKCSPG     60
QHAKVFCTKT SDTVCDSCED STYTQLWNWV PECLSCGSRC SSDQVETQAC TREQNRICTC    120
RPGWYCALSK QEGCRLCAPL RKCRPGFGVA RPGTETSDVV CKPCAPGTFS NTTSSTDICR    180
PHQICNVVAI PGNASMDAVC TSTSPTRSMA PGAVHLPQPV STRSQHTQPT PEPSTAPSTS    240
FLLPMGPSPP AEGSTGD                                                   257

SEQ ID NO: 51           moltype = AA  length = 258
FEATURE                 Location/Qualifiers
REGION                  1..258
                        note = synthetic
source                  1..258
                        mol_type = protein
                        organism = synthetic construct
SEQUENCE: 51
MAPAALWVAL VFELQLWATG HTVPAQVVLT PYKPEPGYEC QISQEYYDRK AQMCCAKCPP     60
GQYVKHFCNK TSDTVCADCE ASMYTQVWNQ FRTCLSCSSS CTTDQVEIRA CTKQQNRVCA    120
CEAGRYCALK THSGSCRQCM RLSKCGPGFG VASSRAPNGN VLCKACAPGT FSDTTSSTDV    180
CRPHRICSIL AIPGNASTDA VCAPESPTLS AIPRTLYVSQ PEPTRSQPLD QEPGPSQTPS    240
ILTSLGSTPI IEQSTKGG                                                  258

SEQ ID NO: 52           moltype = AA  length = 481
FEATURE                 Location/Qualifiers
REGION                  1..481
                        note = synthetic
source                  1..481
                        mol_type = protein
                        organism = synthetic construct
SEQUENCE: 52
MYLGLNCVFI VFLLKGVQSV PAQVVLTPYK PEPGYTCRLR EYYDQTAQMC CSKCSPGQHA     60
KVFCTKTSDT VCDDCEASMY TQVWNQFRTC LSCSSSCTTD QVEIRACTKQ QNRVCACEAG    120
RYCALKTHSG SCRQCMRLSK CGPGFGVASS RAPNGNVLCK ACAPGTFSDT TSSTDVCRPH    180
RICSILAIPG NASTDAVCAP ESPTLSAIPR TLYVSQPEPT RSQPLDQEPG PSQTPSILTS    240
LGSTPIIEQS TKGGDKTHTC PPCPAPELLG GPSVFLFPPK PKDTLMISRT PEVTCVVVDV    300
SHEDPEVKFN WYVDGVEVHN AKTKPREEQY NSTYRVVSVL TVLHQDWLNG KEYKCKVSNK    360
ALPAPIEKTI SKAKGQPREP QVYTLPPSRD ELTKNQVSLT CLVKGFYPSD IAVEWESNGQ    420
PENNYKTTPP VLDSDGSFFL YSKLTVDKSR WQQGNVFSCS VMHEALHNHY TQKSLSLSPG    480
K                                                                    481

SEQ ID NO: 53           moltype = AA  length = 482
FEATURE                 Location/Qualifiers
REGION                  1..482
                        note = synthetic
source                  1..482
                        mol_type = protein
                        organism = synthetic construct
SEQUENCE: 53
MYLGLNCVFI VFLLKGVQSV PAQVVLTPYK PEPGYECQIS QEYYDRKAQM CCAKCPPGQY     60
VKHFCNKTSD TVCASCEDST YTQLWNWVPE CLSCGSRCSS DQVETQACTR EQNRICACEA    120
GRYCALKTHS GSCRQCMRLS KCGPGFGVAS SRAPNGNVLC KACAPGTFSD TTSSTDVCRP    180
HRICSILAIP GNASTDAVCA PESPTLSAIP RTLYVSQPEP TRSQPLDQEP GPSQTPSILT    240
SLGSTPIIEQ STKGGDKTHT CPPCPAPELL GGPSVFLFPP KPKDTLMISR TPEVTCVVVD    300
VSHEDPEVKF NWYVDGVEVH NAKTKPREEQ YNSTYRVVSV LTVLHQDWLN GKEYKCKVSN    360
```

```
KALPAPIEKT ISKAKGQPRE PQVYTLPPSR DELTKNQVSL TCLVKGFYPS DIAVEWESNG    420
QPENNYKTTP PVLDSDGSFF LYSKLTVDKS RWQQGNVFSC SVMHEALHNH YTQKSLSLSP    480
GK                                                                  482

SEQ ID NO: 54           moltype = AA  length = 481
FEATURE                 Location/Qualifiers
REGION                  1..481
                        note = synthetic
source                  1..481
                        mol_type = protein
                        organism = synthetic construct
SEQUENCE: 54
MYLGLNCVFI VFLLKGVQSV PAQVVLTPYK PEPGYECQIS QEYYDRKAQM CCAKCPPGQY     60
VKHFCNKTSD TVCADCEASM YTQVWNQFRT CLSCSSSCTT DQVEIRACTK QQNRVCTCRP    120
GWYCALSKQE GCRLCAPLRK CRPGFGVARP GTETSDVVCK ACAPGTFSDT TSSTDVCRPH    180
RICSILAIPG NASTDAVCAP ESPTLSAIPR TLYVSQPEPT RSQPLDQEPG PSQTPSILTS    240
LGSTPIIEQS TKGGDKTHTC PPCPAPELLG GPSVFLFPPK PKDTLMISRT PEVTCVVVDV    300
SHEDPEVKFN WYVDGVEVHN AKTKPREEQY NSTYRVVSVL TVLHQDWLNG KEYKCKVSNK    360
ALPAPIEKTI SKAKGQPREP QVYTLPPSRD ELTKNQVSLT CLVKGFYPSD IAVEWESNGQ    420
PENNYKTTPP VLDSDGSFFL YSKLTVDKSR WQQGNVFSCS VMHEALHNHY TQKSLSLSPG    480
K                                                                   481

SEQ ID NO: 55           moltype = AA  length = 482
FEATURE                 Location/Qualifiers
REGION                  1..482
                        note = synthetic
source                  1..482
                        mol_type = protein
                        organism = synthetic construct
SEQUENCE: 55
MYLGLNCVFI VFLLKGVQSV PAQVVLTPYK PEPGYECQIS QEYYDRKAQM CCAKCPPGQY     60
VKHFCNKTSD TVCADCEASM YTQVWNQFRT CLSCSSSCTT DQVEIRACTK QQNRVCACEA    120
GRYCALKTHS GSCRQCMRLS KCGPGFGVAS SRAPNGNVLC KPCAPGTFSN TTSSTDICRP    180
HQICNVVAIP GNASMDAVCT PESPTLSAIP RTLYVSQPEP TRSQPLDQEP GPSQTPSILT    240
SLGSTPIIEQ STKGGDKTHT CPPCPAPELL GGPSVFLFPP KPKDTLMISR TPEVTCVVVD    300
VSHEDPEVKF NWYVDGVEVH NAKTKPREEQ YNSTYRVVSV LTVLHQDWLN GKEYKCKVSN    360
KALPAPIEKT ISKAKGQPRE PQVYTLPPSR DELTKNQVSL TCLVKGFYPS DIAVEWESNG    420
QPENNYKTTP PVLDSDGSFF LYSKLTVDKS RWQQGNVFSC SVMHEALHNH YTQKSLSLSP    480
GK                                                                  482

SEQ ID NO: 56           moltype = AA  length = 482
FEATURE                 Location/Qualifiers
REGION                  1..482
                        note = synthetic
source                  1..482
                        mol_type = protein
                        organism = synthetic construct
SEQUENCE: 56
MYLGLNCVFI VFLLKGVQSV PAQVVLTPYK PEPGYECQIS QEYYDRKAQM CCAKCPPGQH     60
AKVFCTKTSD TVCDSCEDST YTQLWNWVPE CLSCSSSCTT DQVEIRACTK QQNRVCACEA    120
GRYCALKTHS GSCRQCMRLS KCGPGFGVAS SRAPNGNVLC KACAPGTFSD TTSSTDVCRP    180
HRICSILAIP GNASTDAVCA PESPTLSAIP RTLYVSQPEP TRSQPLDQEP GPSQTPSILT    240
SLGSTPIIEQ STKGGDKTHT CPPCPAPELL GGPSVFLFPP KPKDTLMISR TPEVTCVVVD    300
VSHEDPEVKF NWYVDGVEVH NAKTKPREEQ YNSTYRVVSV LTVLHQDWLN GKEYKCKVSN    360
KALPAPIEKT ISKAKGQPRE PQVYTLPPSR DELTKNQVSL TCLVKGFYPS DIAVEWESNG    420
QPENNYKTTP PVLDSDGSFF LYSKLTVDKS RWQQGNVFSC SVMHEALHNH YTQKSLSLSP    480
GK                                                                  482

SEQ ID NO: 57           moltype = AA  length = 481
FEATURE                 Location/Qualifiers
REGION                  1..481
                        note = synthetic
source                  1..481
                        mol_type = protein
                        organism = synthetic construct
SEQUENCE: 57
MYLGLNCVFI VFLLKGVQSV PAQVVLTPYK PEPGYECQIS QEYYDRKAQM CCAKCPPGQY     60
VKHFCNKTSD TVCADCEASM YTQVWNQFRT CLSCGSRCSS DQVETQACTR EQNRICTCRP    120
GWYCALSKQE GCRLCAPLRK CGPGFGVASS RAPNGNVLCK ACAPGTFSDT TSSTDVCRPH    180
RICSILAIPG NASTDAVCAP ESPTLSAIPR TLYVSQPEPT RSQPLDQEPG PSQTPSILTS    240
LGSTPIIEQS TKGGDKTHTC PPCPAPELLG GPSVFLFPPK PKDTLMISRT PEVTCVVVDV    300
SHEDPEVKFN WYVDGVEVHN AKTKPREEQY NSTYRVVSVL TVLHQDWLNG KEYKCKVSNK    360
ALPAPIEKTI SKAKGQPREP QVYTLPPSRD ELTKNQVSLT CLVKGFYPSD IAVEWESNGQ    420
PENNYKTTPP VLDSDGSFFL YSKLTVDKSR WQQGNVFSCS VMHEALHNHY TQKSLSLSPG    480
K                                                                   481

SEQ ID NO: 58           moltype = AA  length = 481
FEATURE                 Location/Qualifiers
REGION                  1..481
```

```
                         note         = synthetic
source                   1..481
                         mol_type     = protein
                         organism     = synthetic construct
SEQUENCE: 58
MYLGLNCVFI VFLLKGVQSL PAQVAFTPYA PEPGSTCRLR EYYDQTAQMC CAKCPPGQYV    60
KHFCNKTSDT VCADCEASMY TQVWNQFRTC LSCSSSCTTD QVEIRACTKQ QNRVCACEAG   120
RYCALKTHSG SCRQCMRLSK CGPGFGVASS RAPNGNVLCK ACAPGTFSDT TSSTDVCRPH   180
RICSILAIPG NASTDAVCAP ESPTLSAIPR TLYVSQPEPT RSQPLDQEPG PSQTPSILTS   240
LGSTPIIEQS TKGGDKTHTC PPCPAPELLG GPSVFLFPPK PKDTLMISRT PEVTCVVVDV   300
SHEDPEVKFN WYVDGVEVHN AKTKPREEQY NSTYRVVSVL TVLHQDWLNG KEYKCKVSNK   360
ALPAPIEKTI SKAKGQPREP QVYTLPPSRD ELTKNQVSLT CLVKGFYPSD IAVEWESNGQ   420
PENNYKTTPP VLDSDGSFFL YSKLTVDKSR WQQGNVFSCS VMHEALHNHY TQKSLSLSPG   480
K                                                                  481

SEQ ID NO: 59            moltype = AA   length = 481
FEATURE                  Location/Qualifiers
REGION                   1..481
                         note         = synthetic
source                   1..481
                         mol_type     = protein
                         organism     = synthetic construct
SEQUENCE: 59
MYLGLNCVFI VFLLKGVQSL PAQVAFTPYA PEPGSTCRLR EYYDQTAQMC CSKCSPGQHA    60
KVFCTKTSDT VCDDCEASMY TQVWNQFRTC LSCSSSCTTD QVEIRACTKQ QNRVCACEAG   120
RYCALKTHSG SCRQCMRLSK CGPGFGVASS RAPNGNVLCK ACAPGTFSDT TSSTDVCRPH   180
RICSILAIPG NASTDAVCAP ESPTLSAIPR TLYVSQPEPT RSQPLDQEPG PSQTPSILTS   240
LGSTPIIEQS TKGGDKTHTC PPCPAPELLG GPSVFLFPPK PKDTLMISRT PEVTCVVVDV   300
SHEDPEVKFN WYVDGVEVHN AKTKPREEQY NSTYRVVSVL TVLHQDWLNG KEYKCKVSNK   360
ALPAPIEKTI SKAKGQPREP QVYTLPPSRD ELTKNQVSLT CLVKGFYPSD IAVEWESNGQ   420
PENNYKTTPP VLDSDGSFFL YSKLTVDKSR WQQGNVFSCS VMHEALHNHY TQKSLSLSPG   480
K                                                                  481

SEQ ID NO: 60            moltype = AA   length = 481
FEATURE                  Location/Qualifiers
REGION                   1..481
                         note         = synthetic
source                   1..481
                         mol_type     = protein
                         organism     = synthetic construct
SEQUENCE: 60
MYLGLNCVFI VFLLKGVQSV PAQVVLTPYK PEPGYTCRLR EYYDQTAQMC CAKCPPGQYV    60
KHFCNKTSDT VCADCEASMY TQVWNQFRTC LSCSSSCTTD QVEIRACTKQ QNRVCACEAG   120
RYCALKTHSG SCRQCMRLSK CGPGFGVASS RAPNGNVLCK ACAPGTFSDT TSSTDVCRPH   180
RICSILAIPG NASTDAVCAP ESPTLSAIPR TLYVSQPEPT RSQPLDQEPG PSQTPSILTS   240
LGSTPIIEQS TKGGDKTHTC PPCPAPELLG GPSVFLFPPK PKDTLMISRT PEVTCVVVDV   300
SHEDPEVKFN WYVDGVEVHN AKTKPREEQY NSTYRVVSVL TVLHQDWLNG KEYKCKVSNK   360
ALPAPIEKTI SKAKGQPREP QVYTLPPSRD ELTKNQVSLT CLVKGFYPSD IAVEWESNGQ   420
PENNYKTTPP VLDSDGSFFL YSKLTVDKSR WQQGNVFSCS VMHEALHNHY TQKSLSLSPG   480
K                                                                  481

SEQ ID NO: 61            moltype = AA   length = 482
FEATURE                  Location/Qualifiers
REGION                   1..482
                         note         = synthetic
source                   1..482
                         mol_type     = protein
                         organism     = synthetic construct
SEQUENCE: 61
MYLGLNCVFI VFLLKGVQSL PAQVAFTPYA PEPGSECQIS QEYYDRKAQM CCAKCPPGQY    60
VKHFCNKTSD TVCADCEASM YTQVWNQFRT CLSCSSSCTT DQVEIRACTK QQNRVCACEA   120
GRYCALKTHS GSCRQCMRLS KCGPGFGVAS SRAPNGNVLC KACAPGTFSD TTSSTDVCRP   180
HRICSILAIP GNASTDAVCA PESPTLSAIP RTLYVSQPEP TRSQPLDQEP GPSQTPSILT   240
SLGSTPIIEQ STKGGDKTHT CPPCPAPELL GGPSVFLFPP KPKDTLMISR TPEVTCVVVD   300
VSHEDPEVKF NWYVDGVEVH NAKTKPREEQ YNSTYRVVSV LTVLHQDWLN GKEYKCKVSN   360
KALPAPIEKT ISKAKGQPRE PQVYTLPPSR DELTKNQVSL TCLVKGFYPS DIAVEWESNG   420
QPENNYKTTP PVLDSDGSFF LYSKLTVDKS RWQQGNVFSC SVMHEALHNH YTQKSLSLSP   480
GK                                                                 482

SEQ ID NO: 62            moltype = AA   length = 484
FEATURE                  Location/Qualifiers
REGION                   1..484
                         note         = synthetic
source                   1..484
                         mol_type     = protein
                         organism     = synthetic construct
SEQUENCE: 62
MAPVAVWAAL AVGLELWAAA HALPAQVAFT PYAPEPGSTC RLREYYDQTA QMCCSKCSPG    60
QHAKVFCTKT SDTVCDSCED STYTQLWNWV PECLSCGSRC SSDQVETQAC TREQNRICAC   120
```

```
EAGRYCALKT HSGSCRQCMR LSKCGPGFGV ASSRAPNGNV LCKACAPGTF SDTTSSTDVC   180
RPHRICSILA IPGNASTDAV CAPESPTLSA IPRTLYVSQP EPTRSQPLDQ EPGPSQTPSI   240
LTSLGSTPII EQSTKGGDKT HTCPPCPAPE LLGGPSVFLF PPKPKDTLMI SRTPEVTCVV   300
VDVSHEDPEV KFNWYVDGVE VHNAKTKPRE EQYNSTYRVV SVLTVLHQDW LNGKEYKCKV   360
SNKALPAPIE KTISKAKGQP REPQVYTLPP SRDELTKNQV SLTCLVKGFY PSDIAVEWES   420
NGQPENNYKT TPPVLDSDGS FFLYSKLTVD KSRWQQGNVF SCSVMHEALH NHYTQKSLSL   480
SPGK                                                                484

SEQ ID NO: 63           moltype = AA  length = 120
FEATURE                 Location/Qualifiers
REGION                  1..120
                        note = synthetic
source                  1..120
                        mol_type = protein
                        organism = synthetic construct
SEQUENCE: 63
QVTLKESGPT LVKPTQTLTL TCTFSGFSLS TSGVGVGWIR QPPGKALEWL ALIYWDDDKR    60
YGPSLKSRLT ITKDTSKNQV VLTMTNMDPV DTATYYCAHR YYYYYGMDVW GQGTTVTVSS   120

SEQ ID NO: 64           moltype = AA  length = 119
FEATURE                 Location/Qualifiers
REGION                  1..119
                        note = synthetic
source                  1..119
                        mol_type = protein
                        organism = synthetic construct
SEQUENCE: 64
QVTLKESGPT LVKPTQTLTL TCTFSGFSLN TLGMGVGWIR QPPGKALEWL AHIWWDADKY    60
YNPALKSRLT ITKDTSKNQV VLTMTNMDPV DTATYYCARM TGTRYFDVWG QGTTVTVSS    119

SEQ ID NO: 65           moltype = AA  length = 107
FEATURE                 Location/Qualifiers
REGION                  1..107
                        note = synthetic
source                  1..107
                        mol_type = protein
                        organism = synthetic construct
SEQUENCE: 65
DIQMTQSPSS LSASVGDRVT ITCRASQGIS NYLAWYQQKP GKVPKLLIYA ASTLQSGVPS    60
RFSGSGSGTD FTLTISSLQP EDVATYYCQK YNSAPLTFGG GTKVEIK                 107

SEQ ID NO: 66           moltype = AA  length = 106
FEATURE                 Location/Qualifiers
REGION                  1..106
                        note = synthetic
source                  1..106
                        mol_type = protein
                        organism = synthetic construct
SEQUENCE: 66
DIQMTQSPSS LSASVGDRVT ITCKASQNIN KFIAWYQQKP GKVPKLLIYY TSTLQPGVPS    60
RFSGSGSGTD FTLTISSLQP EDVATYYCLQ YGVLWTFGGG TKVEIK                  106

SEQ ID NO: 67           moltype = AA  length = 106
FEATURE                 Location/Qualifiers
REGION                  1..106
                        note = synthetic
source                  1..106
                        mol_type = protein
                        organism = synthetic construct
SEQUENCE: 67
DIQMTQSPSS LSASVGDRVT ITCKASQNIN KFIAWYQHKP GKVPKLLIHY TSTLQPGVPS    60
RFSGSGSGSD YTLTISSLQP EDIATYYCLQ YGVLWTFGGG TKVEIK                  106

SEQ ID NO: 68           moltype = AA  length = 113
FEATURE                 Location/Qualifiers
REGION                  1..113
                        note = synthetic
source                  1..113
                        mol_type = protein
                        organism = synthetic construct
SEQUENCE: 68
QVQLVQSGAE VKKPGASVKV SCKASGYTFT SYGISWVRQA PGQGLEWMGW ISAYNGNTNY    60
AQKLQGRVTM TTDTSTSTAY MELRSLRSDD TAVYYCARYF DYWGQGTLVT VSS          113

SEQ ID NO: 69           moltype = AA  length = 116
FEATURE                 Location/Qualifiers
REGION                  1..116
                        note = synthetic
source                  1..116
```

```
                            mol_type = protein
                            organism = synthetic construct
SEQUENCE: 69
QIQLVQSGAE VKKPGASVKV SCKASGYTFT TYGMSWVRQA PGQGLEWMGW IHTYSGVPTY    60
ADDFKGRFTF TLDTSTSTAY MELRSLRSDD TAVYYCARGL YGVDYWGQGT LVTVSS       116

SEQ ID NO: 70           moltype = AA  length = 116
FEATURE                 Location/Qualifiers
REGION                  1..116
                        note = synthetic
source                  1..116
                        mol_type = protein
                        organism = synthetic construct
SEQUENCE: 70
QIQLVQSGAE VKKPGASVKV SCKASGYTFT TYGMSWVRQA PGQGLEWMGW IHTYSGVPTY    60
ADDFKGRVTF TLDTSTSTAY MELRSLRSDD TAVYYCARGL YGVDYWGQGT LVTVSS       116

SEQ ID NO: 71           moltype = AA  length = 108
FEATURE                 Location/Qualifiers
REGION                  1..108
                        note = synthetic
source                  1..108
                        mol_type = protein
                        organism = synthetic construct
SEQUENCE: 71
EIVMTQSPAT LSLSPGERAT LSCRASQSVS SSYLSWYQQK PGQAPRLLIY GASTRATGIP    60
ARFSGSGSGT DFTLTISSLQ PEDFAVYYCQ QDYNLPYTFG QGTKLEIK                108

SEQ ID NO: 72           moltype = AA  length = 107
FEATURE                 Location/Qualifiers
REGION                  1..107
                        note = synthetic
source                  1..107
                        mol_type = protein
                        organism = synthetic construct
SEQUENCE: 72
EIVMTQSPAT LSLSPGERAT LSCKASENVV TYVSWYQQKP GQAPRLLIYG ASNRYTGVPD    60
RFTGSGSATD FTLTISSLQP EDFAVYYCGQ SYTYPYTFGQ GTKLEIK                 107

SEQ ID NO: 73           moltype = AA  length = 330
FEATURE                 Location/Qualifiers
REGION                  1..330
                        note = synthetic
source                  1..330
                        mol_type = protein
                        organism = synthetic construct
SEQUENCE: 73
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVAVS HEDPEVKFNW YVDGVEVHNA KTKPREEQYN   180
STYRVVSVLT VLHQDWLNGK EYKCKVSNKA LAAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 74           moltype = AA  length = 451
FEATURE                 Location/Qualifiers
REGION                  1..451
                        note = synthetic
source                  1..451
                        mol_type = protein
                        organism = synthetic construct
SEQUENCE: 74
EVQLLESGGG LVQPGGSLRL SCAASGFTFD DYGMSWVRQA PGKGLEWVSV IYSGGSTYYA    60
DSVKGRFTIS RDNSKNTLYL QMNSLRAEDT AVYYCARDRS SSWYRDGMDV WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                 451

SEQ ID NO: 75           moltype = AA  length = 219
FEATURE                 Location/Qualifiers
REGION                  1..219
                        note = synthetic
source                  1..219
                        mol_type = protein
                        organism = synthetic construct
SEQUENCE: 75
```

-continued

```
QSVLTQPPSA SGTPGQRVTI SCTGSSSNIG AGYDVHWYQQ LPGTAPKLLI YGNSNRPSGV   60
PDRFSGSKSG TSASLAISGL RSEDEADYYC AAWDDSLSGW VFGGGTKLTV LGRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219
```

ANTIBODIES BINDING TNFR2 AND USES THEREOF

CROSS-REFERENCE TO RELATED APPLICATIONS

This application is a bypass continuation of International Patent Application No. PCT/CN2021/099732, filed Jun. 11, 2021, which claims priority to International Patent Application No. PCT/CN2020/095933, filed Jun. 12, 2020, each of which is incorporated herein by reference in its entirety.

REFERENCE TO SEQUENCE LISTING

The instant application contains a Sequence Listing which has been submitted electronically in ASCII format and is hereby incorporated by reference in its entirety. The sequence listing file, entitled PF210364UST_Sequence_ST26, was created on Nov. 30, 2022 and is 110,592 bytes in size.

The present invention relates to a novel antibody or an antibody fragment thereof that specifically binds to TNFR2 and to a composition comprising said antibody or an antibody fragment thereof. In addition, the present invention relates to a nucleic acid encoding the antibody or an antibody fragment thereof and a host cell comprising the same, and to a related use thereof. Besides, the present invention relates to the use of the antibody or antibody fragment for treatment and diagnosis.

BACKGROUND OF THE INVENTION

The tumor necrosis factor receptor superfamily (TNFRSF) is a large class of 29 receptors with related structures capable of mediating a range of immune and non-immune cell functions (Mayes P A et al, Nat Rev Drug Discov. 2018 July; 17(7):509-52). Several receptors have been characterized to have a role as immune co-stimulators (TNFRSF5 (also known as CD40), TNFRSF4 (also known as OX40), TNFRSF9 (also known as 4-1BB), TNFRSF7 (also known as CD27), and TNFRSF18 (also known as GITR). These co-stimulatory receptors can be expressed on a number of immune cell types, including T cells, B cells and natural killer (NK) cells as well as antigen-presenting cells (APCs), and have been shown to drive immune cell function, proliferation and survival.

Tumor necrosis factor-alpha (TNF-α) is a highly pleiotropic cytokine that affects practically any type of cell. It triggers cellular responses reaching from the induction of inflammatory gene expression programs, over the stimulation of cellular proliferation and differentiation to the activation of cellular suicide programs such as apoptosis and necroptosis (Wajant H et al, Cell Death Differ. 2003 January; 10(1):45-65). Both the transmembrane and soluble form of TNF-α interact with the two know receptors of TNF-α. TNFR1 and TNFR2. These two receptors belong to different subgroups of the TNFRSF. TNFR1 is a death receptor (DR) and harbors a death domain. TNFR2 has no death domain and is a prototypic TNF receptor associated factor (TRAF)-interacting TNFRSF receptor (Xie P, J Mol Signal. 2013 Jun. 13; 8(1):7). Thus, there is a short amino acid motif near the C-terminus of TNFR2 which enables recruitment of the adapter protein TRAF2 and TRAF2-associated proteins such as TRAF1 and cellular inhibitor of apoptosis protein 1 (cIAP1) and cIAP2. TNFR2 has therefore no intrinsic cell death inducing activity but stimulates NF-κB signaling and activation of various kinases.

TNFR1 is expressed by almost any cell type. While TNFR2 expression, is rather restricted to certain cell types, including myeloid cells, regulatory T-cells, glial cells and some endothelial cell types, but can also be induced in epithelial cells, fibroblasts and certain T- and B-cell subsets (Medler and Wajant, Expert Opin Ther Targets. 2019 April; 23(4):295-307).

Recent study by Heather Torrey et al (Sci Signal. 2017 Jan. 17; 10(462)) characterized the effect of TNFR2 inhibition using antagonistic antibodies. In culture-based assays, they found that two TNFR2 antagonists inhibited Tregs proliferation, reduced soluble TNFR2 secretion from normal cells, and enabled T effector cell expansion. These TNFR2 antibodies killed Tregs isolated from ovarian cancer ascites more potently than it killed Tregs from healthy donor samples, suggesting that these antibodies may have specificity for the tumor microenvironment.

In another study, Eric M. Tam (Sci Transl Med. 2019 Oct. 2; 11(512)) described their anti-TNFR2 antibodies provided co-stimulatory signaling that led to increases in proliferation, activation markers, and cytokines both in CD4+ and CD8+ T cells in vitro and also had antitumor effects in humanized mouse models.

Although immunotherapeutics targeting the inhibitory receptors CTLA-4, PD-1 or PD-L1 have made substantial clinical progress in cancer, a considerable proportion of patients remain unresponsive to treatment. Immunotherapeutics targeting novel immune-oncology pathways alone or in combination with current immunotherapies may improve clinical outcomes. No anti-TNFR2 antibody is now under clinical investigation, as such, there is a need for TNFR2-targeting therapies that can activate effector T cell's function and enhance T cell's proliferation, and/or inhibit Tregs' function, which is intended for use in cancer.

SUMMARY OF THE INVENTION

The present invention relates to antibodies binding to TNFR2 or its fragments or the antigen-binding fragment thereof. In one embodiment, the TNFR2 is derived from human or cynomolgus. In another embodiment, the TNFR2 comprises SEQ ID NO:48, SEQ ID NO:49 or SEQ ID NO:50. In a further embodiment, the TNFR2's fragment that the antibody can bind comprises the extracellular region of the TNFR2, e.g., the region comprises or consists of SEQ ID NO:50. In a further embodiment, the TNFR2's fragment that the antibody can bind comprises amino acid sequence from 1 L to 31 C of SEQ ID NO:50 or amino acid sequence from 1 L to 96 C of SEQ ID NO:50 or 17T-54D of SEQ ID NO:50. In a further embodiment, the TNFR2's fragment that the antibody can bind comprises Q26 on human TNFR2 protein, or amino acid Q at position corresponding to position 26 on human TNFR2 protein.

In one embodiment, the antibodies of the present invention bind to an epitope of TNFR2. In one embodiment of the present invention, the epitope of TNFR2 that the antibody of the present invention binds comprises Q26 of human TNFR2 or amino acid Q at position corresponding to position 26 on human TNFR2 protein. In one embodiment, the epitope is comprised in the extracellular region of human TNFR2, e.g., the region consisting of or comprising SEQ ID NO:50. In another embodiment, the epitope is comprised in amino acid sequence from 1 L to 31 C of SEQ ID NO: 58 in human TNFR2 or fragments corresponding to it. In another embodiment, the epitope is comprised in amino acid sequence from 1 L to 96 C of SEQ ID NO:62 in human TNFR2 or fragment corresponding to it. In another embodiment, one or more amino acid(s) of the epitope is comprised in amino acid sequence from 17T-54D of SEQ ID NO:52 in human TNFR2 or fragment corresponding to it.

In one aspect, the anti-TNFR2 antibody or the antigen-binding fragment thereof has one or more of the following properties;
(1) binding to human and/or cynomolgus TNFR2 protein or the fragment thereof in vitro with high affinity;
(2) binding to human and/or cynomolgus TNFR2 expressed on cell surface, for example, the cell surface of 293T cells, or the activated cells, such as the PBMC stimulated by anti-CD3;
(3) blocking the interaction/binding between TNF-α and human and/or cynomolgus TNFR2 expressed on the cells, e.g., 293T cells;
(4) Activating the (e.g., human) T-cells (e.g., CD8+ T cells or CD 4+ T cells), e.g., increasing the secretion of cytokine like IFN-gamma, increasing the proliferation of CD4+ T cells or CD8+ T cells;
(5) Stimulating the downstream signal pathway of TNFR2, e.g., human or cynomolgus TNFR2;
(6) Enhancing immune-response;
(7) Not inducing ADCC effects on induced T cells, e.g., induced Treg cells or induced CD8+ T cells;
(8) Being applicable to be used as active ingredients in medicines due to its good pharmacokinetics parameters;
(9) Having anti-tumor effects, e.g., by reducing the tumor volume, e.g., can reduce the tumor volume by at least 20%, 30%, 40%, 50%, 60%, 70%, 80% or more.

In one aspect, the present invention relates to an anti-TNFR2 antibody or the antigen-binding fragment thereof, which comprises three heavy chain complementary determining regions (CDRs) HCDR1, HCDR2 and HCDR3.

In another aspect, the present invention relates to an anti-TNFR2 antibody or the antigen-binding fragment thereof, which comprises three light chain complementary determining regions (CDRs) LCDR1, LCDR2 and LCDR3.

In a further aspect, the present invention relates to an anti-TNFR2 antibody or the antigen-binding fragment thereof, which comprises
three heavy chain complementary determining regions (CDRs) HCDR1, HCDR2 and HCDR3; and
three light chain complementary determining regions (CDRs) LCDR1, LCDR2 and LCDR3.

In another aspect, the present invention relates to an anti-TNFR2 antibody or the antigen-binding fragment thereof, which comprises heavy chain variable region.

In another aspect, the present invention relates to an anti-TNFR2 antibody or the antigen-binding fragment thereof, which comprises light chain variable region.

In a further aspect, the present invention relates to an anti-TNFR2 antibody or the antigen-binding fragment thereof, which comprises a heavy chain variable region, and a light chain variable region.

In one embodiment, the heavy chain variable region comprises three heavy chain complementary determining regions (CDRs) HCDR1, HCDR2 and HCDR3.

In another embodiment, the light chain variable region comprises three light chain complementary determining regions (CDRs) HCDR1, HCDR2 and HCDR3.

In one embodiment, the three heavy chain complementary determining regions HCDR1, HCDR2 and HCDR3 are
(i) the HCDR1, HCDR2 and HCDR3 derived from the heavy chain variable region HCVR, wherein the HCVR comprises or consists of the sequence represented by SEQ ID NO:7, 15, 25 or 37, or
(ii) the HCDR1, HCDR2 and HCDR3 of (i), further comprising at least one and no more than 5 amino acid changes (preferably amino acid substitutions, preferably conservative substitutions) in total compared to the three CDRs of (i).

In one embodiment, the three light chain complementary determining regions (CDRs) LCDR1, LCDR2 and LCDR3 are
(i) the LCDR1, LCDR2 and LCDR3 derived from the light chain variable region LCVR, wherein the LCVR comprises or consists of the sequence represented by SEQ ID NO:8, 16, 26, 28 or 38, or
(ii) LCDR1, LCDR2 and LCDR3 of (i), which further comprise at least one and no more than 5 amino acid changes (preferably amino acid substitutions, preferably conservative substitutions) in total compared to the three CDRs of (i).

In one embodiment, the present invention relates to an anti-TNFR2 antibody or the antigen-binding fragment thereof, which comprises three heavy chain complementary determining regions (CDRs) HCDR1, HCDR2 and HCDR3 derived from the heavy chain variable region HCVR, wherein the HCVR consists of the sequence represented by SEQ ID NO:7, 15, 25 or 37; and three light chain complementary determining regions (CDRs) LCDR1, LCDR2 and LCDR3 derived from the light chain variable region LCVR, wherein the LCVR consists of the sequence represented by SEQ ID NO:8, 16, 26, 28 or 38.

In another embodiment, the present invention relates to an anti-TNFR2 antibody or the antigen-binding fragment thereof, which comprises
(1) three HCDRs HCDR1, HCDR2 and HCDR3 derived from the heavy chain variable region HCVR consisting of the sequence represented by SEQ ID NO:7 or 25; and three LCDRs LCDR1, LCDR2 and LCDR3 derived from the light chain variable region LCVR consisting of the sequence represented by SEQ ID NO:8 or 26 or 28.
(2) three HCDRs HCDR1, HCDR2 and HCDR3 derived from the heavy chain variable region HCVR consisting of the sequence represented by SEQ ID NO:15 or 37; and three LCDRs LCDR1, LCDR2 and LCDR3 derived from the light chain variable region LCVR consisting of the sequence represented by SEQ ID NO:16 or 38.

In one embodiment, HCDR1 comprises or consists of an amino acid sequence selected from the group consisting of SEQ ID NO: 1 or 9, or HCDR1 comprises or consists of an amino acid sequence having one, two or three changes (preferably amino acid substitutions, preferably conservative substitutions) compared to the amino acid sequence selected from the group consisting of SEQ ID NO: 1 or 9.

In one embodiment, HCDR2 comprises or consists of an amino acid sequence selected from the group consisting of SEQ ID NO: 2 or 10, or HCDR2 comprises or consists of an amino acid sequence having one, two or three changes (preferably amino acid substitutions, preferably conservative substitutions) compared to the amino acid sequence selected from the group consisting of SEQ ID NO: 2 or 10.

In one embodiment, HCDR3 comprises or consists of an amino acid sequence selected from the group consisting of SEQ ID NO: 3 or 11, or HCDR3 comprises or consists of an amino acid sequence having one, two or three changes (preferably amino acid substitutions, preferably conservative substitutions) compared to the amino acid sequence selected from the group consisting of SEQ ID NO: 3 or 11.

In one embodiment, LCDR1 comprises or consists of an amino acid sequence selected from the group consisting of SEQ ID NO: 4 or 12, or LCDR1 comprises or consists of an amino acid sequence having one, two or three changes (preferably amino acid substitutions, preferably conservative substitutions) compared to the amino acid sequence selected from the group consisting of SEQ ID NO: 4 or 12.

In one embodiment, LCDR2 comprises or consists of an amino acid sequence selected from the group consisting of SEQ ID NO: 5 or 13, or LCDR2 comprises or consists of an amino acid sequence having one, two or three changes (preferably amino acid substitutions, preferably conservative substitutions) compared to the amino acid sequence selected from the group consisting of SEQ ID NO: 5 or 13.

In one embodiment, LCDR3 comprises or consists of an amino acid sequence selected from the group consisting of SEQ ID NO: 6 or 14, or LCDR3 comprises or consists of an amino acid sequence having one, two or three changes (preferably amino acid substitutions, preferably conservative substitutions) compared to the amino acid sequence selected from the group consisting of SEQ ID NO: 6 or 14.

In one embodiment, the three heavy chain complementary determining regions HCDR1, HCDR2 and HCDR3 are
(i) the HCDR1. HCDR2 and HCDR3 consisting of the sequence represented by SEQ ID NO: 1, 2 and 3 respectively, or
(ii) the HCDR1, HCDR2 and HCDR3 consisting of the sequence represented by SEQ ID NO: 9, 10 and 11 respectively, or
(iii) the HCDR1, HCDR2 and HCDR3 of (i) or (ii), further comprising at least one and no more than 5 amino acid changes (preferably amino acid substitutions, preferably conservative substitutions) in total compared to the three CDRs of (i) or (ii).

In one embodiment, the three light chain complementary determining regions (CDRs) LCDR1, LCDR2 and LCDR3 are
(i) the LCDR1, LCDR2 and LCDR3 consisting of the sequence represented by SEQ ID NO: 4, 5 and 6 respectively, or
(ii) the LCDR1, LCDR2 and LCDR3 consisting of the sequence represented by SEQ ID NO: 12, 13 and 14 respectively, or
(iii) LCDR1, LCDR2 and LCDR3 of (i), which further comprise at least one and no more than 5 amino acid changes (preferably amino acid substitutions, preferably conservative substitutions) in total compared to the three CDRs of (i).

In another embodiment, the present invention relates to an anti-TNFR2 antibody or the antigen-binding fragment thereof, which comprises
(i) the HCDR1, HCDR2 and HCDR3 consisting of the sequence represented by SEQ ID NO: 1, 2 and 3 respectively, and the LCDR1, LCDR2 and LCDR3 consisting of the sequence represented by SEQ ID NO: 4, 5 and 6 respectively.
(ii) the HCDR1, HCDR2 and HCDR3 consisting of the sequence represented by SEQ ID NO: 9, 10 and 11 respectively, and the LCDR1, LCDR2 and LCDR3 consisting of the sequence represented by SEQ ID NO: 12, 13 and 14 respectively.

In one embodiment, the heavy chain variable region
(i) comprises or consists of an amino acid sequence having at least 90%, 91%, 92%, 93%. 94%, 95%, 96%, 97%. 98% or 99% identity with the amino acid sequence selected from the group consisting of SEQ ID NOs: 7, 15, 25 or 37; or (ii) comprises or consists of an amino acid sequence selected from the group consisting of SEQ ID NOs: 7, 15, 25 or 37; or
(iii) comprises or consists of an amino acid sequence having one or more (preferably no more than 10, more preferably no more than 5) amino acid changes (preferably amino acid substitutions, more preferably conservative substitutions) compared to an amino acid sequence selected from the group consisting of SEQ ID NOs: 7, 15, 25 or 37, preferably, said amino acid changes do not occur in the CDR regions, more preferably, said amino acid changes occur in Framework region (FR regions), e.g., FR1, FR2, FR3 or FR4 regions.

In another embodiment, the light chain variable region
(i) comprises or consists of an amino acid sequence having at least 90%, 91%, 92%, 93%, 94%, 95%, 96%, 97%, 98% or 99% identity with the amino acid sequence selected from the group consisting of SEQ ID NOs:8, 16, 26, 28 or 38; or
(ii) comprises or consists of an amino acid sequence selected from the group consisting of SEQ ID NOs: 8, 16, 26, 28 or 38; or
(iii) comprises or consists of an amino acid sequence having one or more (preferably no more than 10, more preferably no more than 5) amino acid changes (preferably amino acid substitutions, more preferably conservative substitutions) compared to an amino acid sequence selected from the group consisting of SEQ ID NOs: 8, 16, 26, 28 or 38, preferably, said amino acid changes do not occur in the CDR regions, more preferably, said amino acid changes occur in FR regions, e.g., FR1, FR2, FR3 or FR4 regions, preferably, the change occur at Q38 in FR1, especially the change is from Q to H or its conservative amino acid.

In another embodiment, the present invention relates to an anti-TNFR2 antibody or the antigen-binding fragment thereof, which comprises:
a heavy chain variable region comprising or consisting of an amino acid sequence represented by SEQ ID NOs: 7, 15, 25 or 37, and/or
a light chain variable region comprising or consisting of an amino acid sequence represented by SEQ ID Nos: 8, 16, 26, 28 or 38.

In another embodiment, the present invention relates to an anti-TNFR2 antibody or the antigen-binding fragment thereof, which comprises:
(1) a heavy chain variable region comprising or consisting of an amino acid sequence represented by SEQ ID NO: 7, and/or a light chain variable region comprising or consisting of an amino acid sequence represented by SEQ ID No: 8;
(2) a heavy chain variable region comprising or consisting of an amino acid sequence represented by SEQ ID NO: 15, and/or a light chain variable region comprising or consisting of an amino acid sequence represented by SEQ ID No: 16;
(3) a heavy chain variable region comprising or consisting of an amino acid sequence represented by SEQ ID NO: 25, and/or a light chain variable region comprising or consisting of an amino acid sequence represented by SEQ ID No: 26;
(4) a heavy chain variable region comprising or consisting of an amino acid sequence represented by SEQ ID NO: 25, and/or a light chain variable region comprising or consisting of an amino acid sequence represented by SEQ ID No: 28.

(5) a heavy chain variable region comprising or consisting of an amino acid sequence represented by SEQ ID NO: 37, and/or a light chain variable region comprising or consisting of an amino acid sequence represented by SEQ ID No: 38.

In a further aspect, the anti-TNFR2 antibody or the antigen-binding fragment thereof is in the form of IgG1, IgG2, IgG3 or IgG4. Preferably, the antibodies of the present invention are in the form of IgG1.

In a further aspect, the anti-TNFR2 antibody or the antigen-binding fragment thereof further comprises heavy chain constant region, and/or light chain constant region.

In one embodiment, the heavy chain constant region is or is derived from human IgG constant region, e.g., IgG1, IgG2, IgG3 or IgG4, preferable IgG1 constant region.

In another embodiment, the heavy chain constant region
(i) comprises or consists of an amino acid sequence having at least 900%, 91%, 92%, 93%. 94%, 95%, 96%, 97%. 98% or 99% identity with the amino acid sequence represented by SEQ ID NO: 40 or SEQ ID NO:73; or
(ii) comprises or consists of an amino acid sequence represented by SEQ ID NO: 40 or SEQ ID NO:73; or
(iii) comprises or consists of an amino acid sequence having one or more (preferably no more than 10, more preferably no more than 5) amino acid changes (preferably amino acid substitutions, more preferably conservative substitutions) compared to an amino acid sequence represented by SEQ ID NO:40 or SEQ ID NO:73.

In one embodiment, the light chain constant region is or is derived from kappa or lambda light chain constant region, e.g., human kappa or lambda light chain constant region, preferably human kappa light chain constant region.

In another embodiment, the light chain constant region
(i) comprises or consists of an amino acid sequence having at least 90%, 91%, 92%, 93%, 94%, 95%, 96%, 97%, 98% or 99% identity with the amino acid sequence represented by SEQ ID NO: 42; or
(ii) comprises or consists of an amino acid sequence represented by SEQ ID NO: 42; or
(iii) comprises or consists of an amino acid sequence having one or more (preferably no more than 10, more preferably no more than 5) amino acid changes (preferably amino acid substitutions, more preferably conservative substitutions) compared to an amino acid sequence represented by SEQ ID NO:42.

In one embodiment, the heavy chain of the anti-TNFR2 antibody or antigen binding fragment thereof of the present invention further comprises a signal peptide sequence.

In another embodiment, the anti-TNFR2 antibody of the present invention is a monoclonal antibody, a chimeric antibody, humanized antibody or a human antibody.

In another embodiment, the antigen-binding fragment of the present invention is an antibody fragment selected from the group consisting of Fab, Fab', Fab'-SH, Fv, single chain antibody (e.g., scFv), (Fab')2, single domain antibody (e.g., VHH), domain antibody (dAb) or linear antibody.

In another embodiment, the anti-TNFR2 antibody of the present invention is a bispecific or multispecific antibody molecule, preferably the bispecific antibody molecule binds to TNFR2 and immune checkpoint(s).

In a further aspect, the present invention further relates to an isolated nucleic acid encoding the anyone or more chains of anti-TNFR2 antibody of the present invention.

In a further aspect, the present invention further relates to a vector comprising the nucleic acid of the present invention. In one embodiment, the vector is an expression vector.

In a further aspect, the present invention further relates to a host cell comprising the nucleic acid or the vector of the present invention. Preferably the host cell is prokaryotic or eukaryotic, more preferably selected from yeast cells, mammalian cells (e.g., CHO cells or CHO-S cells or 293 cells or 293T cells), or other cells suitable for the preparation of antibodies or antigen-binding fragments thereof.

In a further aspect, the present invention further relates to a method of preparing an anti-TNFR2 antibody or the antigen-binding fragment thereof comprising culturing the host cell according to the invention, under conditions suitable for expression of a nucleic acid encoding an anti-TNFR2 antibody or the antigen-binding fragment thereof of the present invention, optionally said method further comprises recovering the anti-TNFR2 antibody or the antigen-binding fragment thereof from the host cell.

In a further aspect, the present invention further relates to an immunoconjugate comprising the anti-TNFR2 antibody or the antigen-binding fragment thereof according to the present invention, and other agent, e.g., a therapeutic agent or a marker, such as a cytotoxic agent.

In a further aspect, the present invention further relates to a pharmaceutical composition comprising the anti-TNFR2 antibody or the antigen-binding fragment thereof according to the present invention, or the immunoconjugate of the present invention, and optionally a pharmaceutically acceptable adjuvant.

In a further aspect, the present invention further relates to a combination product, comprising the anti-TNFR2 antibody or the antigen-binding fragment thereof of the present invention, or the immunoconjugate of the present invention, and one or more other therapeutic agents, e.g., a chemotherapeutic agent, other antibody, cytotoxic agent, vaccine, anti-infection agents, small molecular entity, or immune-regulating agent.

In a further aspect, the present invention further relates to a method of activating T cells, or inducing T cell mediated antitumor activity, or enhancing T-cell mediated immune, or stimulating the proliferation of T cells in a subject, comprising administering to said subject the anti-TNFR2 antibody or the antigen-binding fragment thereof, or the immunoconjugate the invention, or the pharmaceutical composition, or the combination product of the present invention.

In a further aspect, the present invention further relates to a method of preventing or treating cancer or infection in a subject comprising administering to said subject the anti-TNFR2 antibody or the antigen-binding fragment thereof, or the immunoconjugate, or the pharmaceutical composition, or the combination product of the present invention.

In one embodiment, the cancer is that with high level of TNFR2 (e.g., the high protein or nucleic acid level of TNFR2). In another embodiment, said cancer is non-small cell lung cancer, breast cancer, renal cell carcinoma, Hodgkin lymphoma, multiple myeloma, cutaneous non-Hodgkin lymphoma, and ovarian cancer, cancer in gastrointestinal tract, e.g., colorectal cancer, rectal cancer or colon cancer.

In one embodiment, the infection is viral infection, bacterial infection, fungal infection, or protozoan such as parasitic infection.

In one embodiment, the method of the present invention further comprises administering to said subject in combination with one or more therapies, e.g., a therapeutic modality and/or other therapeutic agent, preferably the therapeutic modality includes surgery and/or radiation therapy, and/or the other therapeutic agent is selected from the group consisting of a chemotherapeutic agent, other antibody, cytotoxic agent, vaccine, anti-infection agents, small molecular entity, or immune-regulating agent.

In a further aspect, the present invention further relates to a method of detecting TNFR2 in a sample, said method comprising:
  (a) contacting the sample with any anti-TNFR2 antibody or antigen binding fragment thereof according to the invention;
  (b) detecting the formation of a complex between the anti-TNFR2 antibody or antigen binding fragment thereof and the TNFR2; optionally, the anti-TNFR2 antibody is detectably labeled.

In a further aspect, the present invention further relates to a kit for detecting TNFR2, comprising the anti-TNFR2 antibody or the antigen-binding fragment thereof, or an immunoconjugate of the present invention.

The invention also encompasses any combination of any of the embodiments described herein. Any of the embodiments described herein, or any combination thereof, are applicable to any and all of the anti-TNFR2 antibodies or fragments of the invention as described herein and methods and uses thereof.

BRIEF DESCRIPTION OF THE DRAWINGS

FIG. 1 shows the binding of chimeric antibodies to human and cynomolgus TNFR2 protein.

FIG. 2 shows the chimeric antibodies bind to cynomolgus or human TNFR2 on cell surface, and block the binding of TNF-alpha with human TNFR2 on cell surface.

FIG. 3 shows humanized antibodies bind to human TNFR2 and block human TNFR2's binding to TNF-alpha.

FIG. 4 shows the humanized antibodies bind to cynomolgus TNFR2 on cell surface and block human TNFR2's binding to TNF-alpha.

FIG. 5 shows the co-stimulation of the humanized antibodies on human CD8+ T cells.

FIG. 6 shows that the humanized antibodies co-stimulate the proliferation of T cells.

FIG. 7 shows that the humanized antibodies activate the T cells in a Fc-crosslinking form.

FIG. 8 shows the binding of the humanized antibodies to TNFRSF proteins.

FIG. 9 shows the purity of humanized antibodies hu32-C and hu32C-V1 in SEC-HPLC.

FIG. 10 shows the anti-TNFR2 antibody hu3-E epitope mapping.

FIG. 11 shows the anti-TNFR2 antibody hu32C-V1 epitope mapping.

FIG. 12 shows the anti-TNFR2 antibody hu3-E bound to TNFR2 on activated PBMC cells.

FIG. 13 shows the ADCC effect of anti-human TNFR2 antibodies on Treg cells.

FIG. 14 shows the ADCC effect of anti-human TNFR2 antibodies on CD8+ T cells.

DETAILED DESCRIPTION OF THE INVENTION

Definitions

For the purpose of interpreting the specification, the following definitions will be used, and the terms used in the singular may also include the plural, and vice versa, if appropriate. It is understood that the terminology used herein is for the purpose of describing particular embodiments and is not intended to be restrictive.

The term "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone).

It is understood that wherever aspects are described herein with the language "comprising," otherwise analogous aspects described in terms of "consisting of" and/or "consisting essentially of" are also provided.

The term "about" w % ben used in connection with a numerical value is meant to encompass numerical values within the range between the lower limit of 10% or 5% less than the specified numerical value and the upper limit of 10% or 5% greater than the specified numerical value.

"Tumor necrosis factor receptor type 2 (TNFR2)" is highly expressed by tumor-infiltrating immunosuppressive CD4+FoxP3+ regulatory T cells (Tregs) and has been shown to mediate the stimulatory effect of tumor necrosis factor (TNF) on these cells. Recent studies have shown that TNFR2 plays a crucial role in stimulating the activation and proliferation of Tregs, a major checkpoint of antitumor immune responses (Chen and Oppenheim, Sci Signal 10: eaa12328, 2017). TNFR2 is also expressed by some types of malignant cells and the survival and growth of these tumor cells is promoted by ligands of TNFR2. In one embodiment, the TNFR2 in the present invention is derived from human, e.g., it has the amino acid sequence represented by SEQ ID NO:48. In another embodiment, the TNFR2 is derived from Cynomolgus, e.g., it has the amino acid sequence represented by SEQ ID NO:49. The fragment of TNFR2 used herein refers to any part of TNFR2, especially the part that the anti-TNFR2 antibody of the present invention binds to. In one embodiment, the fragment is the extracellular region of TNFR2, e.g., the region having the amino acid sequence represented by SEQ ID NO:50.

An "anti-antigen" antibody refers to an antibody that binds specifically to the antigen. For example, an anti-TNFR2 antibody binds specifically to TNFR2.

An "isolated" antibody is one which has been separated from a component of its natural environment. In some embodiments, an antibody is purified to greater than 90% or 95% or 99% purity as determined by, for example, electrophoretic (e.g., SDS-PAGE, isoelectric focusing (IEF), capillary electrophoresis) or chromatographic (e.g., ion exchange or reverse phase HPLC). In one embodiment of the present invention, the anti-TNFR2 antibody is isolated.

The term "anti-TNFR2 antibody", "anti-TNFR2", "TNFR2 antibody" or "antibody binding to TNFR2" as used herein refers to an antibody which is capable of binding to (e.g., human or Cynomolgus) TNFR2 protein or a fragment thereof with sufficient affinity such that the antibody can be used as diagnostic and/or therapeutic agent targeting (human or Cynomolgus) TNFR2. In one embodiment, the anti-TNFR2 antibody binds to non-TNFR2 protein (e.g., non-human or non-cynomolgus TNFR2) to an extent lesser than about 10%, about 20%, about 30%, about 40%, about 50%, about 60%, about 70%, about 80% or about 90% or above of the binding of the antibody to (e.g., human or Cynomolgus) TNFR2, as measured, for example, by radioimmuno-assay (RIA) or Bio-light interferometry or MSD assay. In one embodiment, the antibody bind to human or cynomolgus TNFR2 protein or the fragment thereof in vitro with high affinity means that compared to binding to non-TNFR2 protein (e.g., non-human or non-cynomolgus TNFR2 respectively), the binding extend is higher than about about 70%, about 80% or about 90% or above. In one embodiment, the antibody bind to Cynomolgus TNFR2 protein or the fragment thereof in vitro with high affinity means that the $K_D$ of the antibody binding to the Cynomolgus TNFR2 is lower than 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 0.9 nM, 0.8 nM, 0.7 nM, or between the values listed above, e.g., about 0.5 nM-10 nM, 0.5 nM-8 nM, 0.5 nM-6 nM. In one embodiment, the antibody bind to human TNFR2 protein or the fragment thereof in vitro with high affinity means that the $K_D$ of the antibody binding to the human TNFR2 is lower than 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM or between the values listed above, e.g., about 0.3 nM-5 nM or 0.3 nM-4 nM.

The antibody may be an antibody that has been changes (e.g., by insertion, deletion, substitution, conjugation to a non-antibody moiety). For example, an antibody may include one or more variant amino acids (compared to a naturally occurring antibody) which change a property (e.g., a functional property) of the antibody. For example, several changes are known in the art which affect, e.g., half-life, effector function, and/or immune responses to the antibody in a patient.

The term "monoclonal antibody" ("mAb") refers to a preparation of antibody molecules of single molecular composition, i.e., antibody molecules which exhibit a single binding specificity and affinity for a particular antigen. A monoclonal antibody is an example of an isolated antibody. MAbs may be produced by hybridoma, recombinant, transgenic or other techniques known to those skilled in the art.

A "human" antibody (HuMAb) refers to an antibody having variable regions in which both the framework and CDR regions are derived from human germline immunoglobulin sequences. The terms "human" antibodies and "fully human" antibodies and are used synonymously.

A "humanized antibody" refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "antigen-binding fragment" of an antibody refers to one or more fragments of an antibody that retain the ability to bind specifically to the antigen bound by the whole antibody. Examples of binding fragments encompassed within the term "antigen-binding fragment" of an antibody, include but are not limited to Fv, Fab, Fab', Fab'-SH, F(ab')2; diabodies; linear antibodies; single-chain antibody molecules (e.g. scFv); single domain antibody; and multispecific antibodies formed from antibody fragments.

These antibody fragments are obtained using conventional techniques known to those with skill in the art, and the fragments are screened for utility in the same manner as are intact antibodies. Antigen-binding fragments can be produced by recombinant DNA techniques, or by enzymatic or chemical cleavage of intact immunoglobulins.

As used herein, the term "epitope" refers to a portion of an antigen (e.g., TNFR2) that specifically interacts with an antibody molecule. This portion (referred to herein as an epitope determinant) typically comprises an element such as an amino acid side chain or a sugar side chain or a component thereof. Epitope determinants can be defined according to methods known in the art or disclosed herein (e.g., by crystallography or by hydrogen-deuterium exchange). Typically, epitopes have specific three dimensional structural characteristics. Typically, epitopes have specific charge characteristics. Some epitopes are linear epitopes, while others are conformational epitopes. In one embodiment of the present invention, the epitope of TNFR2 that the antibody of the present invention binds comprises Q26 of human TNFR2 or amino acid Q at position corresponding to position 26 on human TNFR2 protein. In one embodiment, the epitope is comprised in the extracellular region of human TNFR2, e.g., the region consisting of or comprising SEQ ID NO:50. In another embodiment, the epitope is comprised in amino acid sequence from 1 L to 31 C of SEQ ID NO:58 in human TNFR2 or fragments corresponding to it. In another embodiment, the epitope is comprised in amino acid sequence from 1 L to 96 C of SEQ ID NO:62 in human TNFR2 or fragment corresponding to it. In another embodiment, the epitope is comprised in amino acid sequence from 17T-54D of SEQ ID NO:52 in human TNFR2 or fragment corresponding to it.

An "antibody that binds to the same or overlapping epitope" as a reference antibody refers to an antibody that blocks binding of the reference antibody to its antigen in a competition assay by 50% or more, and conversely, the reference antibody blocks binding of the antibody to its antigen in a competition assay by 50% or more.

An antibody that competes with a reference antibody for binding to its antigen refers to an antibody that blocks 50%, 60%, 70%, 80%, 90% or 95% or more of the binding of the reference antibody to its antigen in a competition assay. In other words, the reference antibody blocks 50%, 60%, 70%, 80%, 90% or 95% or more of the binding of the antibody to its antigen in a competition assay. Numerous types of competitive binding assays can be used to determine whether an antigen binding protein competes with another assay such as solid phase direct or indirect radioimmunoassay (RIA), solid phase direct or indirect enzyme immunoassay (EIA), Sandwich competition assays.

An antibody that inhibits (e.g., competitively inhibits) binding of a reference antibody to its antigen refers to an antibody that inhibits binding of 50%, 60%, 70%, 80%, 90%, or 95% or more of the reference antibody to its antigen. Conversely, the reference antibody inhibits binding of the antibody to its antigen by 50%, 60%, 70%, 80%, 90% or 95% or more. The binding of an antibody to its antigen can be measured by affinity. Methods for determining affinity are known in the art.

An antibody that exhibits the same or similar binding affinity and/or specificity as a reference antibody refers to an antibody that has at least 50%, 60%, 70%. 80%, 90% or 95% or more of the binding affinity and/or specificity of the reference antibody. This can be determined by any method known in the art for determining binding affinity and/or specificity.

"Complementarity determining region" or "CDR region" or "CDR" is a region in an antibody variable domain that is highly variable in sequence and forms a structurally defined loop ("hypervariable loop") and/or comprises antigen-contacting residues ("antigen contact point"). CDRs are primarily responsible for binding to epitopes. The CDRs of the heavy and light chains are generally referred to as CDR1, CDR2, and CDR3, and are numbered sequentially from the N-terminus. The CDRs located in the variable domain of the antibody heavy chains are referred to as HCDR1, HCDR2, and HCDR3, while the CDRs located in the variable domain of the antibody light chains are referred to as LCDR1, LCDR2, and LCDR3. In a given amino acid sequence of a light chain variable region or a heavy chain variable region, the exact amino acid sequence boundary of each CDR can be determined using any one or a combination of many well-known antibody CDR assignment systems including, e.g., Chothia based on the three-dimensional structure of antibodies and the topology of the CDR loops (Chothia et al. (1989) Nature 342:877-883; Al-Lazikani et al., "Standard conformations for the canonical structures of immunoglobulins", Journal of Molecular Biology, 273:927-948 (1997)), Kabat based on antibody sequence variability (Kabat et al., Sequences of Proteins of Immunological Interest, 4th edition, US Department of Health and Human Services, National Institutes of Health (1987)), AbM (University of Bath), Contact (University College London), International ImMunoGeneTics database (IMGT) (imgt.cines.fr/ on the World Wide Web), and North CDR definition based on the affinity propagation clustering using a large number of crystal structures.

For example, according to different CDR determination schemes, the residues of each CDR are as follows.

| CDR | Kabat scheme | AbM scheme | Chothia scheme | Contact scheme |
|---|---|---|---|---|
| LCDR1 | L24-L34 | L24-L34 | L26-L32 | L30-L36 |
| LCDR2 | L50-L56 | L50-L56 | L50-152 | L46-L55 |
| LCDR3 | L89-L97 | L89-L97 | L91-L96 | L89-L96 |
| HCDR1 | H31-H35B | H26-H35B | H26-H32 | H30-H35B |
| | (Kabat numbering system) | | | |
| HCDR1 | H31-H35 | H26-H35 | H26-H32 | H30-H35 |
| | (Chothia Numbering System) | | | |
| HCDR2 | H50-H65 | H50-H58 | H53-H55 | H47-H58 |
| HCDR3 | H95-H102 | H95-H102 | H96-H101 | H93-H101 |
| | (Kabat numbering system) | | | |

CDRs can also be determined based on having the same Kabat numbering positions as a reference CDR sequence (e.g., any of the exemplary CDRs of the invention).

Unless otherwise stated, in the invention, the term "CDR" or "CDR sequence" encompasses CDR sequences determined by any of the manners described above.

Unless otherwise stated, in the invention, when referring to the position of residues in an antibody variable region (including heavy chain variable region residues and light chain variable region residues), it refers to the numbering positions according to the Kabat numbering system (Kabat et al. Sequences of Proteins of Immunological Interest, 5th Ed. Public Health Service, National Institutes of Health, Bethesda, Md. (1991)).

In one embodiment, the boundaries of the CDRs of the antibodies of the invention are determined by Kabat scheme.

It should be noted that boundaries of CDRs of variable regions of an antibody obtained by different assignment systems may differ. That is, CDR sequences of variable regions of an antibody defined by different assignment systems differ.

Therefore, when it comes to defining an antibody with specific CDR sequences defined in the invention, the scope of the antibody also encompasses such antibody whose variable region sequences comprise the specific CDR sequences, but having claimed CDR boundaries different from the specific CDR boundaries defined by the invention as a different protocol (e.g., different assignment system rules or their combinations) is applied.

Antibodies with different specificities (i.e., different binding sites for different antigens) have different CDRs (under the same assignment system). However, although CDRs differ from antibody to antibody, only a limited number of amino acid positions within the CDRs are directly involved in antigen binding. The smallest overlapping region can be determined using at least two of the Kabat, Chothia, AbM, Contact, and North methods, thereby providing a "minimal binding unit" for antigen binding. The minimal binding unit may be a sub-portion of the CDR. As will be clear to those skilled in the art, residues of the rest CDR sequences can be determined by antibody structure and protein folding. Therefore, any variants of the CDRs given herein will also be considered in the invention. For example, in one CDR variant, the amino acid residues in the minimal binding unit may remain unchanged, while the other CDR residues defined by Kabat or Chothia may be substituted by conservative amino acid residues.

There are five major classes of antibodies known in the art: IgA, IgD, IgE, IgG and IgM, and several of these antibodies can be further divided into subclasses (isotypes), for example, $IgG_1$, $IgG_2$, $IgG_3$. $IgG_4$. $IgA_1$ and $IgA_2$. The heavy chain constant domains corresponding to different classes of immunoglobulins are referred to as α, δ, ε, γ, and μ, respectively. A person skilled in the art can select and obtain the antibody in an appropriate class of the present invention according to the practical desire.

"Antibody in IgG form" refers to the IgG form to which the heavy chain constant region of an antibody belongs. The heavy chain constant regions of all antibodies of the same type are identical, and the heavy chain constant regions differ between different types of antibodies. For example, an antibody in the IgG1 form refers to an Ig domain whose heavy chain constant region Ig domain is IgG1.

An "isolated" nucleic acid refers to a nucleic acid molecule which has been separated from components of its natural environment. The isolated nucleic acid includes a nucleic acid molecule contained in a cell that normally contains the nucleic acid molecule, but present extra chromosomally or at a chromosomal location that is different from its natural chromosomal location.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell" refers to cells into which exogenous nucleic acid has been introduced, including the progeny of such cells. Host cells include "transformants" and "transformed cells", which include the primary transformed cell and progeny derived therefrom regardless of the number of passages. Progeny may not be completely identical in nucleic acid content to a parent cell, but may contain mutations. Mutant progeny that have the same function or biological activity as screened or selected for in the originally transformed cell are included herein.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways in the art, for instance, using publicly available computer software such as BLAST, BLAST-2, ALIGN or MEGALIGN (DNASTAR) software. Those skilled in the art can determine appropriate parameters for aligning sequences, including any algorithm needed to achieve maximal alignment over the full length of the sequences being compared.

When percentages of sequence identity are referred to in this application, these percentages are calculated relative to the full length of the longer sequence, unless otherwise specifically indicated. The calculation relative to the full length of the longer sequence applies to both the nucleic acid sequence and the polypeptide sequence.

The term "pharmaceutical composition" refers to a formulation which is in such form as to permit the biological activity of an active ingredient contained therein to be effective, and which contains no additional components which are unacceptably toxic to a subject to which the formulation would be administered.

The term "pharmaceutically acceptable adjuvants" refers to a diluent, adjuvant (e.g., Freund's adjuvant (complete and incomplete)), excipient or vehicle co-administered with the therapeutic agent.

As used herein, "treatment" (or "treat" or "treating") refers to slowing, interrupting, arresting, alleviating, stopping, reducing, or reversing the progression or severity of an existing symptom, disorder, condition, or disease.

As used herein, "prevention" (or "prevent" or "preventing") includes the inhibition of the onset or progression of a disease or disorder or a symptom of a particular disease or disorder. In some embodiments, subjects with family history of cancer are candidates for preventive regimens. Generally, in the context of cancer, the term "prevention" refers to the administration of a drug prior to the onset of signs or symptoms of a cancer, particularly in subjects at risk of cancer.

"Activating T cell" means to induce, cause or stimulate an effector or memory T cell to have a renewed, sustained or amplified biological function. Examples of enhancing T-cell function include: increased secretion of γ-interferon (e.g., IFN-gamma) from CD8+ T cells, increased proliferation of CD4+ T cells, increased proliferation of CD8+ T-cells, relative to such levels before the intervention.

The term "therapeutic agent" as described herein encompasses any substance effective in preventing or treating tumors (such as cancer) and infections, including chemotherapeutic agents, cytotoxic agents, vaccines, other antibodies (e.g., antibodies against to the immune checkpoint molecule), active anti-infective agents, immunomodulators, small entities.

"Chemotherapeutic agents" include chemical compounds useful in treatment of cancer.

The term "immune checkpoint molecule" refers to the group of molecules on the cell surface of CD4 T cells and CD8 T cells. These molecules can effectively act as "brakes" that down-regulate or suppress anti-tumor immune responses.

The term "anti-infective agent" includes any molecule that specifically inhibits or eliminates the growth of microorganisms such as viruses, bacteria, fungi, or protozoa, e.g., parasites, and is not lethal to the host, at the administration concentration and interval of administration. As used herein, the term anti-infective agent includes antibiotics, antibacterials, antivirals, antifungals, and antiprotozoals. In one specific aspect, the anti-infective agent is non-toxic to the host at the administration concentration and interval of administration.

Immunomodulators include immune checkpoint molecule inhibitors and co-stimulatory molecule activators.

The term "small molecule" refers to any molecule with a molecular weight of about 2000 daltons or less, preferably of about 500 daltons or less.

The term "combination product" refers to a fixed or non-fixed combination of dosage unit forms or a kit of parts for combined administration in which two or more therapeutic agents can be administered independently at the same time or administered separately within a time interval, especially when these time intervals allow the combined partner to demonstrate collaboration, for example, synergistic effects. The term "fixed combination" means that the antibody of the invention and the combination partner (e.g., other therapeutic agents, such as immunomodulators, such as immunosuppressive agents or anti-inflammatory agents) are administered to a patient simultaneously in the form of a single entity or dose. The term "non-fixed combination" means that the antibodies and combination partners of the present invention (e.g., other therapeutic agents, such as immunomodulators, such as immunosuppressive agents or anti-inflammatory agents) are administered to patients simultaneously, concurrently, or sequentially as separate entities, and there is no specific time limitation, where such administration provides therapeutically effective levels of the two compounds in the patient. The latter also applies to cocktail therapy, such as the administration of three or more therapeutic agents. In a preferred embodiment, the drug combination is a non-fixed combination.

The terms "cancer" and "cancerous" refer to or describe a physiological disease in mammals that is typically characterized by unregulated cell growth.

The term "tumor" refers to all neoplastic cell growth and proliferation regardless of whether malignant or benign, and all pre-cancerous and cancerous cells and tissues. The terms "cancer", "cancerous", "cell proliferative disorder", "proliferative disorder", and "tumor" are not mutually exclusive when referred to herein.

The term "infectious disease" refers to a disease caused by a pathogen, including, for example, viral infection, bacterial infection, fungal infection, or protozoan such as parasitic infection.

The term "tumor immune escape" refers to tumors evading immune recognition and clearance. Therefore, as a concept of treatment, tumor immunity is "treated" and the tumor is recognized and attacked by the immune system when the escape is weakened. Examples of tumor recognition include tumor binding, tumor shrinkage, and tumor clearance.

The term "label" used herein refers to a compound or composition which is directly or indirectly conjugated or fused to an agent, such as a polynucleotide probe or an antibody, and facilitates the detection of the agent to which it is conjugated or fused. The label itself can be detectable (e.g., a radioisotope label or a fluorescent label) or can catalyze a chemical change of a detectable substrate compound or composition in the case of enzymatic labeling. The term is intended to encompass direct labeling of a probe or an antibody by coupling (i.e., physical linking) a detectable substance to the probe or antibody and indirect labeling of a probe or an antibody by reacting with another reagent which is directly labeled.

The term "effective amount" refers to an amount or dosage of the antibody or fragment or conjugate or composition of the invention which generates expected effects in a patient in need of treatment or prevention after administered to the patient in a single or multiple doses. The effective amount can be easily determined by an attending physician as a person skilled in the art by considering a variety of factors as follows: species such as mammals; its size, age, and general health; the specific disease involved; the extent or severity of the disease; response in an individual patient; specific antibody administered; route of administration; bioavailability characteristics of the administered formulation; selected dose regimen; and use of any concomitant therapy.

"Therapeutically effective amount" refers to an amount effective to achieve a desired therapeutic outcome at a required dosage for a desired period of time. The therapeutically effective amount of an antibody or an antibody fragment, or conjugate or composition thereof can vary depending on a variety of factors such as morbid state, age, sex, and weight of an individual, and the ability of the antibody or antibody portion to elicit a desired response in the individual. The therapeutically effective amount is also such an amount in which any toxic or undesired effect of the antibody or antibody fragment, or conjugate or composition thereof is inferior to the therapeutically beneficial effect. "Therapeutically effective amount" preferably inhibits a measurable parameter (e.g., tumor growth rate) by at least about 20%, more preferably at least about 40%, even more preferably at least about 50%, 60%, or 70%, and still more preferably at least about 80% or 90%, relative to untreated subjects.

"Prophylactically effective amount" refers to an amount effective to achieve a desired prophylactic outcome at a required dosage for a desired period of time.

Generally, since a prophylactic dose is administered in a subject before or at an earlier stage of a disease, a prophylactically effective amount will be less than a therapeutically effective amount.

"Individual" or "subject" includes mammals. Mammals include, but are not limited to, domestic animals (e.g., cattle, goat, cat, dog, and horse), primates (e.g., human and non-human primates such as monkey), rabbit, and rodents (e.g., mouse and rat). In some embodiments, the individual or subject is human.

As used herein, the term "administering", "administration" or "administered" refers to the physical introduction of a composition comprising a therapeutic agent (e.g., anti-TNFR2 antibody) to a subject, using any of the various methods and delivery systems known to those skilled in the art. Routes of administration include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. Other non-parenteral routes include a topical, epidermal or mucosal route of administration, for example, intranasally, vaginally, rectally, sublingually or topically.

By "sample" from subject/patient is meant a collection of cells or fluids obtained from a cancer patient or cancer subject. The source of the tissue or cell sample may be solid tissue as from a fresh, frozen and/or preserved organ or tissue sample or biopsy or aspirate; blood or any blood constituents; bodily fluids such as cerebrospinal fluid, amniotic fluid, peritoneal fluid, or interstitial fluid; cells from any time in gestation or development of the subject. The tissue sample may contain compounds which are not naturally intermixed with the tissue in nature such as preservatives, anticoagulants, buffers, fixatives, nutrients, antibiotics, or the like. Examples of tumor samples herein include, but are not limited to, tumor biopsy, fine needle aspirate, bronchiolar lavage, pleural fluid, sputum, urine, a surgical specimen, circulating tumor cells, serum, plasma, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples.

Antibody of the Invention

In one embodiment of the invention, the amino acid change described herein includes amino acid substitution, insertion, or deletion. Preferably, the amino acid change described herein is amino acid substitution, preferably conservative substitution.

In a preferred embodiment, the amino acid change described herein occurs in region(s) outside the CDRs (e.g., in FRs). In one embodiment, the amino acid change occurs in FR region(s) of the HCVR or LCVR, preferably LCVR, e.g., in FR1, FR2, FR3 and/or FR4 of the LCVR. In some embodiments, there is one, two or three changes in the FR region. In a particular embodiment, the change is at Q38 of FR1, e.g., a substitution from Q to H or its conservative amino acid at position 38.

More preferably, the amino acid change described herein occurs in region(s) outside the heavy chain variable region and/or outside the light chain variable region.

In some embodiments, the substitution is a conservative substitution. A conservative substitution refers to a replacement of an amino acid by another amino acid of the same class, e.g., an acidic amino acid replacement by another acidic amino acid, a basic amino acid replacement by another basic amino acid, or a neutral amino acid replacement by another neutral amino acid. Exemplary substitutions are shown in Table below:

| Original residue | Conservative substitution | Preferable conservative substitution |
| --- | --- | --- |
| Ala (A) | Val, Leu, Ile | Val |
| Arg (R) | Lys, Gln, Asn | Lys |
| Asn (N) | Gln, His, Asp, Lys, Arg | Gln |
| Asp (D) | Glu, Asn | Glu |
| Cys (C) | Ser, Ala | Ser |
| Gln (Q) | Asn, Glu | Asn |
| Glu (E) | Asp, Gln | Asp |
| Gly (G) | Ala | Ala |
| His (H) | Asn, Gln, Lys, Arg | Arg |
| Ile (I) | Leu, Val, Met, Ala, Phe, Norleucine | Leu |

-continued

| Original residue | Conservative substitution | Preferable conservative substitution |
| --- | --- | --- |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Trp, Leu, Val, Ile, Ala, Tyr | Tyr |
| Pro (P) | Ala | Ala |
| Ser (S) | Thr | Thr |
| Thr (T) | Val, Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Optionally, the anti-TNFR2 antibody of the invention comprises post-translational modifications to the light chain variable region, the heavy chain variable region, the light chain, or the heavy chain. Exemplary post-translational modifications include disulfide bond formation, glycosylation, PEGylation, lipidation, acetylation, phosphorylation, or any other operations, such as conjugation with a labeling component.

In certain embodiments, the antibody provided herein is altered to increase or decrease the extent to which the antibody is glycosylated. Addition or deletion of glycosylation sites to an antibody can be conveniently achieved by altering the amino acid sequence such that one or more glycosylation sites are created or removed.

Another modification encompassed by the invention to the antibody or the fragment thereof described herein is PEGylation. An antibody can be PEGylated to, e.g. increase the biological (e.g., serum) half-life of the antibody. To PEGylate an antibody, the antibody or the fragment thereof typically reacts with polyethylene glycol (PEG) (such as a reactive ester or aldehyde derivative of PEG) in a condition where one or more PEG groups become attached to the antibody or antibody fragment.

In certain embodiments, one or more amino acid modifications can be introduced into an Fc region of an antibody provided herein, thereby producing an Fc region variant such that, for example, the efficacy of the antibody in treating cancer or a cell proliferative disease is enhanced. For example, modification can be incorporated to eliminate or increase the ADCC function of the antibody, or to eliminate the binding of the antibody to Fc γ Receptor. In an embodiment, L234A, L235A, D265A and/or P329A (EU numbering), or L234A/L235A/D265A/P329A (EU numbering) can be incorporated into Fc region.

In one embodiment, the number of cysteine residues of an antibody can be altered to modify antibody properties.

In one embodiment, one or more amino acid modifications can be introduced to FR region to improve the production of the antibodies, e.g., to improve the expression of the antibodies in the cells or to improve the purity of the produced antibodies. For example, there can be modifications in FR1, FR2, FR3 or FR4 regions, e.g., FR1 regions, e.g., at position Q38. Specifically, the modification can be substitution from I at position 38 to H or its conservative amino acid.

In some embodiments, the anti-TNFR2 antibody or the antigen-binding fragment thereof of the invention exhibits the same or similar binding affinity and/or specificity as the antibody hu32-C, hu32C-V1 or hu3-E of the present invention; and/or inhibits (e.g., competitive inhibition) the binding of the antibody hu32-C, hu32C-V1 or hu3-E of the present invention to TNFR2 and/or binds the same or overlapping epitope as the antibody hu32-C, hu32C-V1 or hu3-E of the present invention; and/or competes with the antibody hu32-C, hu32C-V1 or hu3-E of the present invention for binding to TNFR2; and/or has one or more biological characteristics of the antibody hu32-C, hu32C-V1 or hu3-E of the present invention.

Nucleic Acid of the Invention and Host Cell Comprising Same

In one aspect, the invention provides a nucleic acid encoding any of the above anti-TNFR2 antibodies or fragments thereof. The nucleic acid can encode an amino acid sequence comprising the light chain variable region and/or the heavy chain variable region of the antibody, or an amino acid sequence comprising the light chain and/or the heavy chain of the antibody.

In one embodiment, an exemplary nucleic acid of the invention includes a nucleic acid encoding an amino acid sequence selected from any one of SEQ ID NOs: 7, 8, 15, 16, 25, 26, 28, 37, 38, or a nucleic acid encoding an amino acid sequence having at least 85%, 90%, 91%, 92%, 93%, 94%, 95%, 96%, 97%, 98%, or 99% identity to an amino acid sequence selected from any one of SEQ ID NOs: 7, 8, 15, 16, 25, 26, 28, 37, 38.

In another embodiment, the nucleic acid of the present invention comprises nucleotide sequences selected from anyone of SEQ ID NO:23, 24, 27, 35 or 36, or a nucleotide sequences having at least 85%, 90%, 91%. 92%, 93%, 94%, 95%. 96%, 97%. 98%, or 99% identity to an nucleotide sequence selected from any one of SEQ ID NO:23, 24, 27, 35 or 36.

In one embodiment, one or more vectors containing anyone of the nucleic acid are provided. In one embodiment, the vector is an expression vector, such as an eukaryotic expression vector. The vector includes, but is not limited to, a virus, a plasmid, a cosmid, a lambda phage or a yeast artificial chromosome (YAC). Numerous vector systems can be used. In a preferred embodiment, the expression vector of the present invention is a pCDNA, e.g., pCDNA3.1 expression vector.

In one embodiment, the present invention provides a host cell containing a nucleic acid encoding the region of antibody described herein or the vector described herein. Suitable host cells for cloning or expressing the nucleic acid encoding the antibody or the vector include prokaryotic or eukaryotic cells as described herein. The antibody can be produced, for example, in bacteria. After expression, the antibody can be isolated from bacterial paste in soluble fraction and can be further purified. In one embodiment, the host cell is E. coli.

In another embodiment, the host cell is eukaryotic. The host cell can be selected from the group consisting of yeasts, mammalian cells (e.g., a human cell), insect cells, plant cells, or other cells suitable for preparation of an antibody or an antigen-binding fragment thereof. For example, eukaryotic microorganisms such as filamentous fungi or yeast are suitable cloning or expression hosts for the vector encoding the antibody, including fungus and yeast strains. Examples of useful mammalian host cell lines are monkey kidney CV1 lines (COS-7) transformed with SV40, human embryonic kidney lines (293HEK or 293 or 293T cells) and the like. Other useful mammalian host cell lines include Chinese hamster ovary (CHO) cells, and myeloma cell lines such as Y0, NS0, and Sp2/0.

Method for Preparing and Purifying Antibody or Antigen-Binding Fragment Thereof of the Present Invention In one embodiment, the present invention provides a method for preparing an anti-TNFR2 antibody, wherein the method comprises steps of incubating host cells containing an nucleic acid encoding the antibody or antigen binding fragment of the present invention (anyone or more regions or chains of the antibody), under conditions suitable for expressing antibodies or the antigen binding fragments, and optionally, recovering the antibody or the fragments from the host cells (or the host cell cultures).

For recombinant production of the antibody, a nucleic acids encoding the antibody (e.g., the nucleic acids encoding VH or VL or the heavy chain or the light chain) is isolated and inserted into one or more vectors for further cloning and/or expression in the host cells. The nucleic acid is readily isolated and sequenced by using conventional procedures (e.g., by using oligonucleotide probes that are capable of binding specifically to genes encoding heavy and light chains of antibodies).

In one embodiment, the host cell contains a vector including a nucleic acid encoding an amino acid sequence of a VL of the antibody and a nucleic acid encoding an amino acid sequence of a VH of the antibody. In one embodiment, the host cell contains a first vector comprising a nucleic acid encoding an amino acid sequence of a VL of the antibody and a second vector comprising a nucleic acid encoding an amino acid sequence of a VH of the antibody.

Antibody molecules prepared as described herein can be purified by known techniques such as high performance liquid chromatography, ion exchange chromatography, gel electrophoresis, affinity chromatography (e.g., protein A), size exclusion chromatography, and the like. The actual conditions used to purify a particular protein also depend on factors such as net charge, hydrophobicity, and hydrophilicity, and these will be apparent to those skilled in the art. The purity of the antibody molecule of the present invention can be determined by any of a variety of well-known analysis methods including size exclusion chromatography, gel electrophoresis, high performance liquid chromatography, and the like.

Assay

The anti-TNFR2 antibody provided herein can be identified, screened, or characterized for its physical/chemical properties and/or biological activity through a variety of assays known in the art. In one aspect, the antigen-binding activity of the antibody of the invention is tested, for example, by known methods such as ELISA, Western blotting, flow cytometry, and magnetic beads coated with antibody molecules.

In another aspect, a competitive binding assay can be used for identifying an antibody that competes for binding to TNFR2 with any of the anti-TNFR2 antibodies disclosed herein. In some embodiments, such competitive antibodies bind to the same epitope (e.g., a linear or conformational epitope) as any of the anti-TNFR2 antibodies of the present invention.

The invention further provides an assay for identifying an anti-TNFR2 antibody having one or more of the properties described above. Further provided is an antibody having such biological activities in vivo and/or in vitro.

In some embodiments, the antibody of the invention is tested for one or more of the properties described above.

Cells for use in any of said in-vitro assays include cells or cell lines that naturally express TNFR2 or that are engineered to express TNFR2. In one embodiment, the cells are 293 or 293T cell lines or T cells.

It will be appreciated that any of said assays can be performed by using the immunoconjugate of the invention in place of or in addition to the anti-TNFR2 antibody.

It will be appreciated that any of said assays can be performed by using the anti-TNFR2 antibody and other agents.

Immunoconjugate

In some embodiments, the present invention provides an immunoconjugate comprising any anti-TNFR2 antibody or the antigen-binding fragment thereof provided herein and other agent(s), such as therapeutic agents, including a chemotherapeutic agent, other antibody, cytotoxic agent, vaccine, anti-infection agents, small molecular entity, or immunomodulator (e.g., anti-inflammatory agents or immunosuppressive agents). In one embodiment, the other agent such as cytotoxic agent includes any agents that are harmful to cells. In some embodiments, the immunoconjugate is used to diagnose, prevent or treat cancer or infection.

Pharmaceutical Composition, Formulation or Combination Product

The invention further provides a pharmaceutical composition, or a pharmaceutical formulation, or combination product comprising an anti-TNFR2 antibody or antigen-binding thereof or an immunoconjugate thereof, or the nucleic acid encoding the anti-TNFR2 antibody or the fragment thereof.

Such composition, formulation or combination product may further contain suitable pharmaceutical adjuvants such as a pharmaceutical carrier, an excipient, and the like known in the art, including buffers.

The pharmaceutical carrier suitable for use in the invention can be sterile liquid, such as water and oil, including petroleum, or oil of animal, vegetable, or synthetic source, e.g., peanut oil, soybean oil, mineral oil, sesame oil, and the like. Water is a preferred carrier when the pharmaceutical composition is administered intravenously. Saline solutions and aqueous dextrose and glycerol solutions can also be employed as liquid carriers, particularly used for injectable solutions.

Suitable excipients includes starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like.

The composition may further contain a small quantity of wetting agent or emulsifier, or pH buffer, if desired.

For uses of pharmaceutical adjuvants, see "Handbook of Pharmaceutical Excipients", the eighth edition, R. C. Rowe, P. J. Seskey and S. C. Owen, Pharmaceutical Press. London, Chicago.

The compositions may take the form of a solution, a suspension, an emulsion, a tablet, a pill, a capsule, a powder, a sustained release preparation, and the like.

The composition of the present invention may be in various forms. These forms include, for example, liquid, semi-solid, and solid forms, such as liquid solutions (e.g., injectable solutions and infusible solutions), dispersions or suspensions, liposomes, and suppositories. The preferred form depends on the intended mode of administration and therapeutic use. Commonly preferred are in the form of injectable solutions or infusible solutions. The preferred mode of administration is parenteral (eg, intravenous, subcutaneous, intraperitoneal (i.p.), intramuscular) injection or infusion. In a preferred embodiment, the antibody molecule is administered by intravenous infusion or injection. In another preferred embodiment, the antibody molecule is administered by intramuscular, intraperitoneal or subcutaneous injection.

The antibody or the antigen-binding fragment thereof of the present invention having the desired purity can be mixed with one or more optional pharmaceutical adjuvants to prepare pharmaceutical formulations of the antibody of the present invention. The pharmaceutical formulation is preferably in the form of a lyophilized preparation or an aqueous solution.

The pharmaceutical composition or formulation of the invention may also contain more than one active ingredient required by a particular indication to be treated, preferably active ingredients having complementary activities without adversely affecting one another. For example, it is desirable to further provide other therapeutic agents, e.g., a chemotherapeutic agent, other antibody, cytotoxic agent, vaccine, anti-infection agents, small molecular entity, or immunomodulator. The active ingredients are suitably combined in an amount effective for an intended purpose. The active ingredients may be any substance known in the art and capable of being combined with an anti-TNFR2 antibody. In one embodiment, the other antibody is PD-1 antibody or PD-L1 antibody, e.g. human PD-1 antibody or human PD-L1 antibody.

A sustained release preparation can be prepared. Suitable examples of the sustained release preparation include a semipermeable matrix of a solid hydrophobic polymer containing an antibody, the matrix is in the form of a shaped article, e.g., a film or a microcapsule.

The present invention further provides a combination product, comprising the anti-TNFR2 antibody or the antigen binding fragment thereof of the present invention, and other therapeutic agents, e.g., a chemotherapeutic agent, other antibody, cytotoxic agent, vaccine, anti-infection agents, small molecular entity, or immunomodulator. In one embodiment, the other antibody is PD-1 antibody or PD-L1 antibody.

Use and Method

In one aspect, the present invention provides a method for modulating an immune response in a subject.

In another aspect, the present invention provides a method for activating T cells or inducing T cell mediated antitumor activity. In one embodiment, the T cells are the CD4+ T cells or CD8+ T cells.

In one embodiment, the activation of the T cells includes stimulating the cytokine secretion of the T cells. e.g., the IFN-gamma secretion of T cells.

In another embodiment, the activation of T cells includes stimulating the proliferation of T cells.

In another aspect, the invention relates to a method for preventing or treating a tumor (e.g., cancer) in a subject. In some embodiments, the tumor is a tumor immune escape.

In one embodiment, the cancer patient has increased level of TNFR2 protein expression, or increased level of nucleic acid encoding TNFR2 protein.

In some embodiments, the tumor, such as cancer, includes solid tumors and hematological tumors and metastatic lesions. In one embodiment, examples of solid tumors include malignant tumors. The cancer can be early, middle, or advanced or metastatic cancer. In some embodiments, the tumor is a tumor that requires T cell activation, such as cancer, for example, a tumor or cancer with T cell dysfunction.

Preferably, said cancer is non-small cell lung cancer, breast cancer, renal cell carcinoma, Hodgkin lymphoma, multiple myeloma, cutaneous non-Hodgkin lymphoma, and ovarian cancer, cancer in gastrointestinal tract, e.g., colorectal cancer, rectal cancer or colon cancer.

In some embodiments, the tumor therapy will benefit from
  (i) inhibition of TNFR2 nucleic acid or protein levels;
  (ii) blocking the binding of TNFR2 to its ligand, such as TNF-alpha,
  (iii) the activation of T cells, e.g., increasing the secretion of cytokine like IFN-gamma, increasing the proliferation of CD4+ T cells or CD8+ T cells;
  (iv) a combination of anyone or more of the above.

In another aspect, the invention relates to a method for preventing or treating an infectious disease in a subject.

In some embodiments, the infection is acute or chronic. In some embodiments, the chronic infection is a persistent infection, a latent infection or a slow infection. In some embodiments, the chronic infection is caused by a pathogen selected from the group consisting of bacteria, viruses, fungi, and protozoa.

In some embodiments, the methods above comprise administering the antibody or antigen binding fragments, the immunoconjugate, the pharmaceutical composition or formulation, the combination product or the nucleic acid of the present invention.

In some embodiments, the methods above further comprises administering to said subject in combination with one or more therapies, e.g., a therapeutic modality and/or other therapeutic agent, preferably the therapeutic modality includes surgery and/or radiation therapy, and/or the other therapeutic agent is selected from the group consisting of a chemotherapeutic agent, other antibody, cytotoxic agent, vaccine, anti-infection agents, small molecular entity, or immunomodulator.

In one embodiment, the modulator includes immunosuppressive agents or anti-inflammatory agents.

In one embodiment, the antibody can be antibodies binding to immune checkpoint molecules. In one embodiment, the other antibody is PD-1 antibody or PD-L1 antibody.

In some embodiments, the antibody combinations described herein can be administered separately, for example, as separate antibodies, or linked (for example, as a bispecific or tri-specific antibody molecule).

Such combination therapy encompasses combined administration (e.g., two or more therapeutic agents are contained in the same formulation or separate formulations), and separate administration. In one embodiment, the administration of the antibodies of the invention occurs before, at the same time, and/or after the administration of the other one or more therapies.

The subject can be a mammal, e.g., a primate, preferably a higher primate, e.g., a human (e.g., a patient having or at risk of having the disease described herein). In one embodiment, the subject is in need of an enhanced immune response. In some embodiments, the immune response is an anti-tumor response.

In one embodiment, the subject has or is at risk of having the disease described herein (e.g., the tumor or infectious disease as described herein).

In other aspects, the invention provides uses of the anti-TNFR2 antibody or the fragment thereof or the immunoconjugate thereof in manufacture or preparation of a medicine for the above use, e.g., prevention or treatment of the above-mentioned related diseases or conditions.

EXAMPLES

Example 1 Generation of TNFR2 Binding Antibody by Hybridoma Screening

Five SJL (Charles River) mice were immunized by alternating injections of hTNFR2-mFc protein (SEQ ID NO:45) and CHO-K1 cell line expressing human TNFR2 (SEQ ID NO:48). Four cycles of immunization were achieved through alternate injections of the proteins and the cells every 2 weeks according to the immunization schedule in Table 1. The blood of the immunized mice after the $2^{nd}$, $3_{rd}$ and $4^{th}$ immunizations were tested by ELISA against TNFR2 protein HuTNFR2-huFc (SEQ ID NO:46) and FACS against 293T cell line stably expressing human TNFR2 (SEQ ID NO:48).

TABLE 1

Immunization schedule

| Procedure | Route | Dosage |
| --- | --- | --- |
| Primary immunization | s.c. | 50 µg hTNFR2-mFc protein per animal |
| $2^{nd}$ boost | i.p. | 25 µg hTNFR2-mFc protein per animal |
| $3^{rd}$ boost | s.c. | 5 * $10^6$ CHO-K1-huTNFR2 cells per animal |
| Final boost | i.p. | 25 µg hTNFR2-mFc protein per animal |

The mouse 5 # was chosen as the splenocyte source for the following fusion step according to the results of ELISA and FACS. The results indicated that serum from mouse 5 # had the strongest ability to inhibit TNF-α (ACRO Biosystem, Cat #TNA-H5228)'s binding to TNFR2 in cell-blocking assay.

One electro fusion was performed. Fused cells were plated on 96-well plates. The positive clone is screened by ELISA and FACS. Human TNFR1 protein (Acro Biosystem, Cat #TN1-H5222), Human LTBR (ACRO Biosystem, Cat #LTR-H5251), Human Osteoprotegerin (ACRO Biosystem. Cat #TNB-H5220) were used for counter screen. Positive clones were expanded into 24-well plates. Supernatants were collected for further confirming the screening. According to the results, 15 clones were selected for sequencing. Example 4 specified the specific procedures of the screening.

Example 2 Sequencing of Hybridoma and Corresponding Sequences

The sequences of the mouse anti-human TNFR2 antibody light chain and heavy chain variable regions were obtained by the polymerase chain reaction (PCR) amplification technique. Total RNA from 15 antibodies was isolated using RNAprep pure Cell Kit (TIANGEN, Cat #DP430) and cDNA was synthesized using Fast King gDNA Dispelling RT Super Mix (TIANGEN, Cat #KR118). The heavy chain and light chain variable region were cloned by PCR. All PCRs were carried out using high fidelity polymerase. The DNA for each antibody amplified by PCR was cloned into TA cloning vector for sequencing by GENEWIZ Inc.

The amino acid sequences of the variable regions of the mouse antibody clone 32A1D5 and 43B7A4 are as follows:
>32A1D5 heavy chain variable region (32A1D5-VH): SEQ ID NO:7
>32A1D5 light chain variable region (32A1D5-VL): SEQ ID NO:8
>43B7A4 heavy chain variable region (43B7A4-VH): SEQ ID NO:15
>43B7A4 light chain variable region (43B7A4-VL): SEQ ID NO: 16.

Example 3 Chimeric Antibody Expression and Purification

Method to produce 15 chimeric IgG1 antibodies was established. After sequence analysis, the variable regions of the chimeric antibodies were generated by gene synthesis (Genscript) based on the sequence above. The light chain variable region is inserted into the expression vector pcDNA3.1 containing a nucleic acid encoding a light chain constant region represented by SEQ ID NO:42 (SEQ ID NO:41) to construct the vectors expressing the light chain of the antibody, and the heavy chain variable region is inserted into the expression vector pcDNA3.1 (Invitrogen) containing a nucleic acid encoding a heavy chain constant region represented by SEQ ID NO:40 (SEQ ID NO:39) to construct the vectors expressing the heavy chain of the antibody. The plasmid was extracted using EndoFree Midi Plasmid Kit (TIANGEN, Cat #DP108). Moreover, and the heavy and light chain vectors were co-transfected into CHO-S cells using ExpiCHO™ Expression System (ThermoFisher, Cat #A29133) at a ratio of 1:1 according to manufacturer's instructions. The transfected cells were cultured in ExpiCHO™ Expression Medium for 12 days, and then culture supernatants were harvested and sent for purification with Protein A affinity chromatography (GE healthcare).

All 15 clones were tested in Size Exclusion Chromatography. 20 µg of sample from each clone was injected into a TSK G3000SWXL column using 100 mM sodium phosphate+100 mM $Na_2SO_4$, pH 7.0, as running buffer. The run time was 30 min. All measurements were performed on Waters e2695 HPLC. Data was analyzed using OpenLAB software. Main peak of the 13 clones are above 95% in SEC, suggesting high purity and integrity of the purified chimeric antibody.

Example 4 Screening and Identification of Chimeric Antibody

All 15 chimeric antibodies were further tested by ELISA binding, cell blocking. The antibodies were also tested for its non-specific binding to TNFR2 negative cells, which shows that the antibodies do not bind to cells without human TNFR2 expression on cell surfaces.

Anti-TNFR2 Antibodies Bound to Human/Cynomolgus TNFR2 Protein

Human TNFR2, human Fc tag protein (huTNFR2-huFc, SEQ ID NO:46) or Cynomolgus TNFR2, human Fc tag protein (cyno-TNFR2-huFc, SEQ ID NO:47) was immobilized onto 96-well plates (Hangzhou Xinyou, Cat #100096H) by incubation in PBS(Hyclone, Cat #SH30256.01) overnight at 4° C. The plates were then blocked by incubation with 1% BSA in PBS for one hour at 37° C. After blocking, the plates were washed three times with PBST (PBS containing 0.05% Tween20). Serially diluted anti-TNFR2 antibodies obtained in Example 3, and negative control IgG (heavy chain: SEQ ID NO:43, Light chain: SEQ ID NO:44, WO2008068246A1) were prepared in the dilution buffer (PBS containing 0.05% Tween 20 and 0.5% BSA) and incubated with the immobilized proteins above for one hour at 37° C. in the dilution buffer. Then, the plates were washed three times with PBST, incubated for one hour at 37° C. with Peroxidase AffiniPure Goat Anti- Human IgG, F(ab')2 fragment specific (Jackson ImmunoResearch, Cat #109-035-097) diluted 1/20.000 in the dilution buffer, and then washed with PBST again. 50 μL/well TMB (Thermo, Cat #34028) was added into plates, after 15 minutes, reaction was stopped with 1M $H_2SO_4$. The absorbance at 450 nm-620 nm was determined. The $EC_{50}$ and representative binding curves for the clones' binding to human/cynomolgus TNFR2 were shown in FIG. 1.

The results indicated that two chimeric antibodies 32A1D5 and 43B7A4 could bind to human (with $EC_{50}$ 0.04820 nM and 0.06272 nM respectively) and cynomolgus TNFR2 proteins (with $EC_{50}$ 0.008201 nM and 0.008974 nM).

Anti-TNFR2 Antibodies Bound to Cynomolgus TNFR2 Expressed on the Cell Surface of 293T Cells A cell based binding assay was established to determine whether anti-human TNFR2 antibodies of the present invention could bind to cynomolgus monkey TNFR2 expressed on the cell surface. 293T cell line was transfected with nucleotide encoding the cynomolgus monkey TNFR2 protein (SEQ ID NO:49) using Lipofectamine™ 2000 Transfection Reagent (Invitrogen, Cat #11668019). A cell pool highly expressing cynomolgus monkey TNFR2 was selected after screening the cells using Puromycin Dihydrochloride (Gibco, Cat #A1113802). The eight-point series dilutions of anti-TNFR2 antibody 32A1D5 (series dilution, the concentrations started from 20 μg/mL and 4-fold diluted) were added to cells and the obtained mixtures were incubated in PBS at 4° C. for 30 minutes. Then the cells were washed with PBS twice. The binding activity of the anti-TNFR2 antibody to cynomolgus TNFR2 expressed on 293T cells was detected using an R-PE-conjugated AffiniPure Goat Anti-Human IgG. Fcγ Fragment Specific (Jackson ImmunoResearch, Cat #109-116-098) as secondary reagent, wherein the mixture was incubated at 4° C. for 30 minutes followed by being washed twice with PBS. Then, cells were re-suspended in PBS. Analysis of TNFR2 binding was carried out with the BD Accuri C5 flow cytometer (BD Bioscience). The results were shown in FIG. 2A.

The results showed that the antibody 32A1D5 specifically bound to cynomolgus monkey TNFR2 expressed on the cell surface, with $EC_{50}$ of 0.9682 nM.

Anti-TNFR2 Antibody Blocked TNF-α's Binding to Human TNFR2 Expressed on Cell Surface of 293T Cells.

A cell based assay is performed to determine whether anti-human TNFR2 antibody of the present invention could block TNF-α's binding to human TNFR2 expressed on cell surface. 293T cell line was transfected with the nucleotide molecule encoding human TNFR2 protein (SEQ ID NO:48) using Lipofectamine™ 2000 Transfection Reagent (Invitrogen, Cat #11668019). A cell clone highly expressing human TNFR2 was selected after screening using Puromycin Dihydrochloride (Gibco, Cat #A1113802). The eight-point series dilutions of anti-TNFR2 antibodies (32A1D5 and 43B7A4) with the concentrations started from 20 μg/mL and 4-fold diluted were added to cells and the mixtures were incubated in PBS at 4° C. for 30 minutes. Then the cells were incubated with 50 μg/mL Biotin-TNF-α (ACRO Biosystems, Cat #TNA-H8211) at 4° C. for 30 minutes follow by being washed twice with PBS. The binding of the Biotin-TNF-α to human TNFR2 expressed on the surface of 293T cells was detected using an PE-Streptavidin (Biolegend, Cat #405203) as secondary reagent, wherein the mixture was incubated in PBS at 4° C. for 30 minutes followed by being washed twice with PBS. Then, cells were re-suspended in PBS. Analysis of Biotin-TNF-α binding was carried out with the BD Accuri C5 flow cytometer (BD Bioscience). The results were shown in FIG. 2B (for 32A1D5) and FIG. 2C (for 43B7A4).

The results showed that the two chimeric antibodies could block the binding of TNFR2 expressed on the cell surface to TNF-α.

Example 5 Generation and Characterization of Humanized Antibodies

The two chimeric antibodies 32A1D5 and 43B7A4 were subjected for humanization respectively. The sequences of the variable domains of mouse antibodies were used to identify the human germline sequence having the highest homology to the murine framework. CDR grafting and back mutation were taken in humanization.

32A1D5 Humanization

The antibodies were humanized by inserting the 6 CDRs into the most appropriate human germline framework sequences according to IMGT database (www.imgt.org). Human germline framework sequence IGKV1-27*01 for light chain and IGHV2-5*09 for heavy chain were used for CDR grafting, respectively. Variant heavy chain variable regions (VH/HCVR) Hu32-H1 and Hu32-H2 were obtained by grafting the three CDRs to the germline sequence, and back mutation of S30N was made on the HCVR for Hu32-H2.

>IGHV2-5*09 (Germline sequence for 32A1D5 VH)

(SEQ ID NO: 63)
QVTLKESGPTLVKPTQTLTLTCTFSGFSLSTSGVGVGWIRQPPGKALEWL

ALIYWDDDKRYGPSLKSRLTITKDTSKNQVVLTMTNMDPVDTATYYCA

HRYYYYYGMDVWGQGTTVTVSS

>Hu32-H1 VH sequence: SEQ ID NO:25

>Hu32-H2 VH sequence:

(SEQ ID NO: 64)
QVTLKESGPTLVKPTQTLTLTCTFSGFSLNTLGMGVGWIRQPPGKALEWL

AHIWWDADKYYNPALKSRLTITKDTSKNQVVLTMTNMDPVDTATYYCA

RMTGTRYFDVWGQGTTVTVSS

Variant light chain variable regions (LCVR/VL) Hu32-L1, Hu32-L2, Hu32-L3 and Hu32-L2V were obtained by grafting the three CDRs to germline sequence, and back mutations of Q38H, Y49H, T69S, F71Y and V83I for Hu32-L2, back mutations of Y49H, T69S, and F71Y for Hu32-L3, and back mutations of Q38H, Y49H, T69S, and F71Y for Hu32-L2V were made on LCVR respectively.

>IGKV1-27*01 (Germline sequence for 32A1D5 VL)

(SEQ ID NO: 65)
DIQMTQSPSSLSASVGDRVTITCRASQGISNYLAWYQQKPGKVPKLLIYA

ASTLQSGVPSRFSGSGSGTDFTLTISSLQPEDVATYYCQKYNSAPLTFGGG

TKVEIK

>Hu32-L1

(SEQ ID NO: 66)
DIQMTQSPSSLSASVGDRVTITCKASQNINKFIAWYQQKPGKVPKLLIYYT

STLQPGVPSRFSGSGSGTDFTLTISSLQPEDVATYYCLQYGVLWTFGGGT

KVEIK

>Hu32-L2

(SEQ ID NO: 67)
DIQMTQSPSSLSASVGDRVTITCKASQNINKFIAWYQHKPGKVPKLLIHYT

STLQPGVPSRFSGSGSGSDYTLTISSLQPEDIATYYCLQYGVLWTFGGGTK

VEIK

>Hu32-L3: SEQ ID NO:26
>Hu32-L2V: SEQ ID NO:28.

43B7A4 Humanization

Human germline framework sequence IGKV3D-7*01 for light chain and IGHV1-18*01 for heavy chain were used for CDR grafting, respectively.

Variant heavy chain variable region (HCVR/VH) Hu3-H1, Hu3-H2 and Hu3-H3 were obtained by grafting the three CDRs to the germline sequence, back mutations of V2I, V67F, M69F, T71 L for Hu3-H1, V2I, M69F, T71 L for Hu3-H2, and V2I, V67F, T68A, M69F, T71 L for Hu3-H3 were made on HCVR respectively.

>IGHV1-18*01 (Germline sequence for 43B7A4 VH)

(SEQ ID NO: 68)
QVQLVQSGAEVKKPGASVKVSCKASGYTFTSYGISWVRQAPGQGLEWM

GWISAYNGNTNYAQKLQGRVTMTTDTSTSTAYMELRSLRSDDTAVYYC

ARYFDYWGQGTLVTVSS

>Hu3-H1

(SEQ ID NO: 69)
QIQLVQSGAEVKKPGASVKVSCKASGYTFTTYGMSWVRQAPGQGLEWM

GWIHTYSGVPTYADDFKGRFTFTLDTSTSTAYMELRSLRSDDTAVYYCA

RGLYGVDYWGQGTLVTVSS

>Hu3-H2

(SEQ ID NO: 70)
QIQLVQSGAEVKKPGASVKVSCKASGYTFTTYGMSWVRQAPGQGLEWM

GWIHTYSGVPTYADDFKGRVTFTLDTSTSTAYMELRSLRSDDTAVYYCA

RGLYGVDYWGQGTLVTVSS

>Hu3-H3: SEQ ID NO:37

Variant light chain variable region (LCVR/VL) Hu3-L1 and Hu32-L2 were obtained by direct grafting the three CDRs to germline sequence, back mutations of G68A for Hu3-L1, and I58V, A60D, S63T, G68A for Hu3-L2 were made on LCVR respectively.

>IGKV3D-7*01 (Germline sequence for 43B7A4 VL)

(SEQ ID NO: 71)
EIVMTQSPATLSLSPGERATLSCRASQSVSSSYLSWYQQKPGQAPRLLIY

GASTRATGIPARFSGSGSGTDFTLTISSLQPEDFAVYYCQQDYNLPYTFG

QGTKLEIK

>Hu3-L1: SEQ ID NO:38
>Hu3-L2

(SEQ ID NO: 72)
EIVMTQSPATLSLSPGERATLSCKASENVVTYVSWYQQKPGQAPRLLIYG

ASNRYTGVPDRFTGSGSATDFTLTISSLQPEDFAVYYCGQSYTYPYTFGQ

GTKLEIK

The DNAs of above heavy chain and light variable regions were synthesized and subcloned into an expression vector pcDNA3.1 (Invitrogen), containing nucleotide (SEQ ID NO:39) encoding human IgG1 heavy chain constant region (SEQ ID NO:40, Accession #P01857) and pcDNA3.1 containing nucleotide (SEQ ID NO:41) encoding human kappa light chain constant region (SEQ ID NO:42, Accession #P01834), respectively. The Plasmid was extracted using EndoFree Midi Plasmid Kit (TIANGEN, Cat #DP108). The expression and purification of the antibodies follows the procedures as described in Example 3.

The humanized antibody hu32-C comprises the VH Hu32-H1 and the VH Hu32-L3, and the humanized antibody hu3-E comprises the VH Hu3-H3 and the VL Hu3-L1. The variant of hu32-C, hu32C-V1 comprises the VH Hu32-H 1 and the VLHu32-L2V.

Example 6 Evaluation of Anti-Tnfr2 Humanization Antibodies

The preliminary evaluation is in accordance with the screening and identification procedures of the chimeric antibodies, including ELISA binding, ELISA blocking, cell blocking, as described in Example 4. Based on these results, humanized antibodies hu32-C and hu3-E were selected for further in vitro and in vivo functional evaluation.

The ELISA binding assay is performed in consistent with EXAMPLE 4, with the exceptions that the anti-TNFR2 antibodies are hu32-C and hu3-E, the coated protein was replaced by human TNFR2, mouse Fc-tag (SEQ ID NO:45).

The results of humanized antibodies' binding to human TNFR2 protein can be seen in FIG. 3A (hu32-C) and FIG. 3B (hu3-E).

The results showed the two humanized antibodies both can specifically bind to human TNFR2, with the $EC_{50}$ of 0.06970 nM (hu32-C) and 0.05079 nM (hu3-E).

Anti-TNFR2 Antibodies Blocked the Interaction Between TNFR2 and TNF-α

High-binding clear polystyrene 96-well plates were coated with 50 μL/well of 1 μg/mL human TNF-α protein, his tag (Acro Biosystem, Cat #TNA-H5228) in carbonate buffer and incubated overnight at 4° C. Then plates were washed once on an automatic plate washer using washing buffer (PBS+0.05% Tween 20). 200 μL of blocking buffer (PBS+1% BSA) was added to each well and incubated for 1 hour at room temperature. The serial diluted antibodies (hu32-C and hu3-E), and negative control IgG diluted by dilution buffer (PBS+0.5% BSA+0.05% Tween 20) (starting concentration: 20 μg/mL (Concentration before mixing), 4 fold dilution) were prepared and mixed in a volume ratio of 1:1 with 0.1 µg/mL (Concentration before mixing) hTNFR2-mFc (SEQ ID NO:45), then the mixed dilutions were added into the 96-well plate and incubated in the dilution buffer (PBS containing 0.05% Tween 20 and 0.5% BSA) for 1 hour at RT. The plates were washed twice with washing buffer on an automatic plate washer. 50 µL/well of HRP conjugated Goat anti-mouse Fc antibody (Jackson Immunoresearch, Cat #115-035-164) in the dilution buffer was then added to each well of the plate. After that, the ELISA plates were incubated for 60 min at RT, then the plates were washed twice with 250 µL/well washing buffer. Finally. 50 µL/well of TMB was added to each well and the reaction was terminated using 1 M $H_2SO_4$. The absorbance at 450 nm-620 nm was determined.

The results of blocking human TNFR2 binding to TNFα by humanized antibodies can be seen in FIG. 3 A (hu32-C) and FIG. 3B (hu3-E).

The results showed the two humanized antibodies could block the TNFR2's binding to TNF-α.

The ability of the humanized antibodies for binding to cynomolgus TNFR2 on cell surface and blocking TNF-α's binding to human TNFR2 on cell surface was also examined. The assay procedures were consistent with EXAMPLE 4. The results of cell-based assay were shown in FIG. 4.

The results of cell-based assay showed that humanized antibodies hu32-C and hu3-E both had the ability of binding to TNFR2 and blocking TNF-α-TNFR2 interaction.

Example 7 Binding Affinity of Anti-TNFR2 Antibodies

In this example, binding affinities (monovalent $K_D$) of anti-human TNFR2 antibodies were determined using the ForteBio Octet RED 96 (bio-layer interferometry).

Briefly, IgG Fc capture sensor tips (ForteBio, Cat #18-5060) were hydrated for 10 minutes at room temperature in PBS. A kinetic assay was performed in 96-well plates and ran using following times for each step: a) balance baseline for 100 seconds in PBS, b) loading with anti-human TNFR2 antibodies (hu3-E, hu32-C and hu32C-V1) to at least 0.3 nanometer, c) balance baseline for 1000 seconds, d) association with His-tagged human TNFR2 (Sino Biological, Cat #10417-H08H) or cynomolgus monkey TNFR2 (Sino Biological, Cat #90102-C08H) at serial concentrations of 100 nM, 50 nM, 25 nM, 12.5 nM, 6.25 nM, 3.12 nM and 1.56 nM for 80 seconds respectively, and e) dissociation in PBS for 600 seconds. The data sets were fitted with a 1:1 Global fitting Model using Octet software.

The affinities of the three anti-human TNFR2 antibodies were determined and listed in Table 3 as follows.

TABLE 3

Affinities of anti-TNFR2 antibodies to recombinant human and cynomolgus monkey TNFR2

| Antibodies | Antigens | KD (M) | kon(1/Ms) | kdis(1/s) |
|---|---|---|---|---|
| hu3-E | Human TNFR2 | 5.32E−09 | 3.61E+05 | 1.92E−03 |
| | Cynomolgus TNFR2 | 3.62E−09 | 5.12E+05 | 1.85E−03 |
| hu32-C | Human TNFR2 | 6.06E−10 | 2.77E+05 | 1.68E−04 |
| | Cynomolgus TNFR2 | 3.74E−10 | 5.28E+05 | 1.97E−04 |
| hu32C-V1 | Human TNFR2 | 9.09E−10 | 3.93E+05 | 3.57E−04 |
| | Cynomolgus TNFR2 | 4.14E−10 | 5.73E+05 | 2.37E−04 |

The results suggested that all three antibodies specifically bound to human TNFR2. Particularly, antibody hu3-E showed a monovalent $K_D$ of 5.32 nM to human TNFR2, and 3.62 nM to cynomolgus monkey TNFR2; Antibody hu32-C showed monovalent $K_D$ of 0.61 nM to human TNFR2, and 0.37 nM to cynomolgus monkey TNFR2; antibody hu32C-V1 showed monovalent $K_D$ of 0.91 nM to human TNFR2, and 0.41 nM to cynomolgus monkey TNFR2.

Example 8 In Vitro Evaluation of the Humanized Antibodies

Co-Stimulate Human CD8+ T Cell to Release IFNγ

Human PBMC was obtained from healthy donors. Mononuclear cells were isolated in SepMate-50 tubes (StemCell Technologies) containing Lymphoprep density gradient reagent (StemCell Technologies).

Total CD8$^+$ T cells were purified with negative selection kit (Miltenyi, Cat #130-096-495) according to manufacturer's instructions. 96-well plates (Corning, Cat #3799) were coated with 0.5 µg/mL functional-grade anti-CD3 (eBioscience, Cat #16-0037-85) and serial dilutions of the anti-TNFR2 antibodies (hu3-E and hu32-C) or negative control IgG (diluted from a starting concentration of 60 µg/mL, and 3 fold serial dilution) in PBS at 4° C. overnight. On the next day, the coated plates were washed twice with DPBS buffer (Hyclone. Cat #SH30256.01). 1×10$^5$ CD8$^+$ T cells in 200 µl in medium (comprising 90% RPMI 1640 (Gibco, Cat #22400) complete medium, 10% FBS (Gibco, Cat #10099-141) and 1 µg/ml soluble anti-CD28 (Biolegend, Cat #302934)) were added to each well, cultured at 37° C. for 72 h. Culture supernatant is collected and tested for IFNγ levels with ELISA kit (R&D Systems, Cat #DY202). Results were shown in FIG. 5 Assay buffer in the Figure refers to the 0.5 µg/ml functional-grade anti-CD3 (eBioscience, Cat #16-0037-85) in PBS only.

The results showed that hu3-E can stimulate CD8$^+$ T cells to release IFNγ in a dose dependent manner, while hu32-C has no obvious effect at the concentration described above.

Proliferation of T Cells Mediated by Anti-TNFR2 Antibody Co-Stimulation

Human PBMC was obtained from healthy donors. Mononuclear cells were isolated in SepMate-50 tubes (StemCell Technologies) containing Lymphoprep density gradient reagent (StemCell Technologies), as above. Total CD8$^+$ and CD4$^+$ T cells were purified with negative selection kit (Miltenyi, Cat #130-096-495 and Cat #130-096-533) for later use. 96-well plates (Corning, Cat #3799) were coated with 0.5 µg/ml functional-grade anti-CD3 (eBioscience, Cat #16-0037-85) and serial dilutions of the anti-TNFR2 antibodies (hu3-E and hu32-C) or negative control IgG (diluted from a starting concentration of 60 µg/mL, and 3 fold serial dilution) in PBS at 4° C. overnight. On the next day, the coated plates were washed twice with DPBS buffer (Hyclone, Cat #SH30256.01). 1×10$^5$ CD8+ or CD4$^+$ T cells in 200 µl in medium (comprising 90% RPMI 1640 (Gibco, Cat #22400) complete medium, 10% FBS (Gibco, Cat #10099-141) and 1 µg/ml soluble anti-CD28 (Biolegend, Cat #302934)) were added to each well, cultured at 37° C. for 72 h. 72 h later, 100 µl cell culture supernatant per well is discarded and 100 µl CellTiter-Glo® luminescent cell viability assay reagent (Promega, Cat #G7572) is added and mixed well. 5 min later, 100 µl mixture is transferred to a new 96-well assay plate (Corning, Cat #3917). The assay plate was read using a Microplate reader F200 (Tecan, Cat #F200). Results were shown in FIG. 6. Assay buffer in the Figure refers to the 0.5 µg/ml functional-grade anti-CD3 (eBioscience, Cat #16-0037-85) coating buffer only.

The results further confirmed that hu3-E can stimulate T cell proliferation, while hu32-C has no obvious effect at the concentration described above.

Activation of T Cells Mediated by Anti-TNFR2 Antibody Co-Stimulation In Vitro Depended on Fc Cross-Linking Human PBMC was obtained from healthy donors. Mononuclear cells were isolated in SepMate-50 tubes (StemCell Technologies) containing Lymphoprep density gradient reagent (StemCell Technologies).

Total CD8+ T cells were purified with negative selection kit (Miltenyi, Cat #130-096-495) for later use. 96-well plates (Corning, Cat #3799) were coated with 0.5 μg/ml functional-grade anti-CD3 (eBioscience, Cat #16-0037-85) and serial dilutions of the anti-TNFR2 antibodies (hu3-E and hu32-C) or negative control IgG (diluted from a starting concentration of 30 μg/mL, and 3 fold serial dilution) at 4° C. overnight for plate-bound antibody assay. For soluble antibody assay, 96-well plates were only coated with 0.5 μg/ml functional-grade anti-CD3.

On the next day, the coated plates were washed twice with DPBS buffer (Hyclone, Cat #SH30256.01). For plate-bound antibody assay, 1×10⁵ CD8+ T cells in 200 μl in the medium (comprising 90% RPMI 1640 (Gibco. Cat #22400) complete medium, 10% FBS (Gibco, Cat #10099-141) and 1 μg/ml soluble anti-CD28 (Biolegend, Cat #302934)) were added to each well, cultured at 37° C. for 72 h.

For soluble antibody assay, 1×10⁵ CD8+ T cells in 200 μl in medium (comprising 90% RPMI 1640 (Gibco, Cat #22400) complete medium, 10% FBS (Gibco, Cat #10099-141) and 1 μg/ml soluble anti-CD28 (Biolegend, Cat #302934)) were added to each well, then serial dilutions of anti-TNFR2 antibody (hu3-E and hu32-C) and negative control IgG (diluted from a starting concentration of 30 μg/mL, and 3 fold serial dilution) were added respectively. The culture was cultured at 37° C. for 72 h. 72 h later, the culture supernatant was collected and tested for IFNγ levels with ELISA kit (R&D Systems, Cat #DY202), results were shown in FIG. 7.

The results showed that hu3-E can activate T cells by co-stimulation in vitro, depending on Fc cross-linking.

Example 9 Pharmacokinetics of Humanized Antibodies in Rat

Pharmacokinetic profile of anti-TNFR2 humanized antibody in rat was evaluated. Procedures involving the care and use of animals in the study were reviewed and approved by PhamaLagancy.

Three naive Rats (Shanghai Sippr-BK laboratory animal Co. Ltd.) were used for each antibody. In the study, the anti-TNFR2 antibodies (hu3-E, hu32-C) were injected intravenously into the rats at a single dose of 10 mg/kg respectively. Blood samples were obtained at various time-points between 0 and 336 hours (0-14 days, at day 0, 10 minute, 30 minute, 1 hour, 4 hour, 6 hour in day 1, and day 2, day 4, day 7, day 10 and day 14). All samples were processed to obtain serum, and the serum was cryopreserved at −70~−86° C. until being analyzed. The concentration of Anti-TNFR2 antibody present in the serum was determined. The pharmacokinetic parameters were listed in Table 4.

Human TNFR2, human Fc tag protein (huTNFR2-huFc. SEQ ID NO:46) was immobilized onto 96-well plates (Costar, Cat #42592) at 0.5 μg/mL by incubation in PBS (Hyclone, Cat #SH30256.01) overnight at 4° C. The plates were then blocked by incubation with 1% BSA in PBS for one hour at 37° C. After blocking, the plates were washed three times with PBST (PBS containing 0.05% Tween20).

Anti-TNFR2 antibodies (hu32-C or hu3-E) were diluted at 0.12 μg/mL in the serum dilution buffer (PBS containing 0.05% Tween 20 and 0.5% BSA including 2% v/v rat serum) and 3-fold serial diluted 6 times, total 7 concentration antibody solution are obtained as standard curve. At the same time. 40 ng/mL. 4 ng/mL and 0.4 ng/mL antibodies as the high, middle and low quality control respectively were diluted by serum dilution buffer. All rat serum samples were diluted by pre-dose mixed rat serum and dilution buffer (PBS containing 0.05% Tween 20 and 0.5% BSA), to keep the final concentration in the range of 40-0.4 ng/mL, and containing 2% v/v rat serum in sample dilution. The standard curve, quality control and samples were added into plate and incubated for one hour at 37° C. Then, the plates were washed three times with PBST, incubated for one hour at 37° C. with Peroxidase AffiniPure Goat Anti-Human IgG, F(ab')₂ fragment specific (Jackson ImmunoResearch. Cat #109-035-097) diluted 1/20,000 in the dilution buffer, and then washed with PBST again. 50 μL/well TMB (Thermo, Cat #34028) was added into plates, after 15 minutes, reaction was stopped with 1M $H_2SO_4$. The absorbance at 450 nm-620 nm was determined.

TABLE 4

| PK parameters of Anti-TNFR2 antibodies in rat | | | |
|---|---|---|---|
| PK parameters | Unit | hu3-E | hu32-C |
| $T_{1/2}$ | day | 6.5 | 6.9 |
| Cmax | μg/ml | 175.8 | 212.0 |
| $AUC_{last}$ | day * μg/ml | 660.2 | 896.2 |
| $AUC_{INF}$ | day * μg/ml | 903.5 | 1200.4 |
| CL | ml/day/kg | 11.1 | 8.5 |
| $MRT_{INF}$ | day | 10.3 | 10.1 |
| Vss | ml/kg | 113.6 | 84.5 |

The pharmacokinetics of the two humanized antibodies hu32-C and hu3-E are normal in rats.

Example 10 Family Cross-Binding to TNFR Superfamily Protein

Although hybridoma clones could not bind to TNFR1, LTβR and Osteoprotegerin, there are other types of TNFR superfamily proteins. Here we test the humanized antibodies hu3-E and hu32-C's binding to human 4-1BB, CD40, OX40, GITR, CD27 and HVEM proteins.

4-1BB (Sino Biological, Cat #10041-H08H), CD40 (Sino Biological, Cat #10774-H08H), OX40 (Sino Biological, Cat #10481-H08H), GITR (Sino Biological, Cat #13643-H08H), CD27 (Sino Biological, Cat #10039-H31H) and HVEM (Sino Biological, Cat #10334-H03H) were immobilized onto 96-well plates by incubation with PBS(Hyclone, Cat #SH30256.01) overnight at 4° C. The plates were blocked by incubation with 1% BSA in PBS for one hour at 37° C. After blocking, the plates were washed three times with PBST (PBS containing 0.05% Tween20). Serially diluted anti-TNFR2 antibodies were prepared in dilution buffer (PBS containing 0.05% Tween20 and 0.5% BSA) (starting concentration 0.4 μg/mL, 3 folds dilution) and added into plate, then incubated for one hour at 37° C. The plates were then washed 3 times with PBST (PBS containing 0.05% Tween20). Peroxidase-labeled Goat anti-human F(ab')₂ IgG (JacksonImmuno Research. Cat #109-035-097) diluted 1:20000 in the dilution buffer was then added to each well of the plate, as the ELISA plates. Afterwards, the ELISA plates were incubated for 60 min at RT and then washed 3 times with PBST. Finally, 50 μL/well TMB (Thermo, Cat #34028) was added to each well and the reaction was terminated using 1 M H$_2$SO$_4$. The plates were read on a Microplate reader at 450 nm.

Results were shown in FIG. 8 It is suggested that humanized antibodies hu3-E and hu32-C did not bind to human 4-1BB, CD40, OX40, GITR, CD27 or HVEM proteins.

Example 11 Anti-TNFR2 Antibodies had In Vivo Anti-Tumor Effect

The in vivo efficacy of the anti-TNFR2 antibodies was studied in hTNFR2 K1 mice bearing colon carcinoma.

For the experiments herein, 4-5 weeks humanized mice C57BL/6J-Tnfrsf1b$^{em2(hTMFRSF1B)Smoc}$ (Shanghai Model Organisms Center, Inc) expressing the extracellular portion of human TNFR2 were used.

MC38 cells (OBiO Technology (Shanghai) Corp., Ltd.) were transduced with nucleic acid encoding ovalbumin (OVA GenBank: AAB59956.1) using retroviral transduction. The cells were subsequently cloned by limiting dilution. The clones highly expressing OVA protein were selected as MC38-OVA clones. The MC38-OVA clones were maintained in DMEM (Gibco, Cat #11995-065) with 10% fetal bovine serum and 4 μg/mL Puromycin (Gibco, Cat #A11138-03).

C57BL/6J-Tnfrsf1b$^{em2(hTMFRSF1B)Smoc}$ mice of 5-6 weeks were subcutaneously implanted with 1×10$^6$ MC38-OVA cells, and were randomized into 3 groups on Day 0 when the mean tumor volumes reached approximately 60 mm$^3$ (Length×Width$^2$/2). On Day 0, 3, 7, 10, mice were intraperitoneally administered with hu32-C (15 mg/kg), hu3-E (15 mg/kg), and PBS, respectively. Tumor volumes were monitored by caliper measurement twice per week during the study.

Treatment with the two anti-TNFR2 antibodies both resulted in significant tumor growth inhibition compared to PBS group. Data is shown in Table 5 below.

TABLE 5

MC38-OVA tumor growth inhibition

| Group | Dose | Animal number | Tumor volume(mm$^3$)$^a$ (on Day 14) | TGI (%) $^b$ | P$^c$ |
|---|---|---|---|---|---|
| PBS | / | 6 | 598.6 ± 98.61 | / | / |
| hu32-C | 15 mg/kg | 7 | 192.5 ± 38.7 | 68.06% | <0.001 |
| hu3-E | 15 mg/kg | 5 | 181.2 ± 31.3 | 69.16% | <0.001 |

$^a$Tumor volume data were presented as Mean ± SEM;
$^b$TGI = (1 − relative tumor volume in treated group/relative tumor volume in PBS group) * 100%
$^c$Compared to PBS group, two-way ANOVA were performed, followed by Tukey's multiple comparison test.

Example 12 Improvement of Hu32-C Purity

Single point mutation on FR regions were done to improve the purity of hu32-C. Q38H substitution are made on the FR regions of hu32-C light chain to obtain an antibody named as hu32C-V1. The hu32-C and hu32C-V1 were both expressed and purified under same produces, as described in Example 3. Purity of the products were determined by SEC-HPLC and affinities were determined by Fortebio (as described in Example 7). SEC-HPLC results are shown in FIG. 9, and affinity results can be seen Table. 3.

It could be seen from the results that the affinity of hu32C-V1 was consistent with hu32-C, whereas the purity of the expressed products were significantly improved. The proportion of the main peak of antibodies were increased from 91.4% (hu32-C) to 97.0% (hu32C-V1) on SEC-HPLC.

The results suggested that the Q38H mutation can improve the purity of the antibody hu32-C while does not influence its properties like affinity.

Example 13 Epitope Mapping

In order to examine the epitope that the humanized antibody of the present invention binds to on its target protein human TNFR2, 11 segments from the extracellular domain of human TNFR2 (SEQ ID NO:50) was constructed to replace the corresponding segments in the extracellular domain of the mouse TNFR2 protein (SEQ ID NO:51) respectively. As a result, 11 mouse TNFR2 variants (SEQ ID NO:52-62) wherein each segment of human TNFR2 replacement of the corresponding region were obtained.

The eleven TNFR2 protein segments sequences were constructed and listed on the Table 6 as below.

TABLE 6 the segments from the human amino acid sequences and SEQ ID NO.

| Name of TNFR2 protein Sequences | Sequence ID number | Regions that have the segments from the human TNFR2 protein (numbering without the signal peptide) |
|---|---|---|
| Human TNFR2 | SEQ ID NO: 50 | 1L-235D |
| Mouse TNFR2 | SEQ ID NO: 51 | — |
| 019-1 | SEQ ID NO: 52 | 17T-54D |
| 019-2 | SEQ ID NO: 53 | 56S-97C |
| 019-3 | SEQ ID NO: 54 | 98T-141K |
| 019-4 | SEQ ID NO: 55 | 143P-181T |
| 019-5 | SEQ ID NO: 56 | 39G-75C |
| 019-6 | SEQ ID NO: 57 | 76G-121K |
| 019-0-0.5 | SEQ ID NO: 58 | 1L-31C |
| 019-0-1 | SEQ ID NO: 59 | 1L-54D |
| 019-0.5-1 | SEQ ID NO: 60 | 17T-31C |
| 019-0.5-2 | SEQ ID NO: 61 | 1L-16S |
| 019-12 | SEQ ID NO: 62 | 1L-96C |

According to the binding assay ELISA, the 11 variants, the human TNFR2 and the mouse TNFR2 protein were tested for its binding with the antibodies of the present invention (hu3-E and hu32C-V1). Different TNFR2 proteins were coated on the plate with 0.5 μg/mL and blocked overnight. The antibodies were diluted from a starting concentration of 0.4 μg/mL, and 3 fold serial dilution and added to the microtiter plate and incubated at 37° C. The subsequent steps were consistent with the ELISA-binding method (see EXAMPLE 4).

The results of the binding assay showed that hu3-E and hu32C-V1 both bind to human TNFR2, but not to mouse TNFR2.

The results further suggested that the humanized antibody hu3-E bound to the epitope of human TNFR2 on 1 L-31 C (binding to 019-0-0.5). The humanized antibody hu3-E did not bound the variants of human TNFR2 protein, 019-1, 019-2, 019-3, 0194, 019-5, 019-6, 019-0.5-1 and 019-0.5-2, except 019-0-0.5 and 019-0-1. Consequently, according to the crystal structure analysis of human TNFR2, amino acid mutations of Q4A, E13A, S16A, and Q26A were performed separately on human TNFR2, and the binding to hu3-E was examined in ELISA-binding method according to the steps above. The results showed the 26$^{th}$ glutamine on the sequence of human TNFR2 was the key amino acid for bound hu3-E to human TNFR2. The results of antibody hu3-E binding to different TNFR2 are shown in FIG. 10.

Another humanized antibody hu32-C bound to IL-96C (binding to 019-12) TNFR2 protein. The mutant hu32C-V1 has the same binding epitope of human TNFR2 as hu32-C. The results of the binding of antibody hu32C-V1 to different TNFR2 segments are shown in FIG. 11. The humanized antibody hu32C-V1 only bound 019-12, other variants of human TNFR2 protein, 019-2, 019-3, 019-4, 019-5, 019-6, 019-0.5-1, 019-0.5-2 and 019-0-0.5 were not bound with hu32C-V1. Additionally, 019-1 and 019-0-1 shown the weak but not negligible binding signal with hu32C-V1, this suggested the sequence 17T-54D may comprise amino acid(s) in the epitope of hu32C-V1.

Example 14 Anti-TNFR2 Antibodies had Anti-Tumor Effect In Vivo with or without Combination with Anti-Mouse PD1 Antibody, and with or without Fc Effect In vivo the efficacy of the anti-TNFR2 antibodies was studied in hTNFR2 KI mice bearing colon carcinoma.

Hu3-E (mu), An anti-TNFR2 antibody with L234A, L235A, D265A, P329A (EU numbering) amino acid mutation (Fc function removed) was constructed. The expression and purification of the antibodies follows the procedures as described in Example 3.

For the experiments herein. 4-5 weeks humanized mice C57BL/6J-Tnfrsf1b$^{em2(hTMFRSF1B)Smoc}$ expressing the extracellular portion of human TNFR2 were purchased from Shanghai Model Organisms Center, Inc.

MC38 cells (OBiO Technology (Shanghai) Corp., Ltd.) were transduced with nucleic acid encoding ovalbumin (OVA GenBank: AAB59956.1) using retroviral transduction. The cells were subsequently cloned by limiting dilution. The clones highly expressing OVA protein were selected as MC38-OVA clones. The MC38-OVA clones were maintained in DMEM (Gibco, Cat #11995-065) with 10% fetal bovine serum and 4 µg/mL Puromycin (Gibco, Cat #A11138-03).

C57BL/6J-Tnfrsf1b$^{em2(hTMFRSF1B)Smoc}$ mice of 5-6 weeks were subcutaneously implanted with 1×10$^6$ MC38-OVA cells, and were randomized into 6 groups on Day 0 when the mean tumor volumes reached 80-100 mm$^3$ (L×W$^2$/2). On Day 0, 3, 7, 10, and 14, mice were intraperitoneally administered with hu3-E (mu) (10 mg/kg), hu3-E (3 mg/kg), hu3-E (10 mg/kg), Anti-PD1 antibody (Bio X Cell, Cat #BE0146) (1 mg/kg), Anti-PD1 antibody (1 mg/kg) combine with hu3-E (10 mg/kg) and PBS, respectively. Tumor volumes were monitored by caliper measurement twice per week during the study. 6 mice in each group.

Treatment of both anti-TNFR2 antibodies resulted in significant tumor growth inhibition compared to PBS group, The Fc portion is directly related to the efficacy of hu3-E. Removal of the Fc-FcγR interactions by mutation will reduce the anti-tumor effect of the anti-TNFR2 antibody, at the same time, the anti-TNFR2 antibody shows a significant anti-tumor effect combination with the anti-PD1 antibody. The combined effect is better than the single use of these two antibodies. The grouping detail and the results are shown in Table 7 below.

TABLE 7

MC38-OVA tumor growth inhibition

| Group | Dose (mg/kg) | Animal number | Tumor volume(mm$^3$)$^a$ (on Day 17) | TGI (%) $^b$ | P$^c$ |
|---|---|---|---|---|---|
| PBS | / | 6 | 1536.67 ± 176.48 | / | / |
| hu3-E | 10 | 6 | 579.01 ± 126.50 | 62.32% | <0.01 |
| hu3-E(mu) | 10 | 6 | 830.66 ± 132.37 | 45.94% | <0.01 |
| hu3-E | 3 | 6 | 1091.87 ± 123.54 | 28.95% | <0.01 |
| Anti-PD1 antibody | 1 | 6 | 907.66 ± 109.86 | 40.93% | <0.01 |
| hu3-E + Anti-PD1 antibody | 10 + 1 | 6 | 307.03 ± 96.79 | 80.01% | <0.01 |

$^a$Tumor volume data were presented as Mean ± SEM;
$^b$ TGI = (1 − relative tumor volume in treated group/relative tumor volume in PBS group) * 100%
$^c$P < 0.01 significantly different from PBS group (Dunnett's multi-comparison test).

Example 15 Anti-TNFR2 Antibody Bound to Human TNFR2 Expressed on Activated PBMCs A cell based binding assay was established to determine whether anti-human TNFR2 antibody of the present invention could bind to human TNFR2 expressed on the activated PBMCs. Human PBMC was obtained from healthy donors. PBMCs were stimulated by coated functional-grade anti-CD3 (eBioscience, Cat #16-0037-85, 1 µg/mL) 2 days and then cultured with complete medium (comprising 90% RPMI 1640 HEPES (Gibco, Cat #22400089) with 10% FBS (Gibco, Cat #10099-141)). Then 100 IU/mL IL-2 is added into the medium for another 7 days. Then PBMC were collected and washed twice using PBS (Hyclone, Cat #SH30256.01). 1.5×10$^5$ PBMC cells were resuspended with serial dilutions of the anti-TNFR2 antibody hu3-E (diluted from a starting concentration of 20 µg/ml, and 4-fold serial dilution), and negative control IgG respectively and incubated at 4° C. for 30 minutes. After washed using PBS, cells were resuspended with an R-PE-conjugated AffiniPure Goat Anti-Human IgG, Fcγ Fragment Specific (Jackson immunoResearch, Cat #109-116-098) as secondary reagent (1:200 diluted). The mixture was incubated in PBS at 4° C. for 30 minutes followed by washing twice with PBS. Then, cells were resuspended in PBS. Analysis of specific binding was carried out with the BD Accun C5 flow cytometer (BD Bioscience).

Results were shown in FIG. 12. It is shown that hu3-E could bind to TNFR2 expressed on activated PBMCs from two donors. Otherwise, the IgG Control had no specific binding ability to the activated PBMC mixed from two donors.

Example 16 In Vitro ADCC Effect on Tregs 96-well plates (Corning, Cat #3599) were coated with 3 µg/ml functional-grade anti-CD3 (eBioscience, Cat #16-0037-85) in 4° C. overnight. Next day, the coated buffer was discarded and the plate was washed twice for later use. The PBMC cells from healthy donors which purchased from Schbio Biotech were thawed and collected. Total CD4+ T cells from PBMC cells were purified with negative selection kit (Miltenyi, Cat #130-096-533) according to manufacturer's instructions. And the purified CD4+ T cells were plated into the anti-CD3 coated 96-w plate in 1~5×10$^4$ cells/well in 200 µL Treg inducing buffer (RPMI1640 medium containing 10% FBS, 20 ng/mL TGFβ1, 100 IU/mL IL-2, 2 µg/mL anti-CD28 and 0.04 mM β-mercaptoethanol) and cultured for 5 days to obtain the induced Treg cells for following use.

Total NK cells from PBMC cells were purified with negative selection kit (Miltenyi, Cat #130-092-657) according to manufacturer's instructions. In the ADCC assay, 20,000 cells/well of in vitro induced Treg cells in 50 μl assay buffer (99% MEM-α (Gibco, Cat #41061-029) containing 1% FBS (Gibco, Cat #10099-141)) were added to a 96-well assay plate (Corning, Cat #3599). 50 μl/well of the 6-point series dilutions of hu3-E or hu32-C (series dilution, the final assay concentrations started from 1.2 μg/mL and 5-fold diluted) and an anti-TNFR2 antibody-001-H10 (BioInvent, WO2020089474A1, Heavy chain: SEQ ID. No:74; Light chain: SEQ ID NO:75) as control were added to cells respectively. Then 200,000 cells/well of purified human NK effector cells in 100 μl 99% MEM-α (Gibco, Cat #41061-029) containing 1% FBS (Gibco, Cat #10099-141) and 200 IU/ml human recombinant IL-2 assay buffer were added to each well. The %-w plate was incubated for 24 hours at 37° C., 5% CO2. After incubation, the 96-w plate was centrifuged at low speed (2000 rpm) for 3 min to allow the precipitation of cell pellet. Then, 50 μL/well of supernatant was carefully aspirated from the plates and transferred to a new 96-well plate. An equal volume of LDH cytotoxicity detection solution (Roche, Cat #11644793001) was added into the plate and incubated at room temperature for 30 min. The absorbance was read by Infinite F50 plate-reader at wavelength of 490 nm. The results were showed in FIG. 13.

The results showed that the hu3-E could not induce ADCC effect on induced Treg cells while hu32-C could induce ADCC effect on the cells.

Example 17 In Vitro ADCC Effect on CD8+ T Cells 96-well plates (Corning, Cat #3599) were coated with 1 μg/ml functional-grade anti-CD3 (eBioscience, Cat #16-0037-85) in 4° C. overnight. Next day, the coated buffer was discarded and the plate was washed twice for later use. The PBMC cells from healthy donors which purchased from Schbio Biotech were thawed and collected. Total CD8+ T cells from PBMC cells were purified with negative selection kit (Miltenyi, Cat #130-096-495) according to manufacturer's instructions. And the purified CD8+ T cells were plated into the anti-CD3 coated 96-w plate in 1×10^5 cells/well in 200 μL assay buffer (RPMI1640 medium containing 10% FBS, 1 μg/mL anti-CD28) and cultured for 4 days to obtain activated CD8+ T cells for following use.

Total NK cells from PBMC cells were purified with negative selection kit (Miltenyi, Cat #130-092-657) according to manufacturer's instructions. In the ADCC assay, 15,000 cells/well of in vitro activated CD8+ T cells in 50 μl assay buffer (99% MEM-α (Gibco, Cat #41061-029) containing 1% FBS (Gibco, Cat #10099-141)) were added to a 96-well assay plate (Corning, Cat #3599). 50 μl/well of the 6-point series dilutions of hu3-E or hu32-C (series dilution, the final assay concentrations started from 1.2 μg/mL and 5-fold diluted) and an anti-TNFR2 antibody-001-H10 (BioInvent, WO2020089474A1, Heavy chain: SEQ ID. No:74; Light chain: SEQ ID NO:75) as control were added to cells respectively. Then 150,000 cells/well of purified human NK effector cells in 100 μl 99% MEM-α (Gibco, Cat #41061-029) containing 1% FBS (Gibco, Cat #10099-141) and 200 IU/ml human recombinant IL-2 assay buffer were added to each well. The %-w plate was incubated for 24 hours at 37° C., 5% CO2. After incubation, the 96-w plate was centrifuged at low speed (2000 rpm) for 3 min to allow the precipitation of cell pellet. Then, 50 μL/well of supernatant was carefully aspirated from the plates and transferred to a new 96-well plate. An equal volume of LDH cytotoxicity detection solution (Roche, Cat #11644793001) was added into the plate and incubated at room temperature for 30 min. The absorbance was read by Infinite F50 plate-reader at wavelength of 490 nm. The results were showed in FIG. 14.

The results showed that the hu3-E could not induce ADCC effect on induced CD8+ T cells while hu32-C could induce ADCC effect.

SEQUENCE LISTING

Sequence analyzed by Ig blast and abysis, result delineated in Kabat format.

Sequences of Chimeric Antibodies

Sequences of 32A1D5

TABLE I

Sequences of 32A1D5 variable region CDRs

| SEQ ID NO: | CDRs | |
|---|---|---|
| | CDRs of heavy chain variable region 32A1D5-VH | |
| 1 | CDR 1 | TLGMGVG |
| 2 | CDR 2 | HIWWDADKYYNPALKS |
| 3 | CDR 3 | MTGTRYFDV |
| | CDRs of light chain variable region 32A1D5-VL | |
| 4 | CDR 1 | KASQNINKFIA |
| 5 | CDR 2 | YTSTLQP |
| 6 | CDR 3 | LQYGVLWT |

>32A1D5-VH:
SEQ ID NO: 7
QVTLKESGPGILQPSQTLSLTCSFSGFSLNTLGMGVGWIRQPSGKGLEW

LAHIWWDADKYYNPALKSRLTISKDTSKNHVFLKIANADTADTATYYCA

RMTGTRYFDVWGTGTTVTVSS

>32AID5-VL:
SEQ ID NO: 8
DIQMTQSPSSLSASLGDKVTITCKASQNINKFIAWYQHKPGEGPRLLIH

YTSTLQPGIPSRFSGSGSGSDYSFSINNLEPEDIASYYCLQYGVLWTFG

GGTKLEIK

Sequences of 43B7A4

TABLE II

Sequences of 43B7A4 variable region CDRs

| SEQ ID NO | CDRs | |
|---|---|---|
| | CDRs of heavy chain variable region 43B7A4-VH | |
| 9 | CDR 1 | TYGMS |
| 10 | CDR 2 | WIHTYSGVPTYADDFKG |
| 11 | CDR 3 | GLYGVDY |
| | CDRs of light chain variable region 43B7A4-VL | |
| 12 | CDR 1 | KASENVVTYVS |
| 13 | CDR 2 | GASNRYT |
| 14 | CDR 3 | GQSYTYPYT |

>43B7A4-VH:
SEQ ID NO: 15
QAQIQLVQSGPELKKPGETVKISCKASGYTFTTYGMSWVKQAPGKGLKWMGWIHTYSGVPTYADDFKGRFAFSLETSASTAFLQINNLKNEDTATYFCARGLYGVDYWGQGTTLTVSS

>43B7A4-VL:
SEQ ID NO: 16
NIVMTQSPKSMSMSVGERVTLSCKASENVVTYVSWYQQKPEQSPKLLIYGASNRYTGVPDRFTGSGSATDFTLTISSVQAEDLADYHCGQSYTYPYTFGGGTTLEIK

Sequences of hu32-C(Hu32-H1/Hu32-L3)

TABLE III

Sequences of hu32-C(Hu3-H1 heavy chain and Hu3-L3 light chain) variable region CDRs

| SEQ ID NO | | CDRs |
|---|---|---|
| | | CDR of Heavy chain variable region Hu32-H1 |
| 1 | CDR 1 | TLGMGVG |
| 17 | | ACCCTGGGAATGGGAGTGGGA |
| 2 | CDR 2 | HIWWDADKYYNPALKS |
| 18 | | CACATCTGGTGGGACGCCGATAAGTACTATA ATCCTGCTCTGAAGTCC |
| 3 | CDR 3 | MTGTRYFDV |
| 19 | | ATGACAGGCACCCGGTATTTCGACGTG |
| | | Light chains variable region Hu32-L3 |
| 4 | CDR 1 | KASQNINKFIA |
| 20 | | AAGGCCTCCCAGAACATCAATAAGTTTATCGCT |
| 5 | CDR 2 | YTSTLQP |
| 21 | | TATACCAGCACACTGCAGCCC |
| 6 | CDR 3 | LQYGVLWT |
| 22 | | CTGCAGTATGGCGTGCTGTGGACC |

>VH nucleic acid sequence (Hu32-H1):
SEQ ID NO: 23
CAGGTGACACTGAAGGAGTCTGGCCCAACCCTGGTGAAGCCCACCCAGACACTGACCCTGACATGTACCTTCTCTGGCTTTTCTCTGTCCACCCTGGGAATGGGAGTGGGATGGATCAGACAGCCACCTGGCAAGGCCCTGGAGTGGCTGGCTCACATCTGGTGGGACGCCGATAAGTACTATAATCCTGCTCTGAAGTCCCGCCTGACAATCACCAAGGACACAAGCAAGAACCAGGTGGTGCTGACAATGACCAATATGGACCCAGTGGATACAGCCACCTACTATTGCGCTAGGATGACAGGCACCCGGTATTTCGACGTGTGGGGCCAGGGCACCACAGTGACCGTGTCCAGC >VL nucleic acid sequence (Hu32-L3):
SEQ ID NO: 24
GACATCCAGATGACACAGAGCCCATCCAGCCTGTCCGCCTCCGTGGGCGACAGGGTGACCATCACATGCAAGGCCTCCCAGAACATCAATAAGTTTATCGCTTGGTACCAGCAGAAGCCAGGCAAGGTGCCCAAGCTGCTGATCCACTATACCAGCACACTGCAGCCCGGCGTGCCTTCTAGGTTCTCCGGCAGCGGCTCTGGCTCCGACTACACCCTGACAATCTCTTCCCTGCAGCCTGAGGATGTGGCCACCTACTATTGTCTGCAGTATGGCGTGCTGTGGACCTTTGGCGGCGGCACAAAGGTGGAGATCAAG >hu32-C(Hu32-H1/Hu32-L3)

>VH amino acid sequence (Hu32-H1):
SEQ ID NO: 25
QVTLKESGPTLVKPTQTLTLTCTFSGFSLSTLGMGVGWIRQPPGKALEWLAHIWWDADKYYNPALKSRLTITKDTSKNQVVLTMINMDPVDTATYYCARMTGTRYFDVWGQGTTVTVSS >VL amino acid sequence (Hu32-L3):
SEQ ID NO: 26
DIQMTQSPSSLSASVGDRVTITCKASQNINKFIAWYQQKPGKVPKLLIHYTSTLQPGVPSRFSGSGSGSDYTLTISSLQPEDVATYYCLQYGVLWTFGGGTKVEIK Sequence hu32C-V1(Hu32-H1/Hu32-L2V) (Analyzed by Igblast and Abysis, Result Delineated in Kabat Format)

TABLE IV

Sequences of hu32C-V1 (Hu32-H1 heavy chain and Hu32-L2V light chain) variable region CDRs

| SEQ ID NO | | CDRs |
|---|---|---|
| | | CDR of Heavy chain variable region Hu32-H1 |
| 1 | CDR 1 | TLGMGVG |
| 17 | | ACCCTGGGAATGGGAGTGGGA |
| 2 | CDR 2 | HIWWDADKYYNPALKS |
| 18 | | CACATCTGGTGGGACGCCGATAAGTACTATAA TCCTGCTCTGAAGTCC |
| 3 | CDR 3 | MTGTRYFDV |
| 19 | | ATGACAGGCACCCGGTATTTCGACGTG |
| | | CDR of Light chain variable region Hu32-L2V |
| 4 | CDR 1 | KASQNINKFIA |
| 20 | | AAGGCCTCCCAGAACATCAATAAGTTTATCGCT |
| 5 | CDR 2 | YTSTLQP |
| 21 | | TATACCAGCACACTGCAGCCC |
| 6 | CDR 3 | LQYGVLWT |
| 22 | | CTGCAGTATGGCGTGCTGTGGACC |

>hu32C-V1(Hu32-H1/Hu32-L2V)

VH nucleic acid sequence (Hu32-H1):
SEQ ID NO: 23
CAGGTGACACTGAAGGAGTCTGGCCCAACCCTGGTGAAGCCCACCCAGACACTGACCCTGACATGTACCTTCTCTGGCTTTTCTCTGTCCACCCTGGGAATGGGAGTGGGATGGATCAGACAGCCACCTGGCAAGGCCCTGGAGTGGCTGGCTCACATCTGGTGGGACGCCGATAAGTACTATAATCCTGCTCTGAAGTCCCGCCTGACAATCACCAAGGACACAAGCAAGAACCAGGTGGTGCTGACAATGACCAATATGGACCCAGTGGATACAGCCACCTACTATTGCGCTAGGATGACAGGCACCCGGTATTTCGACGTGTGGGGCCAGGGCACCACAGTGACCGTGTCCAGC >VL nucleic acid sequence (Hu32-L2V):
SEQ ID NO: 27
GACATCCAGATGACACAGAGCCCATCCAGCCTGTCCGCCTCCGTGGGCGA
TCGGGTGACCATCACATGCAAGGCCTCCCAGAACATCAATAAGTTTATC
GCTTGGTACCAGCACAAGCCAGGCAAGGTGCCCAAGCTGCTGATCCATTA
TACCAGCACACTGCAGCCCGGCGTGCCTTCTAGGTTCTCCGGCAGCGGC
TCTGGCTCCGACTACACCCTGACAATCTCTTCCCTGCAGCCTGAGGATGT
GGCCACCTACTATTGTCTGCAGTATGGCGTGCTGTGGACCTTTGGCGGCG
GCACAAAGGTGGAGATCAAG >VH amino acid sequence (Hu32-H1):
SEQ ID NO: 25
QVTLKESGPTLVKPTQTLTLTCTFSGFSLSTLGMGVGWIRQPPGKALEW
LAHIWWDADKYYNPALKSRLTITKDTSKNQVVLTMTNMDPVDTATYYCA
RMTGTRYFDVWGQGTTVTVSS >VL amino acid sequence (Hu32-L2V):
SEQ ID NO: 28
DIQMTQSPSSLSASVGDRVTITCKASQNINKFIAWYQHKPGKVPKLLIH
YTSTLQPGVPSRFSGSGSGSDYTLTISSLQPEDVATYYCLQYGVLWTFG
GGTKVEIK Sequence of Hu3-E (Hu3-H3/Hu3-L1) (Analyzed by Igblast and Abysis, Result Delineated in Kabat Format) and Hu3-E(Mu) ((Hu3-H3/Hu3-L1, Only Mutated in Fc Region, with the Mutations L234A, L235A, D265A, P329A (Eu Numbering))

TABLE V

Sequences of hu3-E (Hu3-H3/Hu3-L1) and Hu3-E(mu) (Hu3-H3/Hu3-L1)variable region CDRs

| SEQ ID NO | CDRs | |
|---|---|---|
| | Heavy chains: Hu3-H3 | |
| 9 | CDR 1 | TYGMS |
| 29 | | ACATATGGCATGTCT |
| 10 | CDR 2 | WIHTYSGVPTYADDFKG |
| 30 | | TGGATTCACACATACTCCGGCGTGCCTACCTATGCCGACGACTTCAAGGGC |
| 11 | CDR 3 | GLYGVDY |
| 31 | | GGCCTGTACGGCGTGGATTAT |
| | Light chains: Hu3-L1 | |
| 12 | CDR1 | KASENVVTYVS |
| 32 | | AAGGCTTCTGAGAACGTGGTGACATACGTGTCC |
| 13 | CDR2 | GASNRYT |
| 33 | | GGCGCTTCCAATAGGTACACC |
| 14 | CDR3 | GQSYTYPYT |
| 34 | | GGCCAGTCTTACACCTATCCTTACACA |

>VH nucleic acid sequence (Hu3-H3):
SEQ ID NO: 35
CAGATCCAGCTGGTGCAGAGCGGAGCTGAGGTGAAGAAGCCAGGAGCTT
CCGTGAAGGTGAGCTGTAAGGCCTCTGGCTACACATTCACCACATATGGC
ATGTCTTGGGTGAGACAGGCTCCAGGACAGGGACTGGAGTGGATGGGCT
GGATTCACACATACTCCGGCGTGCCTACCTATGCCGACGACTTCAAGGGC
CGCTTCGCTTTTACACTGGACACCTCTACATCCACCGCCTATATGGAG
CTGAGGAGCCTGCGGTCTGACGATACCGCCGTGTACTATTGCGCTAGGGG
CCTGTACGGCGTGGATTATTGGGGCCAGGGCACACTGGTGACCGTGTCC
AGC >VL nucleic acid sequence (Hu3-L1):
SEQ ID NO: 36
GAGATCGTGATGACCCAGAGCCCAGCTACACTGTCTCTGTCCCAGGAGA
GAGGGCCACCCTGAGCTGCAAGGCTTCTGAGAACGTGGTGACATACGT
GTCCTGGTACCAGCAGAAGCCAGGACAGGCTCCTAGGCTGCTGATCTATG
GCGCTTCCAATAGGTACACCGGCATCCCAGCTCGGTTTAGCGGCTCTGGC
TCCGCTACAGACTTCACCCTGACAATCTCCAGCCTGCAGCCCGAGGATTT
TGCCGTGTACTATTGTGGCCAGTCTTACACCTATCCTTACACATTCGGCC
AGGGCACAAAGCTGGAGATCAAG >VH amino acid sequence (Hu3-H3):
SEQ ID NO: 37
QIQLVQSGAEVKKPGASVKVSCKASGYTFTTYGMSWVRQAPGQGLEWMG
WIHTYSGVPTYADDEKGRFAFTLDTSTSTAYMELRSLRSDDTAVYYCAR
GLYGVDYWGQGTLVTVSS >VL amino acid sequence (Hu3-L1):
SEQ ID NO: 38
EIVMTQSPATLSLSPGERATLSCKASENVVTYVSWYQQKPGQAPRLLIY
GASNRYTGIPARFSGSGSATDFTLTISSLQPEDFAVYYCGQSYTYPYTF
GQGTKLEIK CH for Chimeric Antibodies 32A1D5 and 43B7A4, and Humanized Antibodies hu32-C (Hu32-H1/Hu32-L3) hu32C-V1(Hu32-H1/Hu32-L2V) and Hu3-E (Hu3-H3/Hu3-L1):P01857 www.uniprot.org/uniprot/P01857

>CH nucleic acid sequence:
SEQ ID NO: 39
GCCAGCACCAAGGGACCATCCGTGTTCCCACTGGCCCCCTCCAGCAAGTC
CACCAGCGGAGGAACAGCCGCTCTGGGATGCCTGGTGAAGGACTACTTCC
CAGAGCCCGTGACAGTGAGCTGGAACTCTGGCGCCCTGACCAGCGGAGTG
CACACATTTCCCGCCGTGCTCCAGTCTTCCGGCCTGTACTCTCTGAGCTC
TGTGGTGACCGTGCCCTCCAGCTCTCTGGGCACCCAGACATATATCTGCA
ACGTGAATCACAAGCCAAGCAATACAAAGGTGGACAAGAAGGTGGAGCCC
AAGTCTTGTGATAAGACCCATACATGCCCCCCTTGTCCTGCTCCAGAGCT
GCTGGGAGGACCAAGCGTGTTCCTGTTTCCACCCAAGCCTAAGGACACCC
TGATGATCTCCAGGACCCCCGAGGTGACATGCGTGGTGGTGGACGTGAGC
CACGAGGACCCCGAGGTGAAGTTTAACTGGTACGTGGATGGCGTGGAGGT
GCATAATGCTAAGACCAAGCCTAGGGAGGAGCAGTACAACTCTACCTATC

```
GGGTGGTGTCCGTGCTGACAGTGCTGCACCAGGACTGGCTGAACGGCAAG
GAGTATAAGTGCAAGGTGTCTAATAAGGCCCTGCCCGCTCCTATCGAGAA
GACCATCTCCAAGGCCAAGGGCCAGCCTAGAGAGCCACAGGTGTACACAC
TGCCTCCATCTCGCGACGAGCTGACCAAGAACCAGGTGTCCCTGACATGT
CTGGTGAAGGGCTTCTATCCTTCCGACATCGCTGTGGAGTGGGAGAGCAA
CGGCCAGCCAGAGAACAATTACAAGACCACACCCCCTGTGCTGGACTCCG
ATGGCAGCTTCTTTCTGTATAGCAAGCTGACCGTGGATAAGTCCAGGTGG
CAGCAGGGCAACGTGTTTTCTTGCTCCGTGATGCATGAGGCTCTGCACAA
TCATTATACACAGAAGAGCCTGTCTCTGTCCCCTGGCAAGTAA
```

```
>CH amino acid sequence:
                                        SEQ ID NO: 40
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK*
```

CH for hu3-E(mu) (Hu3-H3/Hu3-L1)

```
>CH amino acid sequence:
                                        SEQ ID NO: 73
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPEAAGGPSVFLFPPKPKDTLMISRTPEVTCVVVAVS
HEDPEVKFNWYVDGVEVHNAKTKPREEQYNSTYRVVSVLTVLHQDWLNGK
EYKCKVSNKALAAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK*
```

CL for Chimeric Antibodies 32A1D5 and 43B7A4, and Humanized Antibodies hu32-C (Hu32-H1/Hu32-L3) hu32C-V1(Hu32-H1/Hu32-L2V) and Hu3-E (Hu3-H3/Hu3-L1) and Hu3-E(Mu) (Hu3-H3/Hu3-L1) P01834 www.uniprot.org/uniprot/P01834

```
>CL nucleic acid sequence:
                                        SEQ ID NO: 41
CGGACGGTGGCTGCACCATCTGTCTTCATCTTCCCGCCATCTGATGAGCA
GTTGAAATCTGGAACTGCCTCTGTTGTGTGCCTGCTGAATAACTTCTACC
CCAGAGAAGCCAAAGTGCAGTGGAAGGTGGACAACGCCCTGCAGAGCGGA
AACAGCCAGGAAAGCGTGACAGAGCAGGATTCCAAGGATTCCACATACAG
CCTGAGCAGCACACTGACACTGTCCAAGGCCGACTACGAGAAGCACAAG
GTGTACGCCTGCGAAGTGACACACCAGGGACTGTCCTCCCCTGTGACAAA
GAGCTTCAACAGAGGAGAATGCTAA
```

```
>CL amino acid sequence:
                                        SEQ ID NO: 42
RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTK
SFNRGEC*
```

IgG (Negative Control)
WO2008068246A1 Foravirumab

```
>heavy chain amino acid sequence:
                                        SEQ ID NO: 43
QVQLVESGGGAVQPGRSLRLSCAASGFTFSSYGMHWVRQAPGKGLEWVAV
ILYDGSDKFYADSVKGRFTISRDNSKNTLYLQMNSLRAEDTAVYYCAKVA
VAGTHFDYWGQGTLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKRVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG
```

```
>light chain amino acid sequence:
                                        SEQ ID NO: 44
DIQMTQSPSSLSASVGDRVTITCRASQGIRNDLGWYQQKPGKAPKLLIYA
ASSLQSGVPSRFSGSGSGTDFTLTISSLQPEDFATYYCQQLNSYPPTFGG
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC
``` huTNFR2 Amino Acid Sequences

```
>huTNFR2-mFc amino acid sequence:
                                        SEQ ID NO: 45
MAPVAVWAALAVGLELWAAAHALPAQVAFTPYAPEPGSTCRLREYYDQTA
QMCCSKCSPGQHAKVFCTKTSDTVCDSCEDSTYTQLWNWVPECLSCGSRC
SSDQVETQACTREQNRICTCRPGWYCALSKQEGCRLCAPLRKCRPGFGVA
RPGTETSDVVCKPCAPGTFSNTTSSTDICRPHQICNVVAIPGNASMDAVC
TSTSPTRSMAPGAVHLPQPVSTRSQHTQPTPEPSTAPSTSFLLPMGPSPP
AEGSTGDGCKPCICTVPEVSSVFIFPPKPKDVLTITLTPKVTCVVVAISK
DDPEVQFSWFVDDVEVHTAQTQPREEQFNSTFRSVSELPIMHQDWLNGKE
FKCRVNSAAFPAPIEKTISKTKGRPKAPQVYTIPPPKEQMAKDKVSLTCM
ITDFFPEDITVEWQWNGQPAENYKNTQPIMNTNGSYFVYSKLNVQKSNWE
AGNTFTCSVLHEGLHNHHTEKSLSHSPGK
```

```
>huTNFR2-huFc amino acid sequence:
                                        SEQ ID NO: 46
MAPVAVWAALAVGLELWAAAHALPAQVAFTPYAPEPGSTCRLREYYDQTA
QMCCSKCSPGQHAKVFCTKTSDTVCDSCEDSTYTQLWNWVPECLSCGSRC
```

-continued
SSDQVETQACTREQNRICTCRPGWYCALSKQEGCRLCAPLRKCRPGFGVA
RPGTETSDVVCKPCAPGTFSNTTSSTDICRPHQICNVVAIPGNASMDAVC
TSTSPTRSMAPGAVHLPQPVSTRSQHTQPTPEPSTAPSTSFLLPMGPSPP
AEGSTGDDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVD
KSRWQQGNVFSCSVMHEALHNHYTQKSLSLSPGK- >cyno-TNFR2-huFc amino acid sequence:
SEQ ID NO: 47
MAPAAVWAALAVGLELWAAGHALPAQVAFTPYAPEPGGTCRLREYYDQTA
QMCCSKCPPGQHAKVFCTKTSDTVCDSCEDSTYTQLWNWVPECLSCGSRC
SSDQVETQACTREQNRICTCRPGWYCALSKQEGCRLCAQLRKCRPGFGVA
RPGTETSDVVCKPCAPGTFSNTTSSTDICRPHQICHVVAIPGNASMDAVC
TSTSPTRSMAPGAVHLPQPVSTRSQHTQPTPAPSTAPGTSFLLPVGPSPP
AEGSTGDDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVD
KSRWQQGNVFSCSVMHEALHNHYTQKSLSLSPGK- Expression Sequence for Cell Screening and Cell Immunization >HuTNFR2:
SEQ ID NO: 48
MAPVAVWAALAVGLELWAAAHALPAQVAFTPYAPEPGSTCRLREYYDQTA
QMCCSKCSPGQHAKVFCTKTSDTVCDSCEDSTYTQLWNWVPECLSCGSRC
SSDQVETQACTREQNRICTCRPGWYCALSKQEGCRLCAPLRKCRPGFGVA
RPGTETSDVVCKPCAPGTFSNTTSSTDICRPHQICNVVAIPGNASMDAVC
TSTSPTRSMAPGAVHLPQPVSTRSQHTQPTPEPSTAPSTSFLLPMGPSPP
AEGSTGDFALPVGLIVGVTALGLLIIGVVNCVIMTQVKKKPLCLQREAKV
PHLPADKARGTQGPEQQHLLITAPSSSSSSLESSASALDRRAPTRNQPQA
PGVEASGAGEARASTGSSDSSPGGHGTQVNVTCIVNVCSSSDHSSQCSSQ
ASSTMGDTDSSPSESPKDEQVPFSKEECAFRSQLETPETLLGSTEEKPLP
LGVPDAGMKPS- >CynoTNFR2:
SEQ ID NO: 49
MAPAAVWAALAVGLELWAAGHALPAQVAFTPYAPEPGGTCRLREYYDQTA
QMCCSKCPPGQHAKVFCTKTSDTVCDSCEDSTYTQLWNWVPECLSCGSRC
SSDQVETQACTREQNRICTCRPGWYCALSKQEGCRLCAQLRKCRPGFGVA
RPGTETSDVVCKPCAPGTFSNTTSSTDICRPHQICHVVAIPGNASMDAVC
TSTSPTRSMAPGAVHLPQPVSTRSQHTQPTPAPSTAPGTSFLLPVGPSPP
AEGSTGDIVLPVGLIVGVTALGLLIIGVVNCVI- Anti-Human TNFR2 Antibodies Epitope Mapping (Signal Peptides are Underlined)

>extracellular region of human TNFR2:
SEQ ID NO: 50
<ins>MAPVAVWAALAVGLELWAAAHAL</ins>PAQVAFTPYAPEPGSTCRLREYYDQA
QMCCSKCSPGQHAKVFCTKTSDTVCDSCEDSTYTQLWNWVPECLSCGSR
CSSDQVETQACTREQNRICTCRPGWYCALSKQEGCRLCAPLRKCRPGFG
VARPGTETSDVVCKPCAPGTFSNTTSSTDICRPHQICNVVAIPGNASMD
AVCTSTSPTRSMAPGAVHLPQPVSTRSQHTQPTPEPSTAPSTSFLLPMG
PSPPAEGSTGD >extracellular region of mouse TNFR2:
SEQ ID NO: 51
<ins>MAPAALWVALVFELQLWATGHT</ins>VPAQVVLTPYKPEPGYECQISQEYYDRK
AQMCCAKCPPGQYVKHFCNKTSDTVCADCEASMYTQVWNQFRTCLSCSSS
CTTDQVEIRACTKQQNRVCACEAGRYCALKTHSGSCRQCMRLSKCGPGFG
VASSRAPNGNVLCKACAPGTFSDTTSSTDVCRPHRICSILAIPGNASTDA
VCAPESPTLSAIPRTLYVSQPEPTRSQPLDQEPGPSQTPSILTSLGSTPI
IEQSTKGG >019-1:
SEQ ID NO: 52
<ins>MYLGLNCVFIVFLLKGVQS</ins>VPAQVVLTPYKPEPGYTCRLREYYDQTAQMC
CSKCSPGQHAKVFCTKTSDTVCDDCEASMYTQVWNQFRTCLSCSSSCTTD
QVEIRACTKQQNRVCACEAGRYCALKTHSGSCRQCMRLSKCGPGFGVASS
RAPNGNVLCKACAPGTFSDTTSSTDVCRPHRICSILAIPGNASTDAVCAP
ESPTLSAIPRTLYVSQPEPTRSQPLDQEPGPSQTPSILTSLGSTPIIEQS
TKGGDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNG
KEYKCKVSNKALPAPIEKTISKAKGQPREPQVYTLPPSRDELTKNQVSLT
CLVKGFYPSDIAVEWESNGQPENNYKTTPPVLDSDGSFFLYSKLTVDKSR
WQQGNVFSCSVMHEALHNHYTQKSLSLSPGK*

>019-2:
SEQ ID NO: 53
<ins>MYLGLNCVFIVFLLKGVQS</ins>VPAQVVLTPYKPEPGYECQISQEYYDRKAQM
CCAKCPPGQYVKHFCNKTSDTVCASCEDSTYTQLWNWVPECLSCGSRCSS
DQVETQACTREQNRICACEAGRYCALKTHSGSCRQCMRLSKCGPGFGVAS
SRAPNGNVLCKACAPGTFSDTTSSTDVCRPHRICSILAIPGNASTDAVCA
PESPTLSAIPRTLYVSQPEPTRSQPLDQEPGPSQTPSILTSLGSTPIIEQ
STKGGDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLN -continued

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK*

>019-3:
SEQ ID NO: 54
MYLGLNCVFIVFLLKGVQSVPAQVVLTPYKPEPGYECQISQEYYDRKAQM

CCAKCPPGQYVKHFCNKTSDTVCADCEASMYTQVWNQFRTCLSCSSSCTT

DQVEIRACTKQQNRVCTCRPGWYCALSKQEGCRLCAPLRKCRPGFGVARP

GTETSDVVCKACAPGTFSDTTSSTDVCRPHRICSILAIPGNASTDAVCAP

ESPTLSAIPRTLYVSQPEPTRSQPLDQEPGPSQTPSILTSLGSTPHIEQS

TKGGDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSR

WQQGNVFSCSVMHEALHNHYTQKSLSLSPGK*

>019-4:
SEQ ID NO: 55
MYLGLNCVFIVFLLKGVQSVPAQVVLTPYKPEPGYECQISQEYYDRKAQM

CCAKCPPGQYVKHFCNKTSDTVCADCEASMYTQVWNQFRTCLSCSSSCTT

DQVEIRACTKQQNRVCACEAGRYCALKTHSGSCRQCMRLSKCGPGFGVAS

SRAPNGNVLCKPCAPGTFSNTTSSTDICRPHQICNVVAIPGNASMDAVCT

PESPTLSAIPRTLYVSQPEPTRSQPLDQEPGPSQTPSILTSLGSTPIIEQ

STKGGDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK*

>019-5:
SEQ ID NO: 56
MYLGLNCVFIVFLLKGVQSVPAQVVLTPYKPEPGYECQISQEYYDRKAQM

CCAKCPPGQHAKVFCTKTSDTVCDSCEDSTYTQLWNWVPECLSCSSSCTT

DQVEIRACTKQQNRVCACEAGRYCALKTHSGSCRQCMRLSKCGPGFGVAS

SRAPNGNVLCKACAPGTFSDTTSSTDVCRPHRICSILAIPGNASTDAVCA

PESPTLSAIPRTLYVSQPEPTRSQPLDQEPGPSQTPSILTSLGSTPIIEQ

STKGGDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK*

>019-6:
SEQ ID NO: 57
MYLGLNCVFIVFLLKGVQSVPAQVVLTPYKPEPGYECQISQEYYDRKAQM

CCAKCPPGQYVKHFCNKTSDTVCADCEASMYTQVWNQFRTCLSCGSRCSS

DQVETQACTREQNRICTCRPGWYCALSKQEGCRLCAPLRKCGPGFGVASS

RAPNGNVLCKACAPGTFSDTTSSTDVCRPHRICSILAIPGNASTDAVCAP

ESPTLSAIPRTLYVSQPEPTRSQPLDQEPGPSQTPSILTSLGSTPHIEQS

TKGGDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSR

WQQGNVFSCSVMHEALHNHYTQKSLSLSPGK*

>019-0-0.5:
SEQ ID NO: 58
MYLGLNCVFIVFLLKGVQSLPAQVAFTPYAPEPGSTCRLREYYDQTAQMC

CAKCPPGQYVKHFCNKTSDTVCADCEASMYTQVWNQFRTCLSCSSSCTTD

QVEIRACTKQQNRVCACEAGRYCALKTHSGSCRQCMRLSKCGPGFGVASS

RAPNGNVLCKACAPGTFSDTTSSTDVCRPHRICSILAIPGNASTDAVCAP

ESPTLSAIPRTLYVSQPEPTRSQPLDQEPGPSQTPSILTSLGSTPIIEQS

TKGGDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSR

WQQGNVFSCSVMHEALHNHYTQKSLSLSPGK*

>019-0-1:
SEQ ID NO: 59
MYLGLNCVFIVFLLKGVQSLPAQVAFTPYAPEPGSTCRLREYYDQTAQMC

CSKCSPGQHAKVFCTKTSDTVCDDCEASMYTQVWNQFRTCLSCSSSCTTD

QVEIRACTKQQNRVCACEAGRYCALKTHSGSCRQCMRLSKCGPGFGVASS

RAPNGNVLCKACAPGTFSDTTSSTDVCRPHRICSILAIPGNASTDAVCAP

ESPTLSAIPRTLYVSQPEPTRSQPLDQEPGPSQTPSILTSLGSTPIIEQS

TKGGDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSR

WQQGNVFSCSVMHEALHNHYTQKSLSLSPGK*

>019-0.5-1:
SEQ ID NO: 60
MYLGLNCVFIVFLLKGVQSVPAQVVLTPYKPEPGYTCRLREYYDQTAQMC

CAKCPPGQYVKHFCNKTSDTVCADCEASMYTQVWNQFRTCLSCSSSCTTD

QVEIRACTKQQNRVCACEAGRYCALKTHSGSCRQCMRLSKCGPGFGVASS

-continued

RAPNGNVLCKACAPGTFSDTTSSTDVCRPHRICSILAIPGNASTDAVCAP
ESPTLSAIPRTLYVSQPEPTRSQPLDQEPGPSQTPSILTSLGSTPIIEQS
TKGGDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNG
KEYKCKVSNKALPAPIEKTISKAKGQPREPQVYTLPPSRDELTKNQVSLT
CLVKGFYPSDIAVEWESNGQPENNYKTTPPVLDSDGSFFLYSKLTVDKSR
WQQGNVFSCSVMHEALHNHYTQKSLSLSPGK*

>019-0-0.5-2:
SEQ ID NO: 61

MYLGLNCVFIVFLLKGVQSLPAQVAFTPYAPEPGSECQISQEYYDRKAQM
CCAKCPPGQYVKHFCNKTSDTVCADCEASMYTQVWNQFRTCLSCSSSCTT
DQVEIRACTKQQNRVCACEAGRYCALKTHSGSCRQCMRLSKCGPGFGVAS
SRAPNGNVLCKACAPGTFSDTTSSTDVCRPHRICSILAIPGNASTDAVCA
PESPTLSAIPRTLYVSQPEPTRSQPLDQEPGPSQTPSILTSLGSTPIIEQ
STKGGDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKS
RWQQGNVFSCSVMHEALHNHYTQKSLSLSPGK*

>019-12:
SEQ ID NO: 62

MAPVAVWAALAVGLELWAAAHALPAQVAFTPYAPEPGSTCRLREYYDQTA
QMCCSKCSPGQHAKVFCTKTSDTVCDSCEDSTYTQLWNWVPECLSCGSRC
SSDQVETQACTREQNRICACEAGRYCALKTHSGSCRQCMRLSKCGPGFGV
ASSRAPNGNVLCKACAPGTFSDTTSSTDVCRPHRICSILAIPGNASTDAV

-continued

CAPESPTLSAIPRTLYVSQPEPTRSQPLDQEPGPSQTPSILTSLGSTPHI
EQSTKGGDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVD
KSRWQQGNVFSCSVMHEALHNHYTQKSLSLSPGK*

>Anti-TNFR2 Antibody-001-H10

Heavy chain:
SEQ ID NO: 74

EVQLLESGGGLVQPGGSLRLSCAASGFTFDDYGMSWVRQAPGKGLEWVSV
IYSGGSTYYADSVKGRFTISRDNSKNTLYLQMNSLRAEDTAVYYCARDRS
SSWYRDGMDVWGQGTLVTVSSASTKGPSVFPLAPSSKSTSGGTAALGCLV
KDYFPEPVTVSWNSGALTSGVHTFPAVLQSSGLYSLSSVVTVPSSSLGTQ
TYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPG
K*

Light chain:
SEQ ID NO: 75

QSVLTQPPSASGTPGQRVTISCTGSSSNIGAGYDVHWYQQLPGTAPKLLI
YGNSNRPSGVPDRFSGSKSGTSASLAISGLRSEDEADYYCAAWDDSLSGW
VFGGGTKLTVLGRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC*

The invention claimed is:

1. An anti-TNFR2 antibody or the antigen-binding fragment thereof, which comprises (i) three heavy chain complementary determining regions (CDRs) HCDR1, HCDR2, and HCDR3 comprising the amino acid sequence of SEQ ID NO: 1, 2, and 3, respectively, and three light chain complementary determining regions (CDRs) LCDR1, LCDR2, and LCDR3 comprising the amino acid sequence of SEQ ID NO: 4, 5, and 6, respectively; or (ii) three heavy chain complementary determining regions (CDRs) HCDR1, HCDR2, and HCDR3 comprising the amino acid sequence of SEQ ID NO: 9, 10, and 11, respectively, and three light chain complementary determining regions (CDRs) LCDR1, LCDR2, and LCDR3 comprising the amino acid sequence of SEQ ID NO: 12, 13, and 14, respectively.

2. An anti-TNFR2 antibody or the antigen-binding fragment thereof, which comprises (i) three heavy chain complementary determining regions (CDRs) HCDR1, HCDR2, and HCDR3 consisting of the amino acid sequence of SEQ ID NO: 1, 2, and 3, respectively, and three light chain complementary determining regions (CDRs) LCDR1, LCDR2, and LCDR3 consisting of the amino acid sequence of SEQ ID NO: 4, 5, and 6, respectively; or (ii) three heavy chain complementary determining regions (CDRs) HCDR1, HCDR2, and HCDR3 consisting of the amino acid sequence of SEQ ID NO: 9, 10, and 11, respectively, and three light chain complementary determining regions (CDRs) LCDR1, LCDR2, and LCDR3 consisting of the amino acid sequence of SEQ ID NO: 12, 13, and 14, respectively.

3. The anti-TNFR2 antibody or the antigen-binding fragment thereof according to claim 1, which comprises:
(i) a heavy chain variable region comprising the amino acid sequence having at least 90% identity to SEQ ID NO: 7, and a light chain variable region comprising the amino acid sequence having at least 90% identity to SEQ ID No: 8;
(ii) a heavy chain variable region comprising the amino acid sequence having at least 90% identity to SEQ ID NO: 15, and a light chain variable region comprising the amino acid sequence having at least 90% identity to SEQ ID NO: 16;
(iii) a heavy chain variable region comprising the amino acid sequence having at least 90% identity to SEQ ID NO: 25, and a light chain variable region comprising the amino acid sequence having at least 90% identity to SEQ ID NO: 26;
(iv) a heavy chain variable region comprising the amino acid sequence having at least 90% identity to [SEQ ID NO: 25, and a light chain variable region comprising the amino acid sequence having at least 90% identity to SEQ ID No: 28; or
(v) a heavy chain variable region comprising the amino acid sequence having at least 90% identity to SEQ ID NO: 37, and a light chain variable region comprising an amino acid sequence having at least 90% identity to SEQ ID NO: 38.

4. The anti-TNFR2 antibody or the antigen-binding fragment thereof according to claim 1, which comprises:
(i) a heavy chain variable region comprising the amino acid sequence of SEQ ID NO: 7, and a light chain variable region comprising the amino acid sequence of SEQ ID NO: 8;
(ii) a heavy chain variable region comprising the amino acid sequence of SEQ ID NO: 15, and a light chain variable region comprising the amino acid sequence of SEQ ID NO: 16;
(iii) a heavy chain variable region comprising the amino acid sequence of SEQ ID NO: 25, and a light chain variable region comprising the amino acid sequence of SEQ ID NO: 26;
(iv) a heavy chain variable region comprising the amino acid sequence of SEQ ID NO: 25, and a light chain variable region comprising the amino acid sequence of SEQ ID NO: 28; or
(v) a heavy chain variable region comprising the amino acid sequence of SEQ ID NO: 37, and a light chain variable region comprising the amino acid sequence of SEQ ID NO: 38.

5. The anti-TNFR2 antibody or the antigen-binding fragment thereof according to claim 1, which further comprises a heavy chain constant region, and a light chain constant region, wherein
the heavy chain constant region
(i) is or is derived from a human $IgG_1$, $IgG_2$, $IgG_3$, or $IgG_4$ constant region;
(ii) comprises an amino acid sequence having at least 90% identity to the amino acid sequence of SEQ ID NO: 40 or SEQ ID NO: 73; or
(iii) comprises the amino acid sequence of SEQ ID NO: 40 or SEQ ID NO: 73;
and
the light chain constant region
(i) is or is derived from human kappa or lambda light chain constant region,
(ii) comprises an amino acid sequence having at least 90% identity to the amino acid sequence of SEQ ID NO: 42; or
(iii) comprises the amino acid sequence of SEQ ID NO: 42.

6. The anti-TNFR2 antibody or the antigen-binding fragment thereof according to claim 1, which further comprises a heavy chain constant region, or a light chain constant region, wherein
the heavy chain constant region
(i) is or is derived from a human $IgG_1$, $IgG_2$, $IgG_3$ or $IgG_4$ constant region;
(ii) comprises an amino acid sequence having at least 90% identity to the amino acid sequence of SEQ ID NO: 40 or SEQ ID NO: 73; or
(iii) comprises the amino acid sequence of SEQ ID NO: 40 or SEQ ID NO:73;
or
the light chain constant region
(i) is or is derived from human kappa or lambda light chain constant region, (ii) comprises an amino acid sequence having at least 90% identity to the amino acid sequence of SEQ ID NO: 42; or
(iii) comprises the amino acid sequence of SEQ ID NO: 42.

7. The anti-TNFR2 antibody or the antigen-binding fragment thereof according to claim 1, which further comprises a heavy chain constant region, and a light chain constant region, wherein the heavy chain constant region comprises the amino acid sequence of SEQ ID NO: 40 or SEQ ID NO: 73; and the light chain constant region comprises the amino acid sequence of SEQ ID NO: 42.

8. The anti-TNFR2 antibody or the antigen-binding fragment thereof according to claim 1, wherein the antibody is a monoclonal antibody.

9. The anti-TNFR2 antibody or the antigen-binding fragment thereof according to claim 1, wherein the antibody is a chimeric antibody or a humanized antibody.

10. The antibody or the antigen-binding fragment thereof according to claim 1, wherein the antigen-binding fragment is an antibody fragment selected from Fab, Fab', Fab'-SH, Fv, single chain antibody, (Fab')2, diabodies domain antibody (dAb), and linear antibody.

11. The antibody or the antigen-binding fragment thereof according to claim 1, wherein said antibody is a bispecific or multispecific antibody molecule.

12. The antibody or the antigen-binding fragment thereof according to claim 11, wherein said antibody is a bispecific antibody molecule that binds to TNFR2 and an immune checkpoint molecule.

13. The anti-TNFR2 antibody or the antigen-binding fragment thereof according to claim 1, which binds an epitope of TNFR2 comprising an extracellular region of human TNFR2, wherein the epitope is comprised in amino acid sequence from 1 L to 31 C of SEQ ID NO: 58, or amino acid sequence from 1 L to 96 C of SEQ ID NO:62 or in amino acid sequence from 17T-54D of SEQ ID NO:52.

14. The anti-TNFR2 antibody or antigen-binding fragment thereof according to claim 1, which has one or more of the following properties:
  (i) binding to human and/or cynomolgus TNFR2 protein or the fragment thereof in vitro with high affinity;
  (ii) binding to human and/or cynomolgus TNFR2 expressed on cell surface;
  (iii) blocking the interaction/binding between TNF-α and human and/or cynomolgus TNFR2 expressed on cells;
  (iv) activating T-cells
  (v) stimulating a downstream signal pathway of TNFR2;
  (vi) enhancing an immune-response;
  (vii) not inducing antibody-dependent cellular cytotoxicity (ADCC) effects on induced T cells;
  (viii) having anti-tumor effects.

15. An isolated nucleic acid encoding any one or more chains of the anti-TNFR2 antibody according to claim 1 or the fragment thereof.

16. An expression vector comprising the nucleic acid according to claim 1.

17. A host cell comprising the vector according to claim 16, wherein the host cell is a prokaryotic or eukaryotic cell suitable for the preparation of antibodies or antigen-binding fragments thereof.

18. A method of preparing an anti-TNFR2 antibody or the antigen-binding fragment thereof comprising culturing a host cell comprising a nucleic acid encoding an anti-TNFR2 antibody or the antigen-binding fragment thereof according to claim 1 under conditions suitable for expression of said an anti-TNFR2 antibody or the antigen-binding fragment thereof.

19. An immunoconjugate comprising the anti-TNFR2 antibody or the antigen-binding fragment thereof according to claim 1 and one or more other therapeutic agents.

20. The immunoconjugate of claim 19, wherein the one or more other therapeutic agents is an immunomodulator.

21. A pharmaceutical composition comprising the anti-TNFR2 antibody or the antigen-binding fragment thereof according to claim 1 and a pharmaceutically acceptable adjuvant.

22. A pharmaceutical composition comprising the anti-TNFR2 antibody or the antigen-binding fragment thereof according to claim 4 and a pharmaceutically acceptable adjuvant.

23. A combination product, comprising the anti-TNFR2 antibody or the antigen-binding fragment thereof according to claim 1, and one or more other therapeutic agents.

24. A combination product, comprising the anti-TNFR2 antibody or the antigen-binding fragment thereof according to claim 1, and another antibody, wherein the other antibody is a PD-1 antibody or a PD-L1 antibody.

25. A method of activating T cells or inducing T cell mediated antitumor activity or stimulating the proliferation of T cells in a subject or treating breast cancer or colon cancer, comprising administering to said subject an effective amount of the anti-TNFR2 antibody or the antigen-binding fragment thereof according to claim 1.

26. The method of claim 25, further comprising administering to said subject in combination with one or more other therapeutic agents.

27. The method of claim 26, wherein the one or more other therapeutic agents is an immunomodulator.

28. The method of claim 26, wherein the other therapeutic agent is a PD-1 antibody or a PD-L1 antibody.

29. A method of detecting TNFR2 in a sample, said method comprising:
  (i) contacting the sample with any anti-TNFR2 antibody or antigen binding fragment thereof according to claim;
  (ii) detecting the formation of a complex between the anti-TNFR2 antibody or antigen binding fragment thereof and the TNFR2; optionally, the anti-TNFR2 antibody is detectably labeled.

30. A kit for detecting TNFR2, comprising the anti-TNFR2 antibody or the antigen-binding fragment thereof according to claim 1.

* * * * *

UNITED STATES PATENT AND TRADEMARK OFFICE
CERTIFICATE OF CORRECTION

PATENT NO. : 11,912,777 B2
APPLICATION NO. : 18/064061
DATED : February 27, 2024
INVENTOR(S) : Xiaoqiang Kang et al.

It is certified that error appears in the above-identified patent and that said Letters Patent is hereby corrected as shown below:

In the Claims

Claim 3, Column 77, Line 57, should read -- acid sequence having at least 90% identity to SEQ ID. --

Claim 16, Column 79, Line 57, should read -- according to claim 15. --

Claim 29, Column 80, Line 49, should read -- or antigen binding fragment thereof according to claim 1. --

Signed and Sealed this
Twenty-first Day of May, 2024

Katherine Kelly Vidal
Director of the United States Patent and Trademark Office